US009789205B2

(12) United States Patent
Kabanov et al.

(10) Patent No.: US 9,789,205 B2
(45) Date of Patent: Oct. 17, 2017

(54) COMPOSITIONS AND METHODS FOR GENE THERAPY

(71) Applicant: Board of Regents of the University of Nebraska, Lincoln, NE (US)

(72) Inventors: Alexander Kabanov, Chapel Hill, NC (US); Elena Batrakova, Chapel Hill, NC (US); Vivek Mahajan, Chapel Hill, NC (US); Matthew J. Haney, Chapel Hill, NC (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 14/537,547

(22) Filed: Nov. 10, 2014

(65) Prior Publication Data

US 2015/0151006 A1    Jun. 4, 2015

Related U.S. Application Data

(60) Provisional application No. 61/645,148, filed on May 10, 2012, provisional application No. 61/647,548, filed on May 16, 2012.

(51) Int. Cl.
*A61K 48/00* (2006.01)
*A61K 38/44* (2006.01)
*C12N 15/85* (2006.01)
*C12N 5/0786* (2010.01)
*A61K 35/15* (2015.01)

(52) U.S. Cl.
CPC ............ *A61K 48/005* (2013.01); *A61K 35/15* (2013.01); *A61K 38/44* (2013.01); *C12N 5/0645* (2013.01); *C12N 15/85* (2013.01)

(58) Field of Classification Search
None
See application file for complete search history.

(56) References Cited

U.S. PATENT DOCUMENTS

| 5,859,308 | A | 1/1999 | Mirochnitchenko et al. |
| 7,709,625 | B2 | 5/2010 | Li et al. |
| 8,518,391 | B1 | 8/2013 | Morgan et al. |
| 2009/0221684 | A1 | 9/2009 | Grinstaff et al. |
| 2012/0108654 | A1 | 5/2012 | Campochiaro |

FOREIGN PATENT DOCUMENTS

WO    WO 2013/170170 A2    11/2013

OTHER PUBLICATIONS

Osada, et al. (2009) "Polymeric micelles from poly(ethylene glycol)—poly(amino acid) block copolymer for drug and gene delivery", Journal of the Royal Society: Interface, 6: S325-39.*

Lukacs, et al. (1993) "Tumor Cells Transfected with a Bacterial Heat-Shock Gene Lose Tumorigenicity and Induce Protection Against Tumors", Journal of Experimental Medicine, 178(7): 343-48.*
Cheng, et al. (2007) "Human Macrophages Promote the Motility and Invasiveness of Osteopontin-Knockdown Tumor Cells", Cancer Research, 67(11): 5141-47.*
Mitrsinovic, et al. (2005) "Microglia Overexpressing the Macrophage Colony-Stimulating Factor Receptor Are Neuroprotective in a Micrglial-Hippocampal Organotypic Coculture System" The Journal of Neuroscience, 25(17): 4442-51.*
Tome, et al. (2001) "Catalase-overexpressing Thymocytes Are Resistant to Glucocorticoid-induced Apoptosis and Exhibit Increased Net Tumor Growth", Cancer Research, 61(3): 2766-73.*
Gaymalov, et al. (2009) "The Effect of the Nonionic Block Copolymer Pluronic P85 on Gene Expression in Mouse Muscle and Antigen Presenting Cells", Biomaterials, 20(6): 1232-45.*
Phillip McClean (1997) "Eukaryotic Chromosome Structure", downloaded from https://www.ndsu.edu/pubweb/~mcclean/plsc431/eukarychrom/eukaryo3.htm. By North Dakota State University, Fargo, ND, No journal, volume or issue numbers, 11 pages long.*
Clotilde Thery (2011) "Exosome Explosion", The Scientist, Midland, Ontario, CA, Published online at http://www.the-scientist.com/?articles.view/articleNo/30793/title/Exosome-Explosion/, No volume, No issue, printed out Apr. 17, 2016, 8 pages long.*
Takahashi, et al. (2003) "Transgene delivery of plasmid DNA to smooth muscle cells and macrophages from a biostable polymer coated stent", Gene Therapy, 10: 1471-78.*
Zuo, et al. (2004) "Fluorescent Proteins Expressed in Mouse Transgenic Lines Mark Subsets of Glia, Neurons, Macrophages, and Dendritic Cells for Vital Examination", The Journal of Neuroscience, 24(9): 10999-11009.*
Mahajan, et al. "Data on macrophage mediated muscle transfection upon delivery of naked plasmid DNA with block copolymers" Data in Brief, 7: 1269-82.*
Yang, et al. (2005) "Promoter- and strain-selective enhancement of gene expression in a mouse skeletal muscle by a polymer excipient Pluronic P85", Journal of Controlled Release, 108: 469-512.*
Fukuyama, et al. (2007) "Intravenous injection of phagocytes transfected ex vivo with FGF4 DNA/biodegradable gelatin complex promotes angiogenesis in a rat myocardial ischemia/reperfusion injury model", Basic Research in Cardiology, 102: 209-16.*
Mahajan, et al. (2016) "Horizontal gene transfer from macrophages to ischemic muscles upon delivery of naked DNA with Pluronic block copolymers", Biomaterials, 75: 58-70.*
International Search Report corresponding to International Application No. PCT/US2013/040577 mailed Sep. 26, 2013.
Attarwala "In vitro evaluations of macrophage-targeted anti-inflammatory gene delivery and transfection using nanoparticles-in-emulsion formulations", *Pharmaceutical Science Master's Theses. Paper 17* (2010) 58 pages.
Biju et al. "Macrophage-mediated GDNF Delivery Protects Against Dopaminergic Neurodegeneration: A Therapeutic Strategy for Parkinson's Disease", *Molecular Therapy* 18(8):1536-1544 (2010).
Brynskikh et al. "Macrophage Delivery of Therapeutic Nanozymes in a Murine Model of Parkinson's Disease", *Nanomedicine (Lond).* 5(3):379-396 (2010).

(Continued)

*Primary Examiner* — Robert M Kelly
(74) *Attorney, Agent, or Firm* — Myers Bigel, P.A.

(57) ABSTRACT

Compositions and methods for transferring a nucleic acid to a target cell using an immune system cell are provided.

11 Claims, 31 Drawing Sheets

(56) References Cited

OTHER PUBLICATIONS

Burke et al. "Macrophages in gene therapy: cellular delivery vehicles and in vitro targets", *J. Leukocyte Biology* 72:417-428 (2002).
Chang et al. "Non-ionic amphiphilic biodegradable PEG-PLGA-PEG copolymer enhances gene delivery efficiency in rat skeletal muscle", *J. Controlled Release* 118:245-253 (2007).
Chen et al. "P85, Optison microbubbles and ultrasound cooperate in mediating plasmid DNA transfection in mouse skeletal muscles in vivo", *Ultrasonics Sonochemistry* 18:513-519 (2011).
Ferenbach et al. "Macrophage Cell Therapy in Renal Disease", *Seminars in Nephrology* 30(3):345-353 (2010).
Griffiths et al. "The macrophage—a novel system to deliver gene therapy to pathological hypoxia", *Gene Therapy* 7:255-262 (2000).
Haney et al. "Cell-mediated Transfer of Catalase Nanoparticles from Macrophages to Brain Endothelial and Neural Cells", *Nanomedicine (Lond.)* 6(7):1215-1230 (2011).
Haney et al. "Specific Transfection of Inflamed Brain by Macrophages: A New Therapeutic Strategy for Neurodegenerative Diseases", *PLOS One* 8(4):1-16 (2013).
Kluth et al. "Gene transfer info inflamed glomeril using macrophages transfected with adenovirus", *Gene Therapy* 7:263-270 (2000).
Klyachko et al. "Macrophages offer a paradigm switch for CNS delivery of therapeutic proteins", *Nanomedicine (Lond.)* 9(9):1403-1422 (2014).
Lai et al. "Pluronic-based cationic block copolymer for forming pDNA polyplexes with enhanced cellular uptake and improved transfection efficiency", *Biomaterials* 32 20 :4594-4603 2011.
Namgung et al. "An acid-labile temperature-responsive sol-gel reversible polymer for enhanced gene delivery to the myocardium and skeletal muscle cells", *Biomaterials* 30:5225-5233 (2009).
Paecharoenchai et al. "Cationic niosomes composed of spermine-based cationic lipids mediate high gene transfection efficiency", *J. Drug Targeting* 20(9):783-792 (2012).
Steele et al. "Factors influencing polycation/siRNA colloidal stability toward aerosol lung delivery", *Eur. J. Pharmaceutics and Biopharmaceutics* 80:14-24 (2012).
Tanaka et al. "Migration of Enhanced Green Fluorescent Protein Expressing Bone Marrow-Derived Microglia/Macrophage into the Mouse Brain Following Permanent Focal Ischemia", *Neuroscience* 117:531-539 (2003).
Zhao et al. "Polyelectrolyte Complex Optimization for Macrophage Delivery of Redox Enzyme Nanoparticles", *Nanomedicine (Lond.)* 6(1):25-42 (2011).
Zhao et al. "GDNF-Transfected Macrophages Produce Potent Neuroprotective Effects in Parkinson's Disease Mouse Model", *PLOS One* 9(9):1-11 (2014).
Notification Concerning Transmittal of International Preliminary Report on Patentability corresponding to International Application No. PCT/US2013/040577 mailed May 28, 2015.

* cited by examiner

A. NEURONS + EXOSOMES FROM MACROPHAGES

B. TRANSFECTED WITH TOMATO PROTEIN pDNA MACROPHAGES

C. NEURONS + EXOSOMES FROM TRANSFECTED MACROPHAGES

A.

1 DAY

B.

5 DAYS

COMPOSITIONS AND METHODS FOR GENE THERAPY

This application is a continuation-in-part of International Patent Application No. PCT/US2013/040577, filed on May 10, 2013, which claims priority under 35 U.S.C. §119(e) to U.S. Provisional Patent Application No. 61/645,148, filed on May 10, 2012, and U.S. Provisional Patent Application No. 61/647,548, filed on May 16, 2012. The foregoing applications are incorporated by reference herein.

This invention was made with government support under Grant Nos. GM103480, NS057748 and CA116591 awarded by the National Institutes of Health and Grant No. W81XWH-09-1-0386awarded by the U.S. Army/Army Medical Research and Material Command. The government has certain rights in the invention.

FIELD OF THE INVENTION

The present invention relates to compositions and methods for the delivery of therapeutic agents to a patient, particularly to sites of inflammation. The invention further relates to methods for transferring a nucleic acid to a target cell.

BACKGROUND OF THE INVENTION

Development anew delivery systems for gene and drug transport for diseases associated with inflammation including cancer, stroke, traumatic brain injury (TBI), neurodegenerative disorders, such as Parkinson's and Alzheimer's diseases (PD and AD), amyotrophic lateral sclerosis (ALS), multiple sclerosis (MS), lysosomal storage diseases, age-related macular degeneration (AMD), Prion disease, meningitis, encephalitis and HIV-1-associated dementia (HAD), mental disorders such as depression, autism, and schizophrenia and others is greatly needed. The challenges faced are: decreased extravasation to the target side such as due to limited blood brain barrier (BBB) permeability, inherent peripheral and brain drug toxicities, and low therapeutic indices. Immunocytes, mononuclear phagocytes (MP; monocytes, macrophages, and dendritic cells), lymphocytes, and neutrophils, as well as stem cells exhibit an intrinsic homing property enabling them to migrate to sites of injury, inflammation, and tumor across the EBB in response to the release of cytokines/chemokines and upregulation of certain cell surface proteins in the diseased tissues and nearby blood vessels. Even in the healthy brain, perivascular macrophages, which reside on the parenchymal side of endothelial cells, originally come from circulating phagocytes, monocytes and macrophages and have shown a remarkable capability to cross an intact BBB with 80% turnover in 3 months. Many reports in the literature indicate that leukocytes traffic primarily between adjacent endothelial cells through the junctional complexes (paracellular migration), or in some cases through the endothelial cell itself (transcellular migration). Under pathological conditions, the rate of immunocytes transport to the inflamed brain tissues is further elevated. The pathobiology of PD, AD and other neurodegenerative diseases is linked to microglial activation and subsequent secretion of neurotoxic factors. These include reactive oxygen and nitrogen species (ROS and RNS) leading to oxidative stress (McGeer et al. (1988) Neurology 38:1285-1291; Busciglio et al. (1995) Nature 378:776-779; Ebadi et al. (1996) Prog. Neurobiol., 48:1-19; Wu et al. (2003) Proc. Natl. Acad. Sci., 100:6145-6150), which affects neuronal, astrocyte, and microglia function by inducing ion transport and calcium mobilization, and activating apoptotic programs. Apoptosis and excitotoxicity are principal causes of mitochondrial-induced neuronal death (Arends et al. (1991) Int. Rev. Exp. Pathol., 32:223-254). Indeed, the mitochondrial respiratory chain affects oxidative phosphorylation and is responsible for ROS production. Such pathways lead to neuronal demise and underlie the pathobiology of PD and AD (Chan, P. H. (2001) J. Cereb. Blood Flow Metab., 21:2-14).

The lack of natural antioxidants (catalase, glutathione and superoxide dismutase) and iron in the substantia nigra (SN) are specifically associated with the pathobiology of PD (Ambani et al. (1975) Arch. Neurol., 32:114-118; Riederer et al. (1989) J. Neurochem., 52:515-520; Abraham et al. (2005) Indian J. Med. Res., 121:111-115). Removing ROS and affecting mitochondria function through targeted delivery of redox enzymes could attenuate disease progression (Gonzalez-Polo et al. (2004) Cell Biol. Int., 28:373-380). Therefore, efficient brain delivery of redox enzymes, such as catalase and superoxide dismutase, or their replicative genetic material can attenuate ROS and improve disease outcomes. Unfortunately, antioxidants when administered as therapeutic agents fail to alter the course of PD-associated neurodegeneration (Pappert et al. (1996) Neurology 47:1037-1042). Such failures may be a result from limited delivery of antioxidants at disease sites. Accordingly, better methods for the delivery of therapeutics such as antioxidants are needed.

SUMMARY OF THE INVENTION

In accordance with the instant invention, method of inhibiting, treating, and/or preventing a disease or disorder (e.g., an inflammatory disease or disorder) in a subject are provided. The instant invention also provides methods of delivering a protein (e.g., a therapeutic protein) and a nucleic acid molecule (e.g., a plasmid) encoding the protein to a site of inflammation within a subject. The methods comprise the administration of composition comprising: a) an immune cell (e.g., a macrophage/monocyte) comprising a nucleic acid molecule encoding a therapeutic protein, particularly a transiently transfected nucleic acid molecule, and b) a pharmaceutically acceptable carrier. In a particular embodiment, the therapeutic protein is an anti-inflammatory, particularly an antioxidant such as catalase or superoxide dismutase. In a particular embodiment, the disease or disorder is a neurodegenerative disease such as Parkinson's disease. In another embodiment the disease or disorder is associated with inflammation such as inflammatory arthritis, inflammatory bowel diseases, inflammatory vascular diseases, cancer, etc. The immune cells used in the methods may be obtained from the subject to be treated (e.g., ex vivo therapy).

The invention further provides methods of transferring a nucleic acid to a target cell, comprising contacting the target cell with an immune system cell transfected with the nucleic acid, wherein the nucleic acid is transferred to the target cell. Another aspect of the invention provides methods of transiently transfecting an immune system cell with a nucleic acid, comprising contacting the immune system cell with a composition comprising the nucleic acid and an amphiphilic block copolymer.

The immune cell may be transfected by any method, particularly by any non-viral gene delivery method. In a particular embodiment, the transfection method comprises contacting the immune cell with a composition comprising the nucleic acid molecule and a polycation, cationic lipid, or a non-ionic amphiphilic block copolymer. In a particular embodiment, the amphiphilic block copolymer comprises poly(ethylene oxide) and poly(oxypropylene).

BRIEF DESCRIPTION OF THE DRAWINGS

FIG. 12B shows in vivo transfection of muscle fibers with the use of M2 macrophages transfected with GFP encoding pDNA. Confocal image (left) indicate transfected ischemic muscle fibers expressing GFP in upper right quadrant compared to (right image) non transfected non ischemic muscle fibers in upper right quadrant.

DETAILED DESCRIPTION OF THE INVENTION

Figure 1:
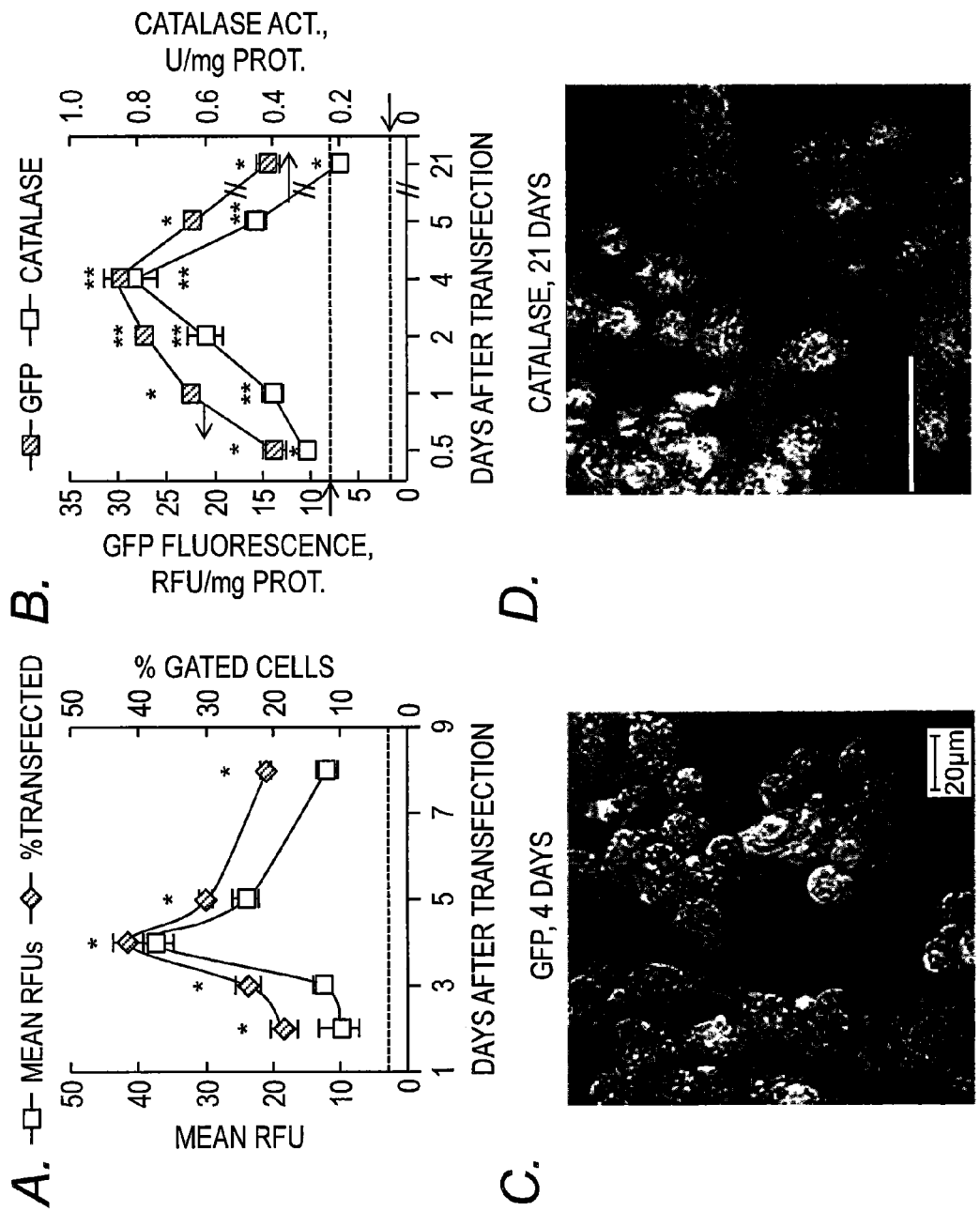
FIG. 1 shows the transfection of macrophages with GFP or catalase pDNA and prolonged release of the encoded protein. Raw 264.7 macrophages were incubated with 2 µg/ml GFP (Panels A, C) or catalase (Panels B, D) pDNA and 300 µl/ml Gene PORTER® 3000 transfection agent, which is a non-viral cationic gene transfer agent, for 4 hours, washed, and cultured in complete media for various times. Levels of the encoded protein and percentage of transfected macrophages were assessed by FACS (Panel A), and the expressed protein was visualized by confocal microscopy on day 4 (Panel C), and day 21 (Panel I)). Up to 40% of cells expressed GFP (Panel A) with the maximum at day 4 (Panels A, C) and sustained expression for at least 21 days (Panel D). For the release studies, macrophages grown on 24-well plates were transfected with: GFP pDNA (Panel B, black squares) or catalase pDNA (Panel B, white squares), then cells were washed, cultured for different times, and amount of the expressed protein was assessed by fluorescence (GFP) or catalytic activity (catalase). In consistence with the transfection levels, maximum of the encoded protein was detected in the culture media at day 4 with sustained levels up to three weeks. Levels of fluorescence and enzymatic activity in non-transfected macrophages are shown by arrow on corresponding axes and dashed lines. Statistical significance of GFP expression levels in macrophages, and GFP or catalase released from macrophages compared to untreated cell levels is shown by asterisk (*p,0.05; **p,0.005) was calculated by one-way ANOVA. Errors are mean±SEM, N=4. The bar: 20 µm.

Inflammation is a common denominator for many diseases. These include cancer, stroke, traumatic brain injury (TBI), neurodegenerative disorders, such as Parkinson's and Alzheimer's diseases (PD and AD), amyotrophic lateral sclerosis (ALS), multiple sclerosis (MS), lysosomal storage diseases, age-related macular degeneration (AMD), Prion disease, meningitis, encephalitis and HIV-1-associated dementia (HAD), mental disorders such as depression, autism, and schizophrenia and others. For example, PD is the fastest growing neurologic disorder in the developed world. Although much of the pathology remains unrealized, it is known to be associated with brain inflammation, microglia activation and neurotoxic activities including ROS that facilitate neuronal damage and death (McGeer et al. (1988) Neurology 38:1285-1291; Busciglio et al. (1995) Nature 378:776-779; Ebadi et al. (1996) Prog. Neurobiol., 48:1-19;

Wu et al. (2003) Proc. Natl. Acad. Sci., 100:6145-6150). Thus, the need to deliver neuroprotectants, in particular, redox enzymes involved in anti-inflammatory neuroprotection, such as catalase and superoxide dismutase (SOD), to control neuroinflammation in the affected brain cannot be overstated. Several studies have shown that reduction of the oxidative stress-related damage, including ROS scavenging, are attractive strategies if successfully delivered to the sites of inflammation within the brain (Gonzalez-Polo et al. (2004) Cell Biol. Int., 28:373-380; Prasad et al. (1999) Curr. Opin. Neurol., 12:761-770). Unfortunately, many promising approaches fail to show benefits in humans, in part due to severe limitations imparted by the BBB, and the lack of delivery of therapeutic polypeptides to the brain (Beal et al. (1997) Mol. Aspects Med., 18:S169-179; Zhao et al. (2005) Biochem. Pharmacol., 70:1796-1806). Utilizing the common approach to oxidative stress, a novel cell-based gene and drug delivery system of antioxidants was developed herein that features tissue specificity, and efficient penetration of the BBB.

The ability to precisely upregulate genes in the inflamed brain holds great therapeutic promise. Here, a novel class of vectors, genetically modified macrophages that carry reporter and therapeutic genes to neural cells are provided. Systemic administration of macrophages transfected ex vivo with a plasmid DNA (pDNA) encoding a potent antioxidant enzyme, catalase, produced month-long expression levels of catalase in the brain resulting in three-fold reductions in inflammation and complete neuroprotection in mouse models of PD. This resulted in significant improvements in motor functions in PD mice. Mechanistic studies revealed that transfected macrophages secreted extracellular vesicles, exosomes, packed with catalase genetic material, pDNA and mRNA, active catalase, and NF-κb, a transcription factor involved in the encoded gene expression. Exosomes efficiently transfer their contents to contiguous neurons resulting in de novo protein synthesis in target cells. Thus, genetically modified macrophages serve as a highly efficient system for reproduction, packaging, and targeted gene and drug delivery to treat inflammatory and neurodegenerative disorders.

Taking advantage of the neuroinflammatory process and the active egress of immunocytes from blood to sites of inflammation, monocytes/macrophages as drug carrier systems have been developed for inflammatory-mediated diseases (Batrakova et al. (2007) Bioconjug. Chem., 18:1498-1506; Brynskikh et al. (2010) Nanomedicine 5:379-396; Batrakova et al. (2011) Expert Opin. Drug Deliv., 8:415-433; Zhao et al. (2011) J. Nanomed. Nanotechnol., S4; Haney et al. (2011) Nanomedicine 6:1215-1230; Zhao et al. (2011) Nanomedicine 6: 25-42; Haney et al. (2012) Nanomedicine 7:815-833). The system rests in the ability of blood borne macrophages to carry antioxidant proteins across the BBB to the affected brain subregions. To preclude macrophage-mediated enzyme degradation, catalase was packaged into a block ionomer complex with a cationic block copolymer, poly(ethyleneimine)-poly(ethylene glycol) producing nanosized particles, "nanozymes." It was demonstrated that such nanozyme-loaded macrophages systemically administered into mice with brain inflammation facilitated nanozyme transport across the BBB. In addition, the cell-carriers provided sustained and prolonged release of catalase suggesting a depot role for the enzyme (Brynskikh et al. (2010) Nanomedicine 5:379-396). It was demonstrated at least a portion of macrophages loaded with nanozyme migrate from the blood away into the tissue and the tissue-associated cell-carriers slowly unload and supply the blood plasma providing sustained levels of catalase in the plasma over seven days.

Furthermore, macrophages discharged nanozyme to contiguous cells facilitating decomposition of ROS, reducing neuroinflammation, and attenuating nigrostriatal degeneration that ultimately produced potent neuroprotection in PD mice. The transfer of nanozyme from macrophages to target recipient cells occurs by a) partial transient fusion of cellular membranes, b) formation of macrophage bridging conduits (BCs), filopodia and lamellipodia, and c) release of exosomes, extracellular vesicles that contain the nanozyme (Haney et al. (2012) Nanomedicine 7:815-833).

Exosomes are specialized membranous vesicles that are secreted by a variety of cells, particularly cells of the immune system: dendritic cells (Thery et al. (2006) Curr. Protoc. Cell Biol., Chapter 3: Unit 3-22), macrophages (Bhatnagar et al. (2007) Blood 110:3234-3244), B cells (Clayton et al. (2005) J. Cell Sci., 118:3631-3638), and T cells (Nolte-'t Hoen et al. (2009) Blood 113:1977-1981). Exosomes were initially thought to be a mechanism for removing unneeded membrane proteins from reticulocytes. Recent studies have shown they are specialized in long distance intercellular communications facilitating transfer of proteins (Johnstone, R. M. (1992) Biochem. Cell Biol., 70:179-190), and functional mRNAs and microRNAs for subsequent protein expression in target cells (Zomer et al. (2010) Commun. Integr. Biol., 3:447-450; Valadi et al. (2007) Nat. Cell Biol., 9:654-659). The efficient cell-to-cell transfer is accomplished by facilitated membrane interactions and fusion, and expression of adhesive proteins and specific vector ligands (tetraspanins, integrins, CD11b and CD18 receptors) on the surface of exosomes (Thery et al. (2006) Curr. Protoc. Cell Biol., Chapter 3: Unit 3-22; Thery et al. (2009) Nat. Rev. Immunol., 9:581-593). To shuttle their cargo, exosomes can attach by these adhesion proteins and fuse with the cell-target membrane. Incorporation of nanoformulated catalase ("nanozyme") in exosomes altered its intracellular localization in target cells of neurovascular unit (neurons, brain microvessel endothelial cells, and astrocytes) enabling it to reach different intracellular compartments such as ER, cytoplasm, and mitochondria, where ROS may be efficiently deactivated by catalase (Haney et al. (2012) Nanomedicine 7:815-833).

Another approach for targeted cell-mediated delivery system is using genetically-modified cell-carriers encoding a therapeutic protein. In this case, modified cells can achieve gene delivery providing a sustained expression of the therapeutic protein in the inflamed brain. It was reported that genetically-modified cell-carriers were used for successful gene therapy of PD and AD. Thus, neurotrophic factors, brain-derived neurotrophic factor (BDNF) (Martinez-Serrano et al, (1996) Eur. J. Neurosci., 8:727-735; Blurton-Jones et al. (2009) Proc. Natl. Acad. Sci., 106:13594-13599), glial cell-line derived neurotrophic factor (GDNF), or vascular endothelial growth factor (VGEF) were delivered by modified neural stem cells (NSC) (Akerud et al. (2001) J. Neurosci., 21:8108-8118; Casper et al. (2002) Cell Transplant 11:331-349; Yasuhara et al. (2005) Brain Res., 1053:10-18), or bone marrow-derived macrophages (Biju et al. (2010) Mol. Ther., 18:1536-1544) for treatment of PD-related inflammation and neuronal degeneration. Furthermore, modified NSC were also used for delivery of neurotrophic factors in AD mouse models (Martinez-Serrano et al. (1996) Eur. J. Neurosci., 8:727-735; Martinez-Serrano et al. (1998) Proc. Natl. Acad. Sci., 95:1858-1863; Garcia et al.

(2010) J. Neurosci., 30:7516-7527; Low et al. (1982) Nature 300:260-262; Pizzo et al. (2006) Mol. Ther., 13:175-182).

Based on the cell-mediated delivery system for nanoformulated catalase, the present work utilized genetically-modified immunocytes for targeted gene and drug delivery in PD model. In particular, RAW 264.7 macrophages were transfected with pDNA encoding reporter proteins (GFP, or luciferase, or tomato protein), or the therapeutic protein (catalase). The gene and protein transfer from genetically-modified macrophages, and their therapeutic effect were evaluated in in vitro and in vivo PD models. It is demonstrated herein for the first time that systemically administered transfected macrophages release exosomes with incorporated in them DNA, mRNA, transcription factors molecules, and the encoded protein. This resulted in the sustained catalase expression and subsequent potent anti-inflammatory and neuroprotective outcomes in PD models. Two models of brain inflammation were used, intracranial (i.c.) injections with lipopolysaccharides (LPS) or 6-hydroxidophamine (6-OHDA). LPS intoxications cause higher levels of neuroinflammation, which was manifested earlier than in case of 6-OHDA injections (typically 48 hours vs. 21 days following the intoxication, respectively) (Zhao et al. (2011) J. Nanomed. Nanotechnol., S4). Nevertheless, hallmarks of 6-OHDA-induced neuroinflammation reflected PD-related process better than LPS-intoxications. Intraperitoneal (i.p.) MPTP-intoxications, which were not used herein, usually cause significant inflammation in peripheral organs (liver, spleen, and kidneys) that redirects considerable portion of macrophages from brain to these peripheral organs. Thus, i.c. intoxications with 6-OHDA and LPS are the most appropriate PD models for cell-mediated drug delivery evaluations. Overall, cell-mediated drug delivery is a strategy for targeted transport of therapeutic genes and drugs, which provides a missing link for translational gene therapy, e.g. for inflammatory and neurodegenerative disorders.

In accordance with the present invention, the gene encoding the protein of interest (e.g., therapeutic protein) is loaded into a cell, which can then be administered to a patient as a therapeutic agent. More specifically, the cell is a circulating cell, in particular, an immune system cell. Immune system cells include, without limitation, a monocyte, a macrophage, a bone marrow derived monocyte, a dendritic cell, a lymphocyte, a T-cell, a B-cell, a neutrophil, an eosinophil, a basophil, and/or combinations thereof. The loaded cells are capable of crossing the BBB and delivering the polypeptide of interest, particularly when the patient has a neurodegenerative or neuroinflammatory disease or disorder. The cells may be isolated from the mammalian subject using cell isolation and separation techniques available in the art. As described hereinbelow, the cells can be transfected using a non-viral gene delivery system (e.g., thereby avoiding the drawbacks of administering virus-loaded to cells to a subject). The loaded cells can be administered parenterally including, but not limited to, subcutaneously, intravenously and intraperitoneally. In addition to that they can be administered directly to the nervous system, in particularly intrathecally, intracerebrally or epidurally. The polypeptide-polyion complexes may also be administered intramuscularly, intradermally, or intracarotidly. A combination of different methods of administration may be used.

In accordance with the present invention, compositions and methods are provided for the delivery of a protein (including polypeptides or peptides), particularly a therapeutic protein, to a subject. In a particular embodiment, the composition comprises cells comprising a nucleic acid encoding the therapeutic protein and, optionally, a pharmaceutically acceptable carrier. In a particular embodiment, the cell is an immune system cell. Immune system cells include, without limitation, monocytes, a macrophage, bone marrow derived monocytes, dendritic cells, lymphocytes, T-cells, B-cells, neutrophils, eosinophils, basophils, and/or combinations thereof. In a particular embodiment, the cell is a macrophage. In a specific embodiment of this invention the cell is anti-inflammatory sub-type macrophage. The macrophage may be an M2 macrophage. Different subtypes of M2 macrophages can be obtained by using a combination of cytokines e.g. MCSF, IL-4, IL-10, IL-13, glucocorticoids, transforming growth factor-beta. Also many subtypes of M1 macrophages can be achieved by IFN-gamma, LPS. In a particular embodiment, the cells (e.g., macrophage) are isolated from the subject (e.g., mammalian subject) using cell isolation and separation techniques available in the art. As described hereinbelow, the cells can be transfected with the nucleic acid encoding the therapeutic protein. The transfected cells can be administered parenterally to the subject (e.g., the subject which donated the cells) including, but not limited to, subcutaneously, intravenously and intraperitoneally. In addition to that the cells can be administered directly to the nervous system, in particularly intrathecally, intracerebrally or epidurally.

The methods of the current invention may comprise the use of cells containing one or several nucleic acids encoding one or more polypeptides, or the use of several cells containing different nucleic acids encoding one or more polypeptides, simultaneously or separately from each other. The cells may be in the same composition or may be in separate compositions.

As stated above, the cells may comprise a nucleic acid encoding a therapeutic protein, i.e., it effects amelioration and/or cure of a disease, disorder, pathology, and/or the symptoms associated therewith. In a particular embodiment, the therapeutic protein is an anti-inflammatory or antimicrobial (e.g., antibacterial, antibiotic, antiviral, etc.). In a particular embodiment, the therapeutic protein is an antioxidant. As used herein, the term "antioxidant" refers to compounds that neutralize the activity of reactive oxygen species or inhibit the cellular damage done by the reactive species or their reactive byproducts or metabolites. The term "antioxidant" may also refer to compounds that inhibit, prevent, reduce or ameliorate oxidative reactions. Examples of antioxidants include, without limitation, antioxidant enzymes (e.g., superoxide dismutase, catalase, or peroxidases such as glutathione peroxidase). In another embodiment, the therapeutic protein is a neurotrophic protein, for example, glial cell line-derived neurotrophic factor (GDNF), brain-derived neurotrophic factor (BDNF), neurturin (NTN), or vascular endothelial growth factor (VEGF).

A further aspect of the present invention relates to compositions and methods for the transfer of a nucleic acid to a target cell in vitro or in vivo. In this aspect, target cells are contacted with cells comprising a nucleic acid to be transferred (i.e., a transfer cell) such that the nucleic acid is transferred from the transfer cell to the target cell. In a particular embodiment, the cell is an immune system cell. Immune system cells include, without limitation, monocytes, a macrophage, bone marrow derived monocytes, dendritic cells, lymphocytes, T-cells, B-cells, neutrophils, eosinophils, basophils, and/or combinations thereof. In a particular embodiment, the cell is a macrophage. In a specific embodiment the cell is an anti-inflammatory sub-type macrophage. The macrophage may be an M2 macrophage or an M1 macrophage. M2 macrophages are preferred. Macrophages can be differentiated to M2 phenotype by treating with IL-4 or exposure to Macrophage Colony Stimulating Factor (MCSF).

The nucleic acid may be any nucleic acid of interest. For example, the nucleic acid can encode a protein (including polypeptides or peptides) or functional RNA, e.g., a therapeutic protein, a reporter protein, an antisense RNA, or a siRNA.

In some embodiments, the target cell is a cell type that is difficult to transfect with a nucleic acid using typical transfection methods. Cells that are difficult to transfect include, without limitation, terminally differentiated or non-dividing cell types such as neurons and muscle (e.g., skeletal muscle cells, cardiac muscle cells); primary cells such as hematopoietic stem cells, mesenchymal stem cells, embryonic stem cells, and human umbilical vein endothelial cells (HUVECs); fibroblasts; and some continuous cell lines such as lymphoma/leukemia cells, macrophages, and dendritic cells. In certain embodiments, the target cell is a neuron or a muscle cell.

In certain embodiments, the target cell is an in vitro or ex vivo cell, e.g., a cell in culture (e.g., in a dish, flask, incubator, or bioreactor). In these embodiments, the immune system cell (e.g., macrophage) comprising the nucleic acid to be transferred is added to the culture so as to be brought in contact with the target cell.

In certain embodiments, the target cell is an in vivo cell, e.g., a cell in a subject, such as an animal (e.g., a research animal or disease model animal) or a human (e.g., a patient). In these embodiments, the immune system cell (e.g., macrophage) comprising the nucleic acid to be transferred is brought into contact with the target cell, e.g., by localized or systemic delivery to the subject. The immune system cell may be a cell isolated from the subject comprising the target cell or from a different source.

As stated hereinabove, the cells of the instant invention comprise a nucleic acid molecule encoding the therapeutic protein. In a particular embodiment, the cells are transfected (e.g., transiently transfected) with the nucleic acid encoding the protein. In a particular embodiment, the nucleic acid is a vector, particularly a non-viral vector, more particularly a plasmid. In a particular embodiment, the vector does not integrate into the genome of the cell. The term "transfection" refers to the introduction of foreign DNA into cells. The term "transient transfection" refers to the introduction of foreign DNA into a cell where the foreign DNA fails to integrate into the genome of the transfected cell. Transfection of the cells of the instant invention may be accomplished by any method known in the art. Transfection methods include, without limitation, physical methods such as microinjection, gene gun, impalefection, hydrostatic pressure, electroporation, continuous infusion, and sonication; and chemical methods such as lipofection, calcium phosphate-DNA co-precipitation, DEAE-dextran-mediated transfection, polybrene-mediated transfection, liposome fusion, complexes with a positively charged (cationic) lipids and/or polymers (e.g., polymeric gene carriers (polyplexes)), and co-delivery with amphiphilic block copolymers as described hereinbelow.

Specific examples of non-viral transfection agents include but are not limited to GenePORTER 3000® Transfection Reagent: a proprietary cationic lipid formulation (marketed by Genlantis Inc), Lipofectamine™: a proprietary cationic lipid based transfection reagent (marketed by Life Technologies Corp), ExpiFectamine™ transfection: a cationic lipid based transfection reagent (marketed by Life Technologies Corp), HiPerFect® transfection reagent, a cationic lipid based transfection reagent (marketed by Qiagen Inc.), Effectene® Transfection reagent: a lipid based transfection regent (marketed by Qiagen Inc), FuGENE® 6 transfection reagent: a lipid based formulation (marketed by Promega Corp) as well as polymer-based systems including but not limited to jetPEI™-Macrophage, a mannose conjugated linear polyethylenimine that binds to cells expressing mannose-specific membrane receptors, such as GMCSF activated macrophages (marketed by Polyplus transfection Inc.), PromoFectin a proprietary non liposomal cationic polymer (marketed by Promokine Germany), Turbofect™ Transfection reagent, a proprietary cationic polymer (marketed by Thermoscientific). Other non-viral transfection reagents include Xfect™ Transfection reagent (marketed by Clontech), TurboFectin™ 8 (marketed by Origene Inc) and others.

In a particular embodiment, the cells are transfected using an amphiphilic block copolymer. The amphiphilic block copolymer may be present in a composition with the nucleic acid to be transfected at a concentration of about 0.01% to about 10%, particularly about 0.3% to about 5%, particularly about 0.3% to about 2%.

Amphiphilic polymers according to the instant invention are preferably amphiphilic block copolymers. Generally, amphiphilic block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block.

Amphiphilic block copolymers may comprise two, three, four, five, or more blocks. For example, the amphiphilic block copolymer may be of the general formula A-B, B-A, A-B-A, B-A-B, A-B-A-B-A, or B-A-B-A-B, wherein A represents a hydrophilic block and B represents a hydrophobic block. The amphiphilic block copolymers may be in a linear formation or a branched, hyper-branched, dendrimer, graft, or star formation (e.g., A(B)n, (AB)n, AnBm starblocks, etc.), In a particular embodiment, the amphiphilic block copolymer comprises hydrophilic blocks at the termini. The blocks of the amphiphilic block copolymers can be of variable length. In a particular embodiment, the blocks of the amphiphilic block copolymer comprise from about 2 to about 800 repeating units, particularly from about 5 to about 200, about 5 to about 150, or about 5 to about 100 repeating units.

The blocks of the amphiphilic block copolymer may comprise a single repeating unit. Alternatively, the blocks may comprise combinations of different hydrophilic or hydrophobic units. Hydrophilic blocks may even comprise hydrophobic units so long as the character of the block is still hydrophilic (and vice versa). For example, to maintain the hydrophilic character of the block, the hydrophilic repeating unit would predominate.

In a particular embodiment, the hydrophilic segments may be polymers with aqueous solubility more that about 1% wt. at 37° C., while hydrophobic segments may be polymers with aqueous solubility less than about 1% wt. at 37° C. In a particular embodiment, polymers that at 1% solution in bi-distilled water have a cloud point above about 37° C., particularly above about 40° C., may be the hydrophilic segments. In a particular embodiment, polymers that at 1% solution in bi-distilled water have a cloud point below about 37° C., particularly below about 34° C., may be the hydrophobic segments.

The amphiphilic compound is preferably biocompatible. Examples of biocompatible amphiphilic copolymers are known in the art, including, for example, those described in Gaucher et al. (J. Control Rel. (2005) 109:169-188). Examples of amphiphilic block copolymers include, without limitation: poly(2-oxazoline) amphiphilic block copolymers, polyethylene glycol-polylactic acid (PEG-PLA), PEG-PLA-PEG, polyethylene glycol-poly(lactic-co-glycolic acid) (PEG-PLGA), polyethylene glycol-polycaprolactone (PEG-PCL), polyethylene glycol-polyaspartate (PEG-PAsp), polyethylene glycol-poly(glutamic acid) (PEG-PGlu), polyethylene glycol-poly(acrylic acid) (PEG-FAA), polyethylene glycol-poly(methacrylic acid) (PEG-PMA), polyethylene glycol-poly(ethyleneimine) (PEG-PEI), polyethylene glycol-poly(L-lysine) (PEG-PLys), polyethylene glycol-poly(2-(N,N-dimethylamino)ethyl methacrylate) (PEG-PDMAEMA), polyethylene glycol-chitosan, and derivatives thereof. Examples of other biocompatible amphiphilic compounds include phospholipids and PEGylated phospholipids.

Examples of hydrophilic block(s) include, without limitation, polyetherglycols, dextran, gelatin, albumin, poly(ethylene oxide), methoxy-poly(ethylene glycol), copolymers of ethylene oxide and propylene oxide, polysaccharides, polyvinyl alcohol, polyvinyl pyrrolidone, polyvinyltriazole, N-oxide of polyvinylpyridine, N-(2-hydroxypropyl)methacrylamide (HPMA), polyortho esters, polyglycerols, polyacrylamide, polyoxazolines (e.g., methyl or ethyl poly(2-oxazolines)), polyacroylmorpholine, and copolymers or derivatives thereof. Examples of hydrophobic block(s) include, without limitation, polyanhydride, polyester, poly (propylene oxide), poly(lactic acid), poly(lactic-co-glycolic acid), poly(lactic-co-glycolide), poly aspartic acid, polyoxazolines (e.g., butyl, propyl, pentyl, nonyl, or phenyl poly (2-oxazolines)), poly glutamic acid, polycaprolactone, poly (propylene oxide), poly(1,2-butylene oxide), poly (n-butylene oxide), poly(ethyleneimine), poly (tetrahydrofurane), ethyl cellulose, polydipyrolle/dicabazole, starch, and/or poly(styrene).

In a particular embodiment, the hydrophilic block(s) of the amphiphilic block copolymer comprises poly(ethylene oxide) (also known as polyethylene glycol) or a polysaccharide. In a particular embodiment, the hydrophobic block(s) of the amphiphilic block copolymer comprises polyanhydride, polyester, poly(lactic acid), polycaprolactone, poly(propylene oxide), poly(1,2-butylene oxide), poly (n-butylene oxide), poly (tetrahydrofurane), and/or poly (styrene).

In a particular embodiment, the amphiphilic block copolymer comprises at least one block of poly(oxyethylene) and at least one block of poly(oxypropylene). In a particular embodiment, the amphiphilic block copolymer is a triblock of poly(oxyethylene)-poly(oxypropylene)-poly(oxyethylene).

Polymers comprising at least one block of poly(oxyethylene) and at least one block of poly(oxypropylene) are commercially available under such generic trade names as "lipoloxamers", "Pluronic®, " "poloxamers," and "synperonics." Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EO block in tens of weight percent (for example, 80% weight if the digit is 8, or 10% weight if the digit is 1). The remaining first one or two digits encode the molecular mass of the central PO block. To decipher the code, one should multiply the corresponding number by 300 to obtain the approximate molecular mass in daltons (Da). Therefore Pluronic® nomenclature provides a convenient approach to estimate the characteristics of the block copolymer in the absence of reference literature. For example, the code 'F127' defines the block copolymer, which is a solid, has a PO block of 3600 Da (12X300) and 70% weight of EO. The precise molecular characteristics of each Pluronic® block copolymer can be obtained from the manufacturer.

Amphiphilic block copolymers such as Pluronic® block copolymers may be characterized by different hydrophilic-lipophilic balance (HLB) (Kozlov et al. (2000) Macromolecules, 33:3305-3313). The HLB value, which typically falls in the range of 1 to 31 for Pluronic® block copolymers, reflects the balance of the size and strength of the hydrophilic groups and lipophilic groups of the polymer (see, for example, Attwood and Florence (1983) "Surfactant Systems: Their Chemistry, Pharmacy and Biology," Chapman and Hall, New York) and can be determined experimentally by, for example, the phenol titration method of Marszall (see, for example, "Parfumerie, Kosmetik", Vol. 60, 1979, pp. 444-448; Rompp, Chemistry Lexicon, 8th Edition 1983, p. 1750; U.S. Pat. No. 4,795,643). HLB values for Pluronic® polymers are available from BASF Corp. HLB values can be approximated by the formula:

$$HLB = -36\frac{y}{x+y} + 33,$$

wherein y is the number of hydrophobic propylene oxide units and x is the number of hydrophilic ethylene oxide units, though HLB values provided by BASF are preferred. Notably, as hydrophobicity increases, HLB decreases. In a particular embodiment, the amphiphilic block copolymer of the instant invention has an intermediate HLB or low HLB. For example, the HLB for the amphiphilic block copolymer may be about 20 or less, particularly about 18 or less, particularly about 16 or less. In some embodiments, the molecular mass of the PO block is between about 300 and about 4000, e.g., between about 800 and about 3600, e.g., between about 1000 and about 2900, e.g., between about 1400 and about 2500. The physical and molecular characteristics of Pluronic® polymers are well known in the art and can be found, for example, in Paschalis et al., Colloids and Surfaces A: Physicochemical and Engineering Aspects 96, 1-46 (1995) and Kozlov et al., Macromolecules 33:3305-3313 (2000), incorporated herein by reference.

In accordance with the instant invention, methods of delivering a protein (e.g., therapeutic protein) to a subject are provided. In a particular embodiment, the methods deliver the protein and a nucleic acid molecule encoding the protein to the subject or cells of the subject. The methods may deliver the protein to a site of inflammation (acute or chronic) in the subject. The methods may deliver the protein to a site of ischemia in the subject. In a particular embodiment, the method delivers the protein to neurons, brain, central nervous system, or brain microvascular endothelial cells. The methods comprise administering a cell of the instant invention to the subject.

In accordance with the instant invention, methods of delivering a protein (e.g., therapeutic protein) or a nucleic acid to a target cell are provided. In a particular embodiment, the methods deliver the protein and a nucleic acid molecule encoding the protein to the cell. The target cell may be a cell that is in vitro, ex vivo, or in vivo. The methods may comprise contacting the target cells (or bringing into close proximity to the target cells) with the cells of the instant invention described hereinabove.

In a particular embodiment of the instant invention, the therapeutic protein and gene encoding the therapeutic protein are included, that can have a therapeutic effect in the disease of interest such as have effect of amelioration and/or cure of a disease, disorder, pathology, and/or the symptoms associated therewith. The proteins may have therapeutic value against diseases associated with inflammation including but not limiting to inflammatory arthritis, inflammatory bowel diseases, inflammatory vascular diseases, cancer, stroke, TBI, PD and AD, ALS, MS, lysosomal storage diseases, AMU, Prion disease, meningitis, encephalitis, HAD, mental disorders such as depression, autism, and schizophrenia and others. Of particular interest are neurological disorders (particularly of the CNS) including, without limitation, neurological degenerative disorders, AD, PD, Huntington's disease, stroke, trauma, infections, meningitis, encephalitis, gliomas, cancers (including brain metastasis), HAD, HIV associated neurocognitive disorders (HAND), paralysis, ALS or Lou Gehrig's disease, MS, CNS-associated cardiovascular disease, prion disease, obesity, metabolic disorders, inflammatory disease, metabolic disorders, and lysosomal storage diseases (LSDs; such as, without limitation, Gaucher's disease, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), Tay-Sachs disease, Sandhoff's disease, Krabbe's disease, metachromatic leukodystrophy, and Fabry disease). Therapeutically active proteins include but are not limited to enzymes, antibodies, hormones, growth factors, other polypeptides, which administration to the brain can effect amelioration and/or cure of a disease, disorder, pathology, and/or the symptoms associated therewith. Neuroactive polypeptides useful in this invention include but are not limited to endocrine factors, growth factors, hypothalamic releasing factors, neurotrophic factors, paracrine factors, neurotransmitter polypeptides, antibodies and antibody fragments which bind to any of the above polypeptides (such neurotrophic factors, growth factors, and others), antibodies and antibody fragments which bind to the receptors of these polypeptides (such as neurotrophic factor receptors), cytokines, endorphins, polypeptide antagonists, agonists for a receptor expressed by a CNS cell, polypeptides involved in lysosomal storage diseases, and the like. In a particular embodiment, the therapeutic protein exerts its effect on the CNS. In another particular embodiment, the therapeutic protein does not cross the BBB by itself.

Examples of specific proteins include, without limitation, catalase, telomerase, superoxide dismutase (SOD), glutathione peroxidase, glutaminase, cytokines, endorphins (e.g. enkephalin), growth factors (e.g., epidermal growth factor (EGF), acidic and basic fibroblast growth factor (aFGF and bFGF), insulin-like growth factor I (IGF-I), brain-derived neurotrophic factor (BDNF), glial-derived neurotrophic factor (GDNF), platelet derived growth factor (PDGF), vascular growth factor (VGF), nerve growth factor (NGF), insulin-like growth factor-II (IGF-II), tumor necrosis factor-B (TGF-B), leukemia inhibitory factor (LIF), various interleukins, and the like), antiapoptotic proteins (BCL-2, PI3 kinase, and the like), amyloid beta binders (e.g. antibodies), modulators of $\alpha$-, $\beta$-, and/or $\gamma$-secretases, vasoactive intestinal peptide, leptin, acid alpha-glucosidase (GAA), acid sphingomyelinase, iduronate-2-sultatase (I2S), $\alpha$-L-iduronidase (IDU), $\beta$-Hexosaminidase A (HexA), Acid $\beta$-glucocerebrosidase, N-acetylgalactosamine-4-sulfatase, $\alpha$-galactosidase A, and neurotransmitters (see, e.g., Schapira, A. H. (2003) Neurology 61:S56-63; Ferrari et al. (1990) Adv Exp Med Biol. 265:93-99; Ferrari et al. (1991) J Neurosci Res. 30:493-497; Koliatsos et al. (1991) Ann Neurol. 30:831-840; Dogrukol-Ak et al. (2003) Peptides 24:437-444; Amalfitano et al. (2001) Genet Med. 3:132-138; Simonaro et al. (2002) Am J Hum Genet. 71:1413-1419; Muenzer et al. (2002) Acta Paediatr Suppl. 91:98-99; Wraith et al. (2004) J Pediatr. 144:581-588; Wicklow et al. (2004) Am J Med Genet. 127A:158-166; Grabowski (2004) J Pediatr. 144: S15-19; Auclair et al. (2003) Mol Genet Metab. 78:163-174; Przybylska et al. (2004) J Gene Med. 6:85-92). Lysosomal storage diseases are inherited genetic defects that result in an enzyme deficiency, which prevents cells from performing their natural recycling function (Enns and Huhn, (2008) Neurosurg. Focus 24:E12). This leads to a variety of progressive physical and/or mental deterioration and it is believed that delivery of these deficient enzymes to the brain can result in treatment of these diseases. Various enzymes implicated in lysosomal storage diseases or enzymes that can fulfill the function of the deficient enzymes can be delivered using the methods of the present invention.

Reporter proteins and other-non-therapeutic proteins, as well as nucleic acids encoding the proteins, can be delivered to target cells. The reporter protein can be any reporter protein that can be specifically detected when expressed. Suitable reporter proteins include, without limitation, a fluorescent protein (e.g., EGFP, GFP, RFP, BFP, YFP, or dsRED2), an enzyme that produces a detectable product, such as luciferase (e.g., from *Gaussia*, *Renilla*, or *Photinus*), $\beta$-galactosidase, $\beta$-glucuronidase, alkaline phosphatase, and chloramphenicol acetyltransferase gene, or proteins that can be directly detected. Virtually any protein can be directly detected by using, for example, specific antibodies to the protein. Additional markers (and associated antibiotics) that are suitable for either positive or negative selection of eukaryotic cells are disclosed in Sambrook and Russell (2001), *Molecular Cloning*, 3rd Ed., Cold Spring Harbor Laboratory Press, Cold Spring Harbor, N.Y., and Ausubel et al. (1992), *Current Protocols in Molecular Biology*, John Wiley & Sons, including periodic updates.

The nucleic acid to be delivered may also encode a functional RNA. As used herein, the term "functional RNA" refers to an RNA molecule that does not encode a protein and provide a functional activity as an RNA molecule. Examples include, without limitation, RNAi, microRNA, antisense RNA, and ribozymes.

In accordance with another aspect of the instant invention, methods of treating, inhibiting, and/or preventing a disease or a disorder in a subject are provided. In a particular embodiment, the disease or disorder is inflammation. Such diseases include but are not limited to those set forth hereinabove such as inflammatory arthritis, inflammatory bowel diseases, inflammatory vascular diseases, cancer, stroke, TBI, PD and AD, ALS, MS, lysosomal storage diseases, AMD, Prion disease, meningitis, encephalitis, HAD, mental disorders such as depression, autism, and schizophrenia and others. In a particular embodiment, the disease or disorder is a neurodegenerative disease (e.g., AD, PD, Huntington's disease, Lewy body disease, and ALS), particularly Parkinson's disease. In a particular embodiment, the disease or disorder is muscular disease such as, without limitation, a myopathy (e.g., Duchenne muscular dystrophy), neuromuscular dysfunction, soft tissue sarcomas (e.g., muscle tumors), inflammation, and infection. The methods of the instant invention comprise administering at least one cell of the instant invention (or a composition comprising at least one cell) to a subject. The methods may further comprise the administration of at least one other antioxidant, at least one anti-inflammatory, at least one antimicrobial agent, and/or at least one other therapeutic agent to the subject.

For gene therapy, medical workers try to incorporate, into one or more cell types of an organism, a DNA vector capable of directing the synthesis of a protein missing from the cell or useful to the cell or organism when expressed in greater amounts. The methods for introducing DNA to cause a cell to produce a new protein, ribozyme or a greater amount of a protein or ribozyme are called "transfection" methods. See, generally, *Neoplastic Diseases*, Huber and Lazo, eds., New York Academy of Science, New York (1994); Feigner, *Adv. Drug Deliv. Rev.*, 5:163 (1990); McLachlin, et al., *Progr. Nucl. Acids Res. Mol. Biol.*, 38:91 (1990); Karlsson, S. *Blood*, 78:2481 (1991); Einerhand and Valerio, *Curr. Top. Microbiol. Immunol*, 177:217-235 (1992); Makdisi et al., *Prog. Liver Dis.*, 10:1 (1992); Litzinger and Huang, *Biochim. Biophys. Acta*, 11, 13:201 (1992); Morsy et al., *J.A.M.A.*, 270:2338 (1993); Dorudi et al., *British J. Surgery*, 80:566 (1993).

Immune system cells transfected with the nucleic acid such as pre-transfected macrophages of the present invention provide an important advantage for gene delivery systems. For example, these immune-response cells are able to reach virtually inaccessible hypoxic and necrotic tumor tissues that have limited amount of blood microvessels. Traveling throughout these tissues pre-transfected with pro-apoptotic genes macrophages will deliver this genetic material to cancer cells and induce their apoptosis. In addition, macrophages will chase cancer metastases delivering pro-apoptotic genes to them and eventually causing complete eradication of metastases. Thus, one aspect of the invention relates to the treatment of cancer and/or metastases.

Other uses for the gene delivery system of the present invention include, without limitation, treatment of acute inflammatory conditions (e.g., endocarditis), tissue regeneration, artificial organs, adjuvant therapy in organ transplants, organ preservation solutions to decrease cell death from inflammation, generation and transfection of antisense sequences, and delivery of anti-inflammatory cytokines.

In one embodiment, the present invention can be used in tissue engineering. For example, an immune system cell transfected with the nucleic acid can transfer DNA to mesenchymal stem cells (MSCs) in vitro for enhanced mineralization upon transplantation. A standard strategy for bone tissue engineering is the design of 3D polymeric scaffolds, seeding of osteoprogenitor cells on the scaffold, induction of osteogenic differentiation via exogenous recombinant factors, and transplanting of the engineered tissue constructs to bone defect sites in vivo. This strategy suffers various drawbacks for which mineralization potential is major concern. Various cells promote osteogenesis in vivo and it has been shown that macrophages and its precursor cells (monocytes) play a central role by communicating with MSCs to induce mineralization and thus bone formation in vivo (Pollard, Nat Rev Immunol. 9(4):259-70 (2009); Stefater et al., Trends Mol Med. 17(12):743-52 (2011); Guihard et al., Stem Cells 30(4):762-72 (2012); Dong et al., Trends Biotechnol. 31(6):342-6 (2013)). In the present invention the properties of macrophages or monocytes are harnessed by either co-culturing macrophages or monocytes transfected with the nucleic acid, with osteoprogenitor cells (MSCs) before in vivo transplantation or use immunogenic properties of biomaterials to trigger activity of host-macrophage or monocytes transfected with the nucleic acid in situ upon implantation of scaffolds.

In one embodiment, the present invention can be used in the treatment of end stage kidney disease and the inflammation associated therewith. Immune system cells transfected with nucleic acid are particularly useful in treatment of conditions associated with inflammation, including chronic inflammation. For example, chronic inflammation is a common feature of end-stage renal disease (ESRD) that is gaining increasing attention as a major cause of morbidity and mortality. It is well established that ESRD per se carries a heightened risk of inflammatory disorders and other co-morbid conditions, but it should also be pointed out that dialysis treatment per se can bring additional risk factors for inflammation, such as impure dialysate or bio-incompatible membranes. Inflammation has recently been associated with atherosclerosis and malnutrition in ESRD, and this link has led to the development of the malnutrition, inflammation, atherosclerosis (MIA) hypothesis. This describes a syndrome whereby raised levels of pro-inflammatory cytokines (such as IL-1, IL-6 and TNF-$\alpha$) are a common link between malnutrition, inflammation and atherosclerosis. Also, anaemia appears to be an important element linking elevated cytokine levels with poor patient outcomes. Several mechanisms for cytokine-induced anaemia have been proposed, including intestinal bleeding, impaired iron metabolism and suppression of bone marrow erythropoiesis and erythropoietin production. These effects suggest that pro-inflammatory cytokines may also be an important cause of lack of response to recombinant human erythropoietin (rh-Epo) therapy. In the light of this putative role of pro-inflammatory cytokines, anti-cytokine agents may prove useful to optimize efficacy of rh-Epo in anaemic chronic renal failure patients. Other potential therapeutic strategies include minimizing exposure to causes of inflammation from various co-morbid conditions, such as persistent infections and chronic heart failure.

In one embodiment, the present invention can be used in the treatment of septic shock syndrome and the inflammation associated therewith. Tumor necrosis factor (TNF) plays a role in the pathogenesis of septic shock syndrome. Although the regulated release of TNF may exert normal physiologic effects, the uncontrolled production of TNF may lead to organ dysfunction and death. TNF mediates a variety of other physiologic processes that are unrelated to sepsis syndrome. Anti-TNF and anti-inflammatory therapies using immune system cells transfected with the nucleic acid can be used to attenuate the injurious actions of TNF.

In one embodiment, the present invention can be used in the treatment of autoimmune crisis (e.g. lupus) and the inflammation associated therewith. Transforming growth factor beta 1 (TGF-beta 1) deficiency can cause excessive inflammatory response with massive infiltration of lymphocytes and macrophages in many organs, including heart and lungs. This phenotype suggests a prominent role for TGF-beta 1 in homeostatic regulation of immune cell proliferation and extravasation into tissues. Using immune system cells transfected with the nucleic acid such as TGF-beta 1 can be used to attenuate the autoimmune crisis (e.g. lupus).

In one embodiment, the present invention can be used in the treatment of organ rejection and the inflammation associated therewith. Chronic allograft rejection is a complex, immune-mediated process with no causative therapy available and remains the main cause for graft loss after transplantation. Transplant dysfunction due to chronic rejection occurs in up to 50% of patients 3 years after transplantation, and involves general immune reactions elicited by direct and indirect presentation of alloantigens. The allograft rejection is associated with local inflammatory activation in host organs. Immune system cells transfected with the nucleic acid can be used to transfer genes that are aimed to decrease inflammation and mitigate the chronic allograft rejection.

In one embodiment, the present invention can be used in the treatment of inflammation related to organ preservation. The storage conditions of the donor kidney may influence the deleterious consequences of ischemia/reperfusion (IR), which remains a major source of complications in clinical practice. Delayed graft function (DGF), seen in 20% to 50% of transplanted cadaver kidneys, is a major risk factor affecting early and long-term graft survival, patient management, and costs of transplantation. Cold preservation plays a key role in this process and is based on hypothermia and high potassium solutions (Hauet et al., Kidney Int (2008) 74, 998-1003 (2008)). In this review, the authors focused on the major molecular mechanisms of cold storage (CS) injury at the cellular level, which have been recently evidenced with modern biochemical and cell biologic methods. Because the shortage of organs is also a real public health problem, organs from non-heart beating donors or marginal donors are now used to expand the pool of organs. The immune system cells transfected with the nucleic acid of the present invention can be used for development of organ preservation methods.

While the instant invention is described above as delivering a cell to a subject, the instant invention also encompasses delivering a nucleic acid molecule with the amphiphilic block polymer (as described above) in the absence of a cell. In a particular embodiment, the method comprises administering a composition comprising a nucleic acid of the instant invention, an amphiphilic block copolymer, and, optionally, a pharmaceutically acceptable carrier. The amphiphilic block copolymer may be present in a composition with the nucleic acid to be transfected at a concentration of about 0.01% to about 10%, particularly about 0.3% to about 5%, particularly about 0.3% to about 2%. In a particular embodiment, the method further comprises administering the amphiphilic block copolymer (in the absence of the nucleic acid molecule) to the subject prior to the administration of the composition comprising a nucleic acid and the amphiphilic block copolymer. In a particular embodiment, the amphiphilic block copolymer (optionally in a composition with a pharmaceutically acceptable carrier) is administered immediately prior to or at about 5 minutes to about 3 days prior to the administration of the composition comprising a nucleic acid and the amphiphilic block copolymer, particularly between about 30 minutes and 2 days, particularly about 24 hours or about 36 hours. The amphiphilic block copolymer may be present in the composition without the nucleic acid to be transfected at a concentration of about 0.3% to about 10%, particularly about 0.5% to about 5%, particularly about 1% to about 5%. The compositions may be administered to a subject in accordance with the methods for delivering the cells to a subject. The instant invention also encompasses methods of transfecting cells in vitro using the above compositions, wherein the method comprises contacting the cells with the composition.

I. Definitions

The following definitions are provided to facilitate an understanding of the present invention:

The singular forms "a," "an," and "the" include plural referents unless the context clearly dictates otherwise.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

As used herein, the term "lipophilic" refers to the ability to dissolve in lipids.

As used herein, the term "hydrophilic" means the ability to dissolve in water.

As used herein, the term "amphiphilic" means the ability to dissolve in both water and lipids. Typically, an amphiphilic compound comprises a hydrophilic portion and a lipophilic portion.

"Polypeptide" and "protein" are sometimes used interchangeably herein and indicate a molecular chain of amino acids. The term polypeptide encompasses peptides, oligopeptides, and proteins. The terms also include post-expression modifications of the polypeptide, for example, glycosylations, acetylations, phosphorylations and the like. In addition, protein fragments, analogs, mutated or variant proteins, fusion proteins and the like are included within the meaning of polypeptide.

The term "isolated" may refer to protein, nucleic acid, compound, or cell that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimerosal, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., stress related disorder) resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof.

As used herein, the term "subject" refers to an animal, particularly a mammal, particularly a human.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "vector" is a nucleic acid molecule such as a plasmid, cosmid, bacmid, phage, or virus, to which another genetic sequence or element (either DNA or RNA) may be attached so as to bring about the replication of the attached sequence or element. The vector typically comprises an expression operons.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "antimicrobials" as used herein indicates a substance that kills or inhibits the growth of microorganisms such as bacteria, fungi, viruses, or protozoans.

As used herein the term "antibiotic" refers to a molecule that inhibits bacterial growth or pathogenesis. Antibiotics include, without limitation, β-lactams (e.g., penicillins and cephalosporins), vancomycins, bacitracins, macrolides (e.g., erythromycins, clarithromycin, azithromycin), lincosamides (e.g., clindomycin), chloramphenicols, tetracyclines (e.g., immunocycline, chlortetracycline, oxytetracycline, demeclocycline, methacycline, doxycycline and minocycline), aminoglycosides (e.g., gentamicins, amikacins, neomycins, amikacin, streptomycin, kanamycin), amphotericins, cefazolins, clindamycins, mupirocins, sulfonamides and trimethoprim, rifampicins, metronidazoles, quinolones, fluoroquinolones (e.g., ciprofloxacin, levofloxacin, moxifloxacin), novobiocins, polymixins, gramicidins, vancomycin, imipenem, meropenem, cefoperazone, cefepime, penicillin, nafcillin, linezolid, aztreonam, piperacillin, tazobactam, ampicillin, sulbactam, clindamycin, metronidazole, levofloxacin, a carbapenem, linezolid, rifamycins (e.g., rifampin, rifabutin), clofazimine, and metronidazole.

As used herein, the term "antiviral" refers to a substance that destroys a virus or suppresses replication (reproduction) of the virus.

II. Administration

The cells described herein will generally be administered to a patient as a pharmaceutical preparation. The term "patient" as used herein refers to human or animal subjects. These cells may be employed therapeutically, under the guidance of a physician.

The pharmaceutical preparation comprising the cells of the invention may be conveniently formulated for administration with any pharmaceutically acceptable carrier. For example, the cells may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the cells in the chosen medium may be varied and the medium may be chosen based on the desired route of administration of the pharmaceutical preparation. Except insofar as any conventional media or agent is incompatible with the cells to be administered, its use in the pharmaceutical preparation is contemplated.

The dose and dosage regimen of cells according to the invention that are suitable for administration to a particular patient may be determined by a physician considering the patient's age, sex, weight, general medical condition, and the specific condition for which the cells are being administered and the severity thereof. The physician may also take into account the route of administration, the pharmaceutical carrier, and the cell's biological activity.

Selection of a suitable pharmaceutical preparation will also depend upon the mode of administration chosen. For example, the cell of the invention may be administered by direct injection into an area proximal to the blood brain barrier. In this instance, a pharmaceutical preparation comprises the cells dispersed in a medium that is compatible with the site of injection.

Cells of the instant invention may be administered by any method such as intravenous injection into the blood stream, oral administration, or by subcutaneous, intramuscular or intraperitoneal injection. Pharmaceutical preparations for injection are known in the art. If injection is selected as a method for administering the cells, steps must be taken to ensure that sufficient amounts of the cells reach their target cells to exert a biological effect.

Pharmaceutical compositions containing a cell of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of cells may be determined by evaluating the toxicity of the molecules or cells in animal models. Various concentrations of cells in pharmaceutical preparations may be administered to mice, and the minimal and maximal dosages may be determined based on the beneficial results and side effects observed as a result of the treatment. Appropriate dosage unit may also be determined by assessing the efficacy of the cell treatment in combination with other standard drugs. The dosage units of cells may be determined individually or in combination with each treatment according to the effect detected.

The pharmaceutical preparation comprising the cells may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The following examples provide illustrative methods of practicing the instant invention, and are not intended to limit the scope of the invention in any way.

EXAMPLE 1

Materials and Methods
Plasmids

The gWIZ™ high expression vectors encoding the reporter genes luciferase (gWIZ™Luc) and green fluorescent protein (GFP) (gWIZ™GFP) both under control of an optimized human cytomegalovirus (CMV) promoter followed by intron A from the CMV immediate-early (IE) gene were used throughout the study (Gene Therapy Systems, San Diego, Calif.). The expression vector encoding tomato protein reporter gene was purchased from Clonetech Laboratories Inc. (Mountain View, Calif.). Human catalase pDNA ORF clone (GenBank Accession No. NM_001752) was obtained from OriGene (Rockville, Md.). All plasmids are expanded in DH5a $E.$ $coli$ and isolated using Qiagen endotoxin-free plasmid Gina-prep kits (Qiagen, Valencia, Calif.) according to the protocol.

Reagents

GenePORTER® 30000 transfection agent was purchased from AMS Biotechnology (England). LPS, 6-OHDA, and Triton X-100 were obtained from Sigma-Aldrich (St. Louis, Mo., USA). Alexa Fluor-678-conjugated anti-CD11b was purchased from BD Biosciences (San Diego, Calif.). Rabbit polyclonal anti-GFP antibodies (A6455), secondary chicken anti-rabbit HRP-conjugated antibodies (A829), and antibodies to human catalase (A16772-100) were obtained from Abcam (Cambridge, Mass.). Anti-NeuN Antibodies were purchased from EMD Millipore, (Billerica, Mass.). CD63 and NFκB P65 monoclonal antibodies were obtained from Santa Cruz Biotechnology (Santa Cruz, Calif.). A luminescent substrate, D-Luciferase, was purchased in Caliper Life Sciences (Hopkinton, Mass.). A nucleic acid stain, YOYO-1 iodide (491/509), was obtained from Invitrogen (Carlsbad, Calif.).

Cells

A mouse macrophage cell line (RAW 264.7) was purchased from ATCC (cat #TIB-71), and cultured in Dulbecco's Modified Eagle's Media (DMEM) (Invitrogen, Carlsbad, Calif., USA) supplemented with 10% FBS. Mouse catecholaminergic Cath.A neurons were purchased from American Type Culture Collection (American Type Culture Collection, ATCC, Manassas, Va., USA), and cultured in RPMI-1640 medium supplemented with 8% normal horse serum (NHS), 4% fetal bovine serum (FBS), and 1% penicillin-streptomycin. Cath.A neurons were differentiated by adding 1 mM of N6,2'-O-dibutyryladenosine 3',5'-cyclic monophosphate sodium salt (dbcAMP, St. Louis, Mo., USA) (Rosenbaugh et al. (2010) Biomaterials 31:5218-5226).

Animals

This study was carried out in strict accordance with the recommendations in the Guide for the Care and Use of Laboratory Animals of the National Institutes of Health. The protocol was approved by the Committee on the Ethics of Animal Experiments of the University of Nebraska Medical Center (Permit Number: 05-087-12). All surgery was performed under sodium pentobarbital anesthesia, and all efforts were made to minimize suffering. Balb/c male mice (Charles River Laboratories, USA) eight weeks of age were used in the in vivo IVIS experiments to reduce fluorescence quenching by colored skin and fur. The animals were kept five per cage with an air filter cover under light- (12-hours light/dark cycle) and temperature-controlled (22±1° C.) environment. All manipulations with the animals were performed under a sterilized laminar hood. Food and water were given ad libitum.

Transfection of Macrophages: Protein Expression and Release

RAW 264.7 macrophages were incubated with a mixture of 2 µg/ml GFP, or catalase, or luciferase, or tomato protein pDNA and GenePORTER® 3000 for four hours. Following incubation, the cells were washed with PBS, cultured for various time points (up to 21 days) in complete media with 20% FBS, and then GFP expression was accounted by fluorescence activated cell sorting. Next, the same conditions were used for macrophages transfection with catalase, or luciferase, or tomato protein pDNA under the control of CMV promoter.

For measures of the overexpressed protein release, culture media from transfected macrophages was collected at various time points, and assessed for amount of fluorescence for GFP-transfected macrophages (Shimadzu RF5000 fluorescent spectrophotometer; λex=488 nm, λem=501 nm), or catalase enzymatic activity in case of transfection with catalase pDNA using Amplex Red assay as described (Batrakova et al. (2007) Bioconjug. Chem., 1$:1498-1506). Briefly, media samples from transfected macrophages were supplemented with Amplex® Red Dye stock solution (10 U/mL HRP, 10 mM Ampex® Red) for 30 minute, and ROS content was measured by fluorescence at λex=563 nm, λem=587 nm according to the manufacturer's specifications. Amount of the expressed enzyme was normalized for protein content and expressed in U of catalase per mg of the protein as means±SEM (N=4). To exclude the possibility that cell death explains the release of catalase and GFP, percentage of live macrophages on the fourth day after transfection was accounted by FACS. For this purpose, transfected cells were collected, washed, stained with Alexa Fluor® 488 LIVE/DEAD dye according to manufacturer's protocol, and the amount of accumulated dye was assessed (N=4). The mean±standard deviation was less than 10%.

Isolation of Exosomes

RAW 264.7 macrophages grown on 75T flasks (20×10$^6$ cells/flask) were transfected with GFP, catalase, or tomato protein pDNA as described above, washed three times with PBS, and fresh media was added to the cells. Following 48 hours, cellular media was collected, filtered through 20 µM filter to eliminate cellular debris, and exosomes were isolated using Exoquick™ Exosome Precipitation Solution (System Biosciences, Mountain View, Calif.). The obtained exosomal fraction was re-suspended in PBS (500 ml, 1 mg/ml total protein), and evaluated for protein and genetic material content. In separate experiments, exosomes isolated from tomato protein-transfected macrophages were added to Cath.A neurons and dynamics of pDNA accumulation and the encoded protein expression in target cells were visualized by confocal microscopy.

Atomic Force Microscopy (AFM)

Exosomes from catalase-transfected or non-transfected macrophages were isolated, and the obtained exosomal fraction at total protein 1 mg/ml was diluted 100 times in PBS. A drop of the sample was placed on positively charged mica treated with 1-(3-aminopropyl) silatrane (APS) (Lyubchenko et al. (2009) Methods Mol. Biol., 543:337-351) for 2 minutes, washed with deionized water, and dried under an argon flow. The AFM imaging was operated as described [17]. Image processing and the cross-section analysis were performed using Femtoscan (Advanced Technologies Center, Moscow, Russia). The height of the particles and their diameters measured at half-maximal height were obtained from the cross-section analysis. The volume was approximated by a hemisphere using the equation (Henderson et al. (1996) Proc. Natl. Acad. Sci., 93:8756-8760). A standard t-test was performed for the size comparison of exosomes released from catalase-transfected and non-transfected macrophages.

Western Blot Analysis

Western blot technique was applied to examine protein content of exosomes secreted from GFP- or empty vector-transfected RAW 264.7 macrophages, in particular, the presence of GFP and transcription factor, NF-κB. Protein concentrations were determined using NanoDrop 2000 (Nano Drop Products, Wilmington, Del.). Primary rabbit polyclonal antibodies to GFAP were used at 1:1,000 dilution. Secondary chicken anti-rabbit HRP-conjugated antibodies were used in 1:4,000 dilution. NF-κB P65 monoclonal antibodies were used at 1:50,000 dilution. Specific protein bands were visualized by Immobilon™ Western Chemiluminescent HRP Substrate kit (Millipore, Billerica, Mass.), and quantitated by densitometry (Bio-Rad Laboratories, Hercules, Calif.) (Batrakova et al. (2007) Bioconjug. Chem., 18:1498-1506). To correct for loading differences in exosomal fractions, the levels of proteins were normalized to CD63 that is constitutively expressed in exosomes.

PCR and RT-PCR Analyses cDNA synthesis: Exosomes were diluted to 1 μg/mL of protein, lysed, treated with DNase and reverse transcribed using SuperScript™ III CellsDirect cDNA Synthesis System according to manufacturer's protocol. For DNA samples exosomes were lysed and treated with RNase to prepare them for PCR. Polymerase Chain Reaction: PCR was performed using GFP primers (the forward sequence was 5-TCTGGGACACAAATTGGAATACAACT-3 (SEQ ID NO: 1) and reverse sequence was 5-CGGGTCTTGAAGT-TCACTTTGATTC-3 (SEQ ID NO: 2)) using Platinum® Taq DNA Polymerase (Invitrogen). Final concentrations of reagents were as follows: 1× PCR buffer, 0.2 mM dNTP mixture, 1.5 mM $MgCl_2$ 0.2 μM forward primer, 0.2 μM reverse primer and 2 U DNA polymerase in distilled water. 4% cDNA or RNase treated lysate was added. The reaction mixture was incubated in a thermocycler for 30 seconds at 94° C., then 35 cycles of denaturing (94° for 15-30 seconds), annealing (59° C. for 30 seconds), and extension (72° C. for 1 minute) were performed. DNA was subjected to agarose gel electrophoresis (1% agarose at 60 V for 90 minutes) and subsequent ethidium bromide staining (0.5 μg/mL Ethidium bromide in 1× TAE), and imaged with Bio-Rad Gel Doc™ instrument. Real Time PCR: 40 mL DEPC treated water was used to dilute cDNA and DNA obtained as described above. 3 μL of this dilution was analyzed by real-time PCR. The real-time PCR reaction was carried out using TaqMan® Gene Expression Master Mix and Expression Assays (Mouse GAPDH (The forward primer was 5-TCACTG-GCATGGCCTTCC-3 (SEQ ID NO: 3), the reverse sequence was 5-GGCGGCACGTCAGATCC-3 (SEQ ID NO: 4), and the TAMRA™ probe sequence was 5-TTC-CTACCCCCAATGTGTCCGTCG-3 (SEQ ID NO: 5)) and custom eGFP primers (ABI Assay ID:AIWR2DN)) using manufacturer protocols on an ABI 7700 Sequence Detector System (Applied Biosystems). Results were analyzed using the ΔΔCt method.

Production of a Lentiviral Vector (LV)

Lentiviral vectors encoding a fusion between GFP and firefly luciferase (FLuc) were created by PCR amplifying the cDNA sequences for GFP and FLuc from pEGFP (Clontech) and pcDNA-Luciferase (Addgene) with restriction enzyme sequences that were engineered into the primers. To create the final constructs, GFP was digested with BamHI/EcoV and FLuc was digested with EcoV/XhoI. The digested fragments were ligated into the BamHI/XhoI digested pTK402 LV transfer vector. LV-GFPFLuc viral vectors were packaged in 293T by transient transfection using the psPAX2 and pMD2.G (Addgene) packaging plasmids (Sena-Esteves et al. (2004) J. Virol. Methods 122:131-139).

Confocal Microscopy Studies

GFP expression in RAW 264.7 macrophages was visualized by a confocal fluorescence microscopic system ACAS-570 (Meridian Instruments, Ohms, Mich.) with argon ion laser (excitation wavelength, 488 nm) and corresponding filter set. Digital images were obtained using the CCD camera (Photometrics) and Adobe Photoshop software. To visualize catalase expression, transfected with catalase pDNA macrophages were fixed with 4% paraformaldehyde (PFA) for 15 minutes, treated with 0.4% Triton for 4 minutes, and then stained with primary mouse antibodies to human catalase, and Alexa Fluor® 488-conjugated secondary goat anti mouse antibodies (1:200 Dilution, Invitrogen, Carlsbad, Calif., USA). Nonspecific interactions were blocked with 3% BSA for 30 minutes prior the staining with antibodies. To examine accumulation of exosomes secreted from macrophages in neuronal cells, RAW 264.7 macrophages ($20 \times 10^6$ cells/flask) were cultured for three days in DMEM supplemented with 10% FBS, and then concomitant media was collected, exosomes were isolated with Exo-Quick™ Exosome Kit according to manufacturer's protocol, and labeled with lipophilic fluorescent dye, 3,3'-dilinoleyl-oxacarbocyanine perchlorate (DIO) (Haney et al. (2012) Nanomedicine 7:815-833). Then, Cath.A neurons grown on chamber slides ($1 \times 10^5$ cells/chamber) (Batrakova et al. (2005) Bioconjug. Chem., 16:793-802) were supplemented with the DIO-labeled exosomes (1 mg of total protein/100 μl) and incubated for another 24 hours. Neurons were stained with Anti-NeuN Antibodies (blue) prior to the imaging.

To visualize genetic material and the encoded protein transfer from exosomes to neurons, pDNA encoded tomato protein was labeled with a fluorescent dye YOYO-1 (green) prior to macrophages transfection. Then, RAW 264.7 macrophages were transfected with YOYO-1 labeled pDNA encoded tomato protein, and cultured in DMEM media. To visualize genetic material transfer from exosomes to neurons, the media from the tomato protein-transfected macrophages was collected, the exosomes (0.5 mg/ml) were isolated and added to Cath.A neurons grown on chamber slides ($1 \times 10^5$ cells/chamber). Confocal images of the neurons accumulating YOYO-labeled DNA (green) and expressing tomato protein (red) were taken at different times with corresponding laser and filter sets. Neurons were fixed and stained with Anti-NeuN Antibodies (blue) prior to the imaging.

To study macrophage-mediated gene transfer in vivo, mice with brain inflammation induced were i.v. injected with GFP-transfected macrophages ($5\times10^6$ cells/mouse in 100 μl PBS) on day four after transfection. In the control experiment, mice with brain inflammation were i.v. injected with LV-GFPFLuc virus ($2\times10^4$ particles/100 μl/mouse). One and five days later, animals were sacrificed and perfused as described (Zhao et al. (2011) J. Nanomed. Nanotechnol., S4), main organs (brain, liver, spleen, and lymph nodes) were removed, washed, post-fixed in 10% phosphate-buffered paraformaldehyde, and evaluated by confocal microscopy. Healthy mice (without brain inflammation) were used as controls.

Fluorescence Activated Cell Sorting (FACS)

Number of GFP-transfected macrophages and the expression levels (in relative fluorescent units (RFU)) were assessed by FACS. Typically, RAW 264.7 macrophages transfected with GFP pDNA/GenePORTER® 3000 reagent were cultured in DMEM complete media for various times, then the cells were detached, collected and the amount of the expressed GFP was accounted by FACS.

To evaluate kinetics of GFP transfer from the transfected macrophages to Cath.A neurons, GFP-transfected RAW 264.7 macrophages ($1\times10^6$ cells/sample) were cultured for four days in DMEM media supplemented with 20% FBS, and then added to Cath.A neurons ($1\times10^6$ cells/sample, 1:1 ratio). The co-cultured cell mixture was collected at different time points and the amount of GFP in macrophages and neurons was assessed by FACS. To distinguish between the cell types, macrophages were labeled with Alexa 678-conjugated antibodies to CD 11b prior to the assessment. The expression levels GFP levels were plotted vs. time of co-culture.

Induction of Brain Inflammation in Mice

For 6-OHDA and LPS intoxications, mice were stereotactically injected into substantia nigra pars compacta (SNpc) with 6-OHDA solution (10 μg 6-OHDA in 0.9% NaCl with 0.02% ascorbic acid), or LPS solution (10 μg LPS in 0.9% NaCl with 0.02% ascorbic acid), respectively, flow rate of 0.1 mL/min into the striatum (AP: +0.5; L: 22.0 and DV: 23.0 mm) (Zhao et al. (2011) J. Nanomed. Nanotechnol., S4). Three or four weeks after 6-OHDA intoxication, or 24 hours after LPS intoxication, the animals were injected via the intrajugular vein (i.v.) with GFP2, or luciferase-, or catalase-transfected macrophages ($5\times10^6$ cells/mouse in 100 μl PBS).

Bioimaging and Infrared Spectroscopy (IVIS)

To reduce fluorescence quenching by fur, Balb/c mice were shaved prior to the imaging. Luciferase-transfected macrophages were i.v. injected on day 3 after transfection to 6-OHDAintoxicated mice ($5\times10^6$ cells/mouse in 100 μl PBS) on day 21 after the intoxication. A solution of bioluminescent substrate, D-Luciferin, was injected intraperitoneally (i.p.) (100 μl/mouse) before the cell adoptive transfer. Healthy animals without brain inflammation were used in the control group (N=4). In another neuroinflammation model, LPS-intoxicated mice were i.v. injected with catalase-transfected macrophages on day four after transfection. Ten minutes before imaging, each animal received an i.p. injection of XenoLight™ RediJect Inflammation probe, a chemiluminescent reagent for monitoring inflammation (Caliper, Hopkinton, Mass.). This probe is offered in a ready-to-use format and can be conveniently applied to study myeloperoxydase (MPO) activity of activated phagocytes. The animals were imaged at various time points (15 minutes-40 days) post-treatment as described (Brynskikh et al. (2010) Nanomedicine 5: 379-396). The chemiluminescent signal was quantified by living imageH 2.50 software and presented as radiance ratio of treated animal vs. 24 hours after LPS injection.

Immunohistochemical and Stereological Analyses

6-OHDA-intoxicated mice were i.v. injected with PBS, or catalase-transfected macrophages, or macrophages transfected with empty vector ($5\times10^6$ cells/mouse/100 μl) 48 hours after the intoxication. Healthy non-intoxicated animals i.c. injected with PBS instead of 6-OHDA were used in two control groups that were i.v. injected with PBS or empty-transfected macrophages (N=7) 48 hours after PBS i.c. injections. Four weeks later, animals were sacrificed, perfused; brains were removed, washed, postfixed, and immunohistochemical analysis was performed in 30 μm thick consecutive coronal brain sections (Brynskikh et al. (2010) Nanomedicine 5: 379-396). For detection of microglia activation, tissue sections were incubated with primary monoclonal rat anti-mouse anti-CD11b antibodies (1:500 dilution), and secondary biotinylated goat anti-rat antibodies (Vector Laboratories, Burlingame, Calif., 1:200 dilution). For the assessment of neuroprotection effect, a tyrosine hydroxylase (TH) staining was used to quantitate numbers of dopaminergic neurons (DA) (Tieu et al. (2003) J. Clin. Invest., 112:892-901). The total number of TH-positive DA neurons and CD11b-positive microglia cells were counted by using the optical fractionators module in StereoInvestigator software (MicroBrightField, Inc., Williston, Vt.) (Brynskikh et al. (2010) Nanomedicine 5: 379-396).

Behavioral Tests

For the traditional constant speed rotarod test, mice were trained and tested as described (Rozas et al. (1997) Braiu Res. Brain Res. Protoc., 2:75-84) with slight modifications. 6-OHDA-intoxicated mice (N=10) were i.v. injected with PBS, or catalase-transfected macrophages, or empty-transfected (with GFP-encoded pDNA) macrophages 48 hours after intoxication and the latency to fall from the rotarod was determined at three speeds (4, 5, and 7 rpm) on day 28 after intoxication. Healthy mice with PBS i.c. injections were used as a control (Keshet et al. (2007) J. Comp. Neurol., 504:690-701). For apomorphine test, the four groups of mice (i.c. PBS/i.v. PBS; i.c. 6-OHDA/i.v. PBS, i.c. 6-OHDA/i.v. catalase transfected macrophages, and i.c. 6-OHDA/i.v. empty-transfected macrophages) were injected with apomorphine (0.05 mg/kg, s.c.) on day 28 after intoxication, and rotations were scored every 10 minutes for 90 minutes (Papathanou et al. (2011) Eur. J. Neurosci., 33:2247-2254).

Statistical Analysis

For the all experiments, data are presented as the mean±SEM. Tests for significant differences between the groups in in vitro experiments investigating transfection of macrophages, as well as in in vivo evaluations of therapeutic effects of different drug formulations were performed using a one-way ANOVA with multiple comparisons (Fisher's pairwise comparisons) using GraphPad Prism 5.0 (GraphPad software, San Diego, Calif.). A standard t-test was performed when only two groups were compared (for example, for size evaluation of exosomes released from transfected and non-transfected macrophages). A minimum p value of 0.05 was chosen as the significance level for all tests.

Results

Transfection of the Cell-Carriers with Reporter and Therapeutic Proteins

Efficient transfection of cell-carriers is important for their use as drug and gene delivery vehicles. Therefore, at first, the optimal conditions for macrophage transfection (exposure time, DNA and transfection reagent ratios) were determined. Statistically significant increases in the expression of reporter green fluorescent protein (GFP), and catalase were found (FIG. 1). The best results were obtained, when macrophages were transfected using GenePORTER® 3000 transfection agent incubated with 2 µg/ml pDNA encoded GFP, or catalase for four hours, and cultured in complete media with 20% FBS. Up to 40% of cells expressed GFP with maximal gene expression by day 4 was detected by FACS (FIG. 1, Panel A) and confocal microscopy (FIG. 1, Panel C). A sustained protein expression and prolonged release into the media for at least 21 days was detected by GFP fluorescence, or catalase enzyme activity (FIG. 1, Panel B), and confirmed by confocal microscopy in catalase-transfected macrophages (FIG. 1, Panel D). The peak of the GFP fluorescence in macrophages at day 4 was followed by the sharp decreases in the expression levels and number of the transfected cells indicating relatively transient transfection of macrophages with GenePORTER® 3000. Notably, 95.7% of transfected macrophages releasing the encoded protein were alive on day four as confirmed by FACS. This excludes the possibility that the release of catalase and GFP into concomitant media could be a result of cell death.

Figure 2:
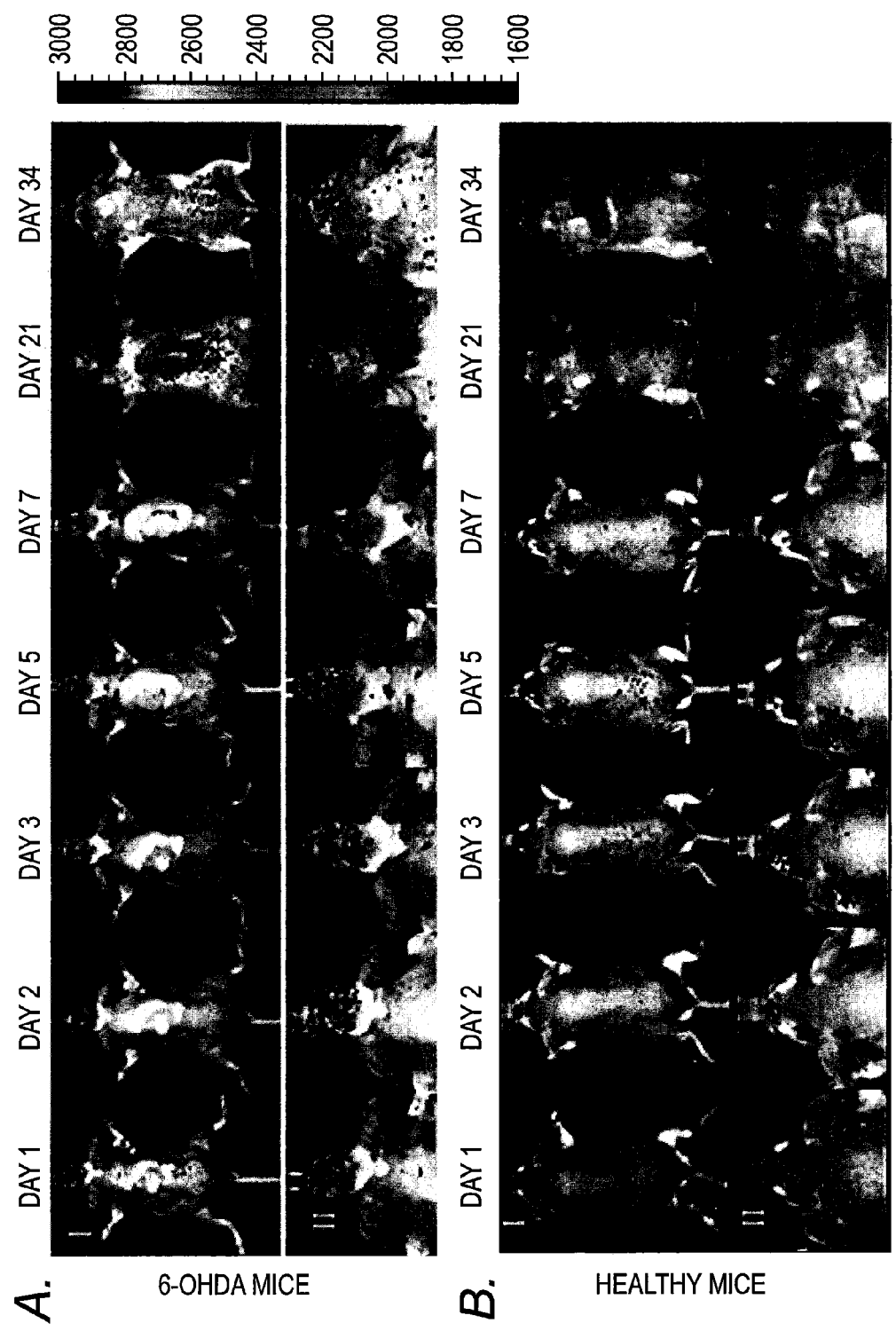
FIG. 2 shows the transfection of brain tissues by genetically-modified macrophages in murine models of PD. Balb/C mice were i.c. injected into substantia nigra pars compacta, SNpc with 6-OHDA (Panel A), or with PBS (Panel B). Twenty one days after injections, mice were i.v. injected with luciferase transfected macrophages. IVIS representative images from N=4 mice per group demonstrate prolonged expression of luciferase in the brain (Panel A), which peaked at days 3-5 after adoptive cell transfer. Stable luciferase expression levels were attained over a month, suggesting that along with the delivered luciferase, recorded luminescence may originate from the transfected brain tissues. In contrast, low, if any, luminescence was detected in the healthy animals (Panel B). I: whole body images, II: images of mouse head for corresponding time. Panel C: Sections of midbrain (both hemispheres), spleen, lymph nodes and liver of Balb/C mice i.c. injected with LPS into SNpc, and then i.v. injected GFP-transfected macrophages (24 hour following intoxication). Brain sections obtained after 24 hours after transfer (left column) show GFP-expressing macrophages in the ipsilateral hemisphere, spleen, lymph node. No fluorescence was detected in the liver, as well as in the contralateral brain hemisphere. Notably, substantial fluorescence throughout the whole brain was demonstrated five days after macrophages administration (right column) indicating that genetically-modified macrophages transfected ipsilateral brain tissues with inflammation. The bar: 20 µm.
Figure 2:
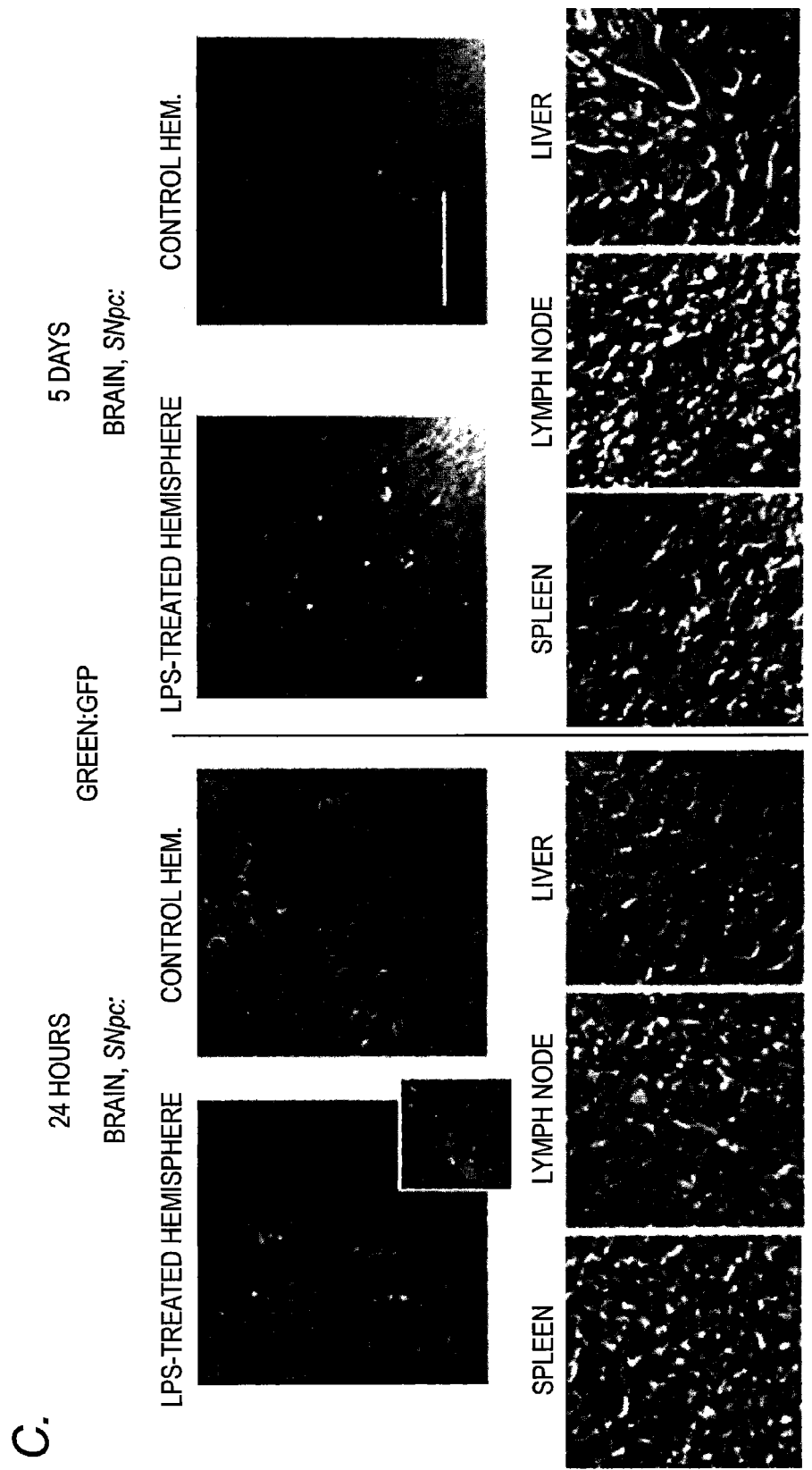

Biodistribution of Systemically Administered Macrophages in Mice and Transfection of the Inflamed Brain Tissues Macrophages can carry and release their "payload" to distal sites of inflammation in various disease conditions (Brynskikh et al. (2010) Nanomedicine 5:379-396; Haney et al. (2012) Nanomedicine 7:815-833; Biju et al. (2010) Mol. Ther. 18:1536-1544; Balkundi et al. (2011) Int. J. Nanomedicine 6:3393-3404). Injected intravenously fluorescently-labeled bone marrow derived macrophages can cross the BBB and deliver nanoparticles with therapeutically active enzyme to the inflamed brain tissues (Brynskikh et al. (2010) Nanomedicine 5:379-396). Here, two in vivo models were used, characterized by ongoing brain inflammation caused by 6-OHDA or LPS intracranial injections into substantia nigra pars compacta (SNpc). First, to examine whether genetically-modified macrophages can reach the brain and deliver their payload, image visualization and infrared spectroscopy studies (IVIS) were conducted 6-OHDA intoxicated mice. Since luminescence is less quenched by bones and tissues than fluorescence, the macrophages were first transfected ex vivo with luciferase pDNA, cultured in complete media for 3 days, and then i.v. injected to the mice ($5 \times 10^6$ cells/100 µl) with or without brain inflammation. In this animal model, the inflammation reaches maximum around the day 21 after intoxication. Therefore, this time point was also used as the day of transfected macrophages administration. The luminescent IVIS images of dorsal planes of the injected animals revealed striking differences in luciferase levels in mice with brain inflammation (FIG. 2, Panel A) compared to healthy PBS-injected animals (FIG. 2, Panel B). Thus, significant luminescence with maximum levels by days 3 to 5 after adoptive cell transfer was detected in the brain of 6-OHDA-intoxicated mice. In contrast, low, if any, luminescence was detected in PBS-treated animals injected with luciferase transfected macrophages. No luminescence was detected in another control group of 6-OHDA-intoxicated animals with systemically administered empty vector-transfected macrophages.

Figure 2D:
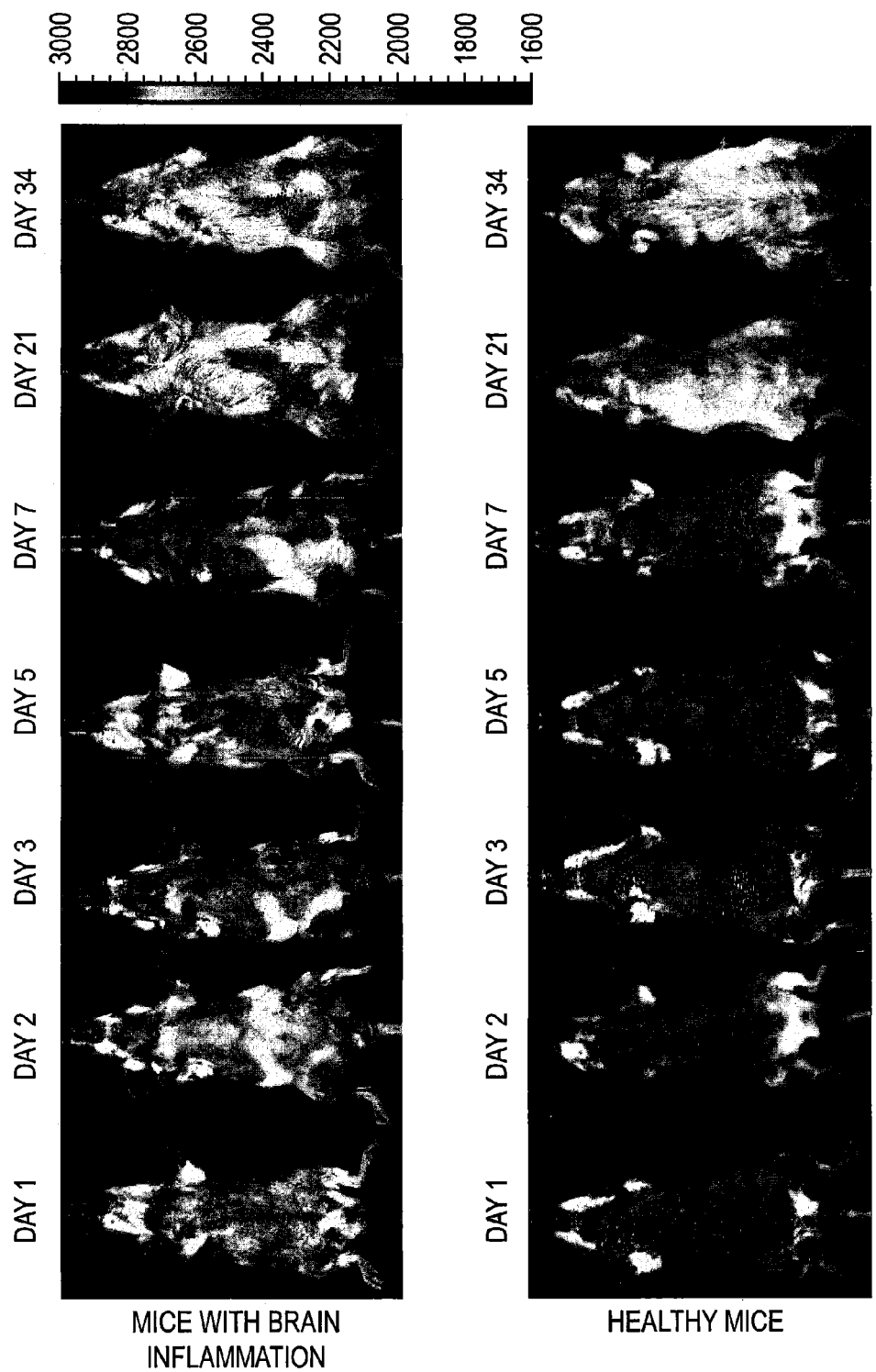
FIG. 2D shows the biodistribution of expressed luciferase in mice with brain inflammation by IVIS. Balb/C mice were i.c. injected with 6-OHDA (0.5 mg/kg) into the substantia nigra pars compacta, SNpc. In parallel, RAW 264.7 macrophages were transfected with luciferase pDNA formulated with GeneP-orter® 3000 transfection agent, cultured in complete media for three days, and then administered through i.v. ($5\times10^6$ cells/100 µl) into the mice with brain inflammation following 21 days after 6-OHDA administration (top). Healthy mice were used as controls (bottom). Representative images from N=4 mice per group (ventral planes) taken at various time points revealed no luminescence in the brain in both mice with brain inflammation as well as healthy animals. No luminescence was detected in peritoneal area, liver, or spleen in mice with brain inflammation.

Furthermore, macrophages that were labeled by ALEXA Fluor® 780 fluorescent dye and systemically injected to 6-OHDA intoxicated mice were not detectable in the brain area after day 18 following administration (Zhao et al. (2011) J. Nanomed. Nanotechnol., S4). In contrast, the obtained IVIS images (FIG. 2, Panel A) demonstrated prolonged (over a month after adoptive transfer) luciferase expression in the inflamed brain. In addition to transfected macrophages, luminescence may, therefore, originate from the transfected brain tissues. Notably, both dorsal (FIG. 2, Panel A) and ventral (FIG. 2D) images of mice with brain inflammation revealed no luciferase expression in peripheral organs, liver, kidney, or spleen indicating active targeting of genetically-modified macrophages specifically to the sites of inflammation.

Figure 2E:
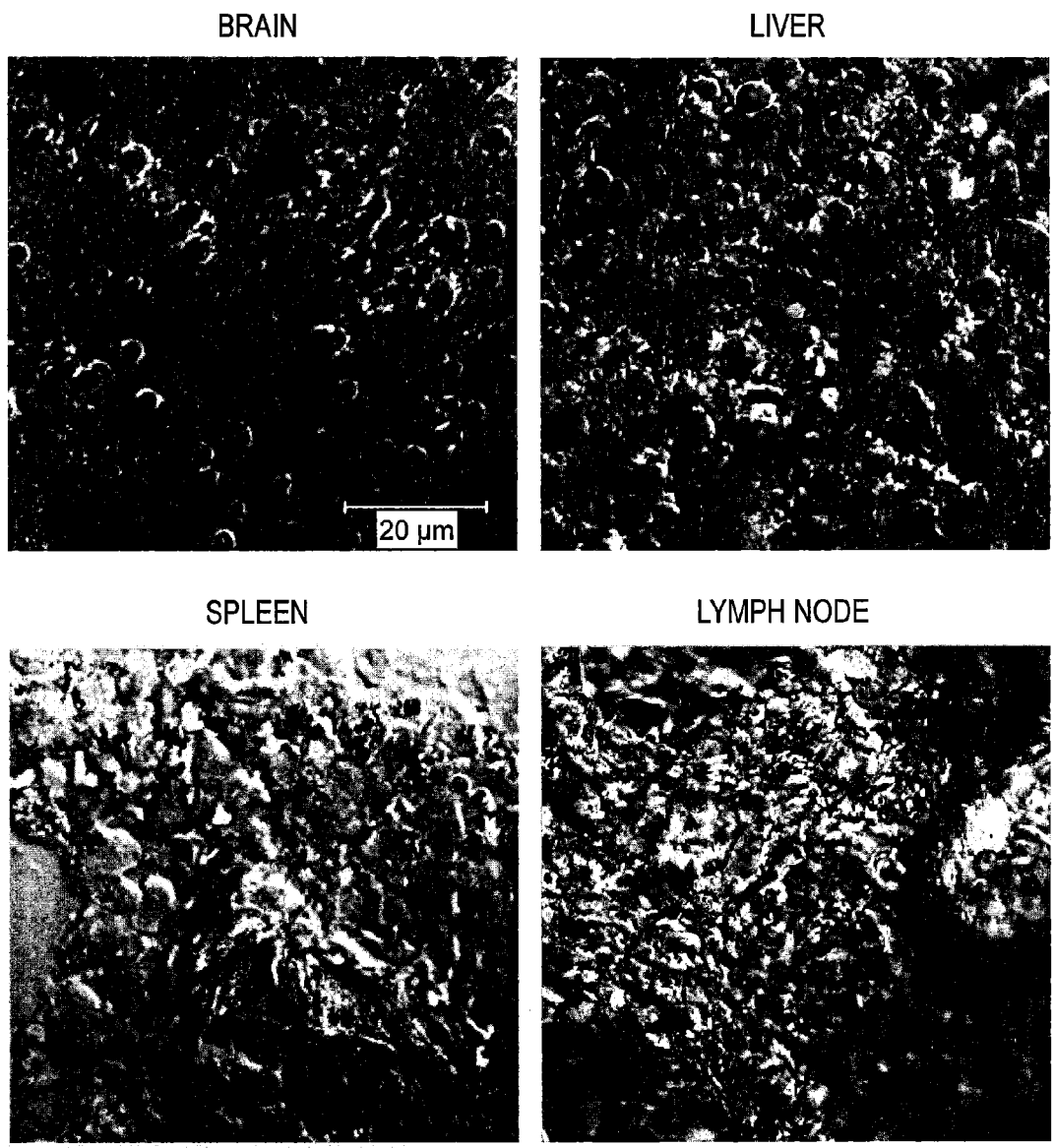
FIG. 2E shows the tracking of GFP-transfected macrophages in healthy mice. RAW 264.7 macrophages were transfected with GFP pDNA formulated with GenePorter® 3000 transfection agent, cultured in complete media for 3 days, and then administered through intrajugular vein ($5\times10^6$ cells/100 µl/mouse) into the mice with brain inflammation following 24 hours after LPS administration. 24 hours later mice were sacrificed and perfused with PBS and 4% PFA. Brain, spleen, and lymph nodes were frozen; tissue specimens were sectioned with a cryostate (10 µm thick) and examined by confocal microscopy (60× magnification). Representative images from N=4 animals demonstrate low, but detectable amounts of BMM in the liver, spleen, and lymph node. No macrophages were found in the healthy brain. The bar: 20 µm.

IVIS imaging of live animals does not allow distinguishing between expressed protein in the blood stream or brain parenchyma. To eliminate this factor, tissue sections of brain and other organs of interest were prepared from mice with neuroinflammation (LPS i.c. injections) that were injected with GFP-transfected macrophages ($5 \times 10^6$ cells/100 µl/mouse) (FIG. 2, Panel C) one and five days following macrophages transfer. The confocal images revealed significant GFP levels by day 1 post transfer in the lesioned brain hemisphere, spleen, lymph node, and low, if any, fluorescence in liver. No GFP expression was found in control (non-injected) hemisphere of the intoxicated animals. At day 5, in addition to GFP expressing macrophages, significant fluorescence throughout the whole brain slides was detected indicating that genetically-modified macrophages transfected brain tissues with inflammation. Healthy mice (without brain inflammation) yielded no GFP expression within the whole brain and much lesser levels in liver, spleen, and lymph nodes (FIG. 2E). Together these data provide evidence that transfected macrophages achieved targeted drug delivery to inflammation sites increasing expression of the desired protein in the brain, but not in other peripheral tissues known to be sites amenable for macrophage migration.

Catalase-Transfected Macrophages Reduce Neuroinflammation in PD Mouse Models

Figure 3:
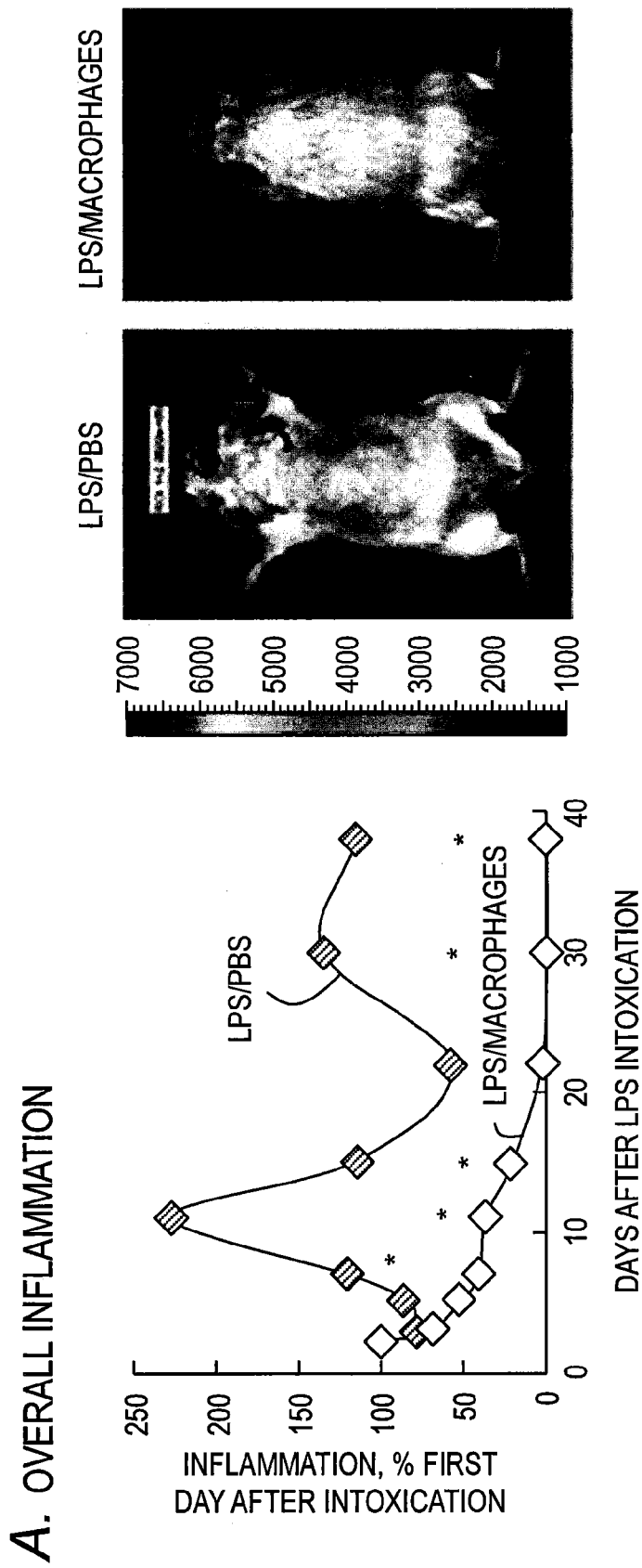
FIG. 3 shows the anti-inflammatory and neuroprotective effects of catalase-transfected macrophages in PD murine models. Panel A: LPS-induced encephalitis in BALB/C mice were injected i.v. with catalase-transfected macrophages or PBS. IVIS images over 40 days were taken ten minutes after intraperitoneal (i.p.) injection of a Xeno-Light™ RediJect probe for inflammation. The chemiluminescent signal was quantified and presented as radiance ratios of treated animal after 24 hours after LPS injection and at various times thereafter. Genetically-modified macrophages caused prolonged decreases of neuroinflammation in LPS-intoxicated mice. IVIS representative images at day 30 are shown. Panels B and C: BALB/c mice were i.c. injected with 6-OHDA. Forty eight hours later animals were i.v. injected with catalase-transfected macrophages, and 21 days later they were sacrificed, and mid-brain slides were stained for expression of CD11b (Panel B), a marker for activated microglia, or TH (Panel C), a marker for dopaminergic neurons. Whereas 6-OHDA treatment caused significant microglia activation and neuronal loss, administration of catalase-transfected macrophages dramatically decreased oxidative stress, and increased neuronal survival. Administration of empty-vector transfected macrophages did not affect microglia activation, or number of dopaminergic neurons in mice with brain inflammation. Statistical significance (shown by asterisk: $p<0.05$) was assessed by a standard t-test compared to mice with i.c. LPS injections followed by i.v. PBS injections (healthy controls). Values are means±SEM (N=4).
Figure 3:
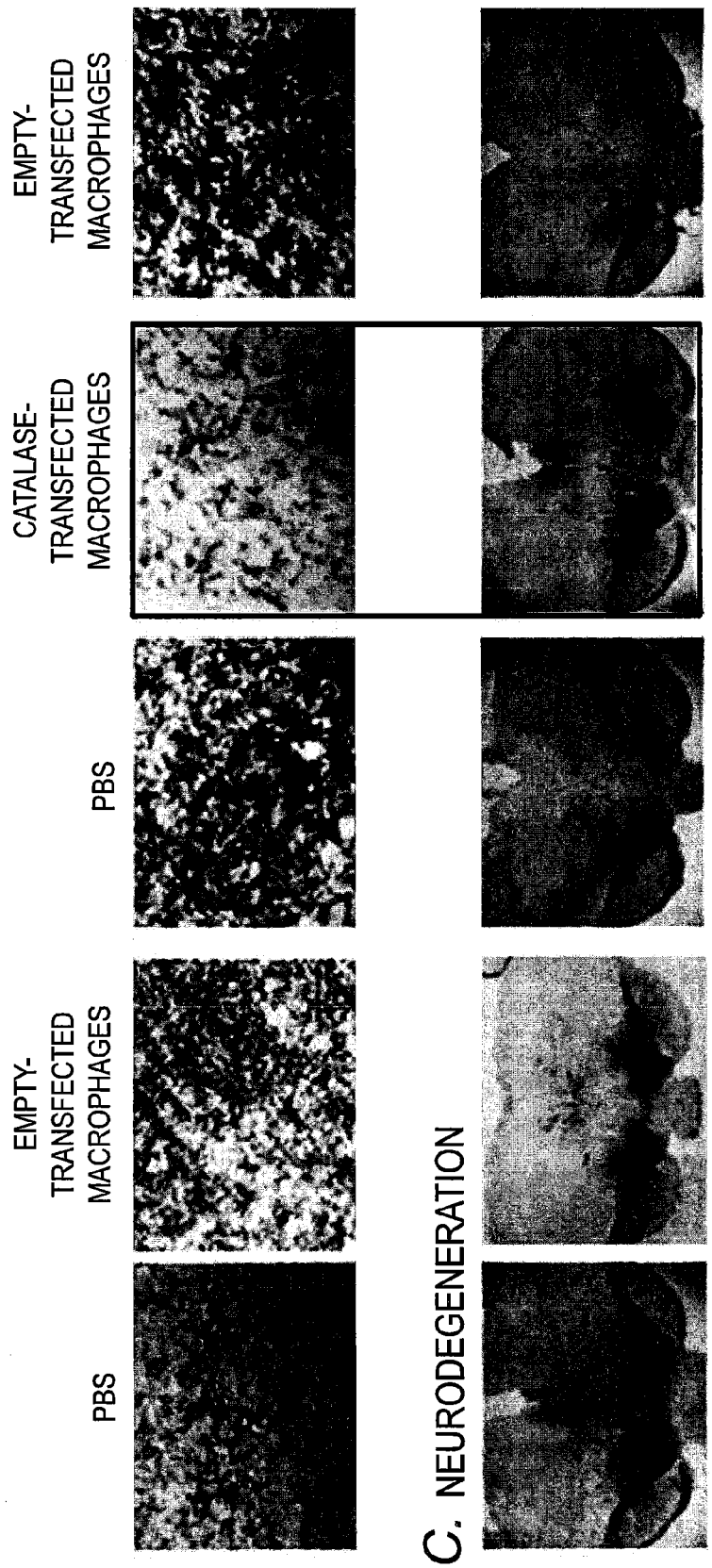

Linkages between neuroinflammation and nigrostriatal degeneration exist (Stone et al. (2009) Antioxid. Redox. Signal 11:2151-2166). Thus, transfection of brain tissues to express a redox enzyme, catalase, to attenuate inflammation could serve to protect dopaminergic neurons in disease (Ebadi et al. (1996) Prog. Neurobiol., 48:1-19; Wu et al. (2003) Proc. Natl. Acad. Sci., 100:6145-6150). The ability of catalase-transfected macrophages to reduce brain inflammation was demonstrated first, by IVIS studies in BALB/c mice stereotactically injected with LPS into SNpc. The extent of inflammation as a chemiluminescence signal within the brain produced by Xenolight™ RediJect was quantified and presented as a radiance ratio of treated animals vs. LPS-injected mice at 24 hours after the LPS injection (FIG. 3, Panel A). LPS intoxication induced 2.3-fold increase (SEM±0.3, N=4) in brain inflammation levels in LPS-injected mice compared to the day first after intoxication. In contrast, systemically administered catalase-transfected macrophages cased statistically significant decreases in neuroinflammation in LPS-intoxicated mice (2.1 times, SEM±0.03 at day 7, N=4), which was sustained for over a month after LPS intoxication. The representative IVIS images indicate complete abrogation of brain inflammation at day 30 by the single i.v. injection of catalase-transfected macrophages (FIG. 3, Panel A).

Next, potent anti-inflammatory and neuroprotective effects of catalase-transfected macrophages were demonstrated in the 6-OHDA-intoxicated mice (FIG. 3, Panels B and C). I.c. injections of 6-OHDA up-regulated expression of CD11b by microglia within the SNpc as exhibited a more amoeboid morphology in 6-OHDA-treated mice compared to ramified microglia in PBS-treated mice (FIG. 3, Panel B, Table 1). In contrast, treatment of 6-OHDA-intoxicated mice with catalase-transfected macrophages resulted in the decreased levels of CD11b and 65% less activated microglia cells compared with 6-OHDA-intoxicated control animals (FIG. 3, Panel B, Table 1). Finally, systemic administration of catalase-transfected macrophages completely prevented neurodegeneration in 6-OHDA intoxicated mice (FIG. 3, Panel C, Table 1). The numbers of TH+ neurons in SNpc of 6-OHDA animals treated with catalase-transfected macrophages were significantly (p<0.05) greater than those 6-OHDA intoxicated, and then PBS-injected animals. Noteworthy, the number of survived TH+ neurons in the ipsilateral side of 6-OHDA-intoxicated mice treated with catalase-transfected macrophages appears to be even greater (p<0.05) than those in the PBS-injected of control animals, which probably developed slight brain inflammation due to PBS i.c. injections. This signifies that catalase-transfected macrophages can efficiently reduce 6-OHDA-induced nigrostriatal inflammation and abolish subsequent neurodegeneration. No effect on microglia activation was found in control mice that were intoxicated with 6-OHDA, and then treated with empty vector-transfected macrophages. Nevertheless, these empty vector-transfected macrophages have subtle, but statistically significant neuroprotective effect in mice with i.c. PBS injections (FIG. 3, Panels B and C, and Table 1). It can be hypothesized that a particular subset of alternatively activated macrophages used in these studies (i.e. differentiated in presence of MCSF) has a regeneration effect (see, e.g., Kigerl et al. (2009) J. Neurosci., 29:13435-13444).

TABLE 1

Effect of catalase-transfected macrophages on inflammation and neurodegeneration in mice with PD model [a]

| Treatment | CD11b+ (cells/mm$^2$) | | Total N of neurons[b] × 10$^3$ | |
| --- | --- | --- | --- | --- |
| | PBS | 6-OHDA | PBS | 6-OHDA |
| PBS | 10.1 ± 1.2 | 90.0 ± 11 ()[c] | 6.9 ± 1.9 | 2.5 ± 0.5 () |
| Catalase-transfected macrophages | n/a | 31.2 ± 7.0 (*) | n/a | 9.7 ± 1.4 (*, #) |
| Empty-transfected macrophages | 9.8 ± 1.0 | 89.0 ± 11.1 | 8.2 ± 2.1 | 3.2 ± 0.7 |

[a]BALB/c mice were i.c. injected with 6-OHDA. Forty eight hours later, the animals were i.v. injected with various macrophage-based formulations or PBS. Control group was i.c. injected with PBS, and then 48 hours later i.v. injected with PBS.
[b]Total number of neurons was calculated in ipsilateral hemisphere.
[c]Statistical significance is shown by asterisk: p < 0.05 (*), and p < 0.005 (**) compared to mice with i.c. PBS injections followed by i.v. PBS injections (healthy controls); or p < 0.05 (#),compared to mice with i.c. 6-OHDA injections followed by i.v. PBS injections (PD controls); was performed by a1 + standard t-test. Errors are mean ± SEM, N = 7.

Figure 4:
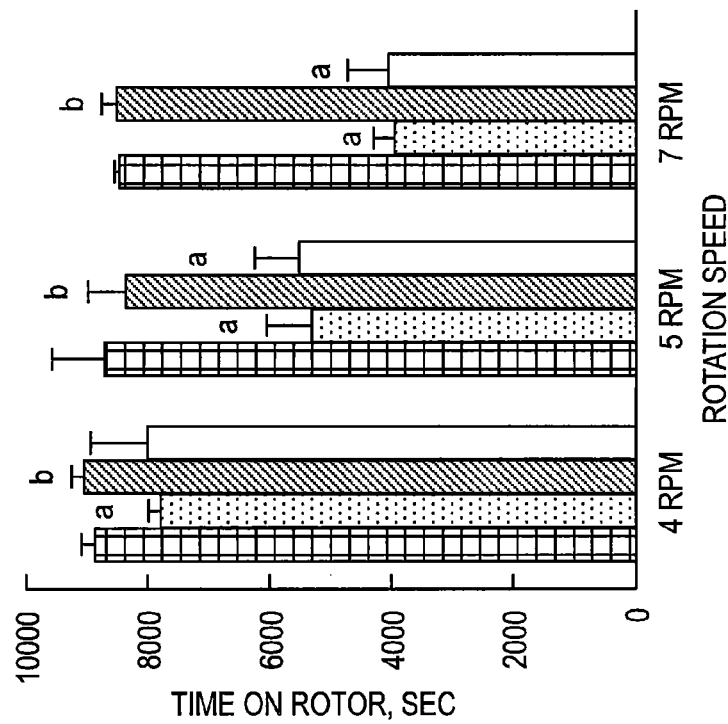
FIG. 4 shows the therapeutic effect of catalase-transfected macrophages on motor functions in a PD mouse model. BALB/c mice were i.c. injected with 6-OHDA. Forty eight hours later, the animals were i.v. injected with catalase-transfected macrophages (bars with diagonal pattern) or PBS (black bars), or empty-transfected macrophages (white bars). Control group was i.c. injected with PBS, and then 48 hours later i.v. injected with PBS (grey bars). Apomorphine (Panel A) and rotarod (Panel B) tests demonstrated statistically significant improvements in motor functions upon treatment with catalase-transfected macrophages. Number of rotations (Panel A) was significantly decreased in 6-OHDA-intoxicated mice treated with catalase-transfected macrophages compared to non-treated PD mice. No rotations were detected in control PBS-injected mice in apomorphine test. Time spent on the rotarod (Panel B) in 6-OHDA intoxicated mice treated with catalase-transfected macrophages was the same as in healthy non-intoxicated control mice on the seventh week after the intoxication. In contrast, significant decreases were observed in 6-OHDA-intoxicated mice injected with PBS. No effect on motor functions was recorded in 6-OHDA-intoxicated mice treated with empty-transfected macrophages. Statistical significance was calculated using one-way ANOVA test. Values are means±SEM (N=10), and p<0.05 compared with $^a$PBS, and $^b$6-OHDA.
Figure 4:
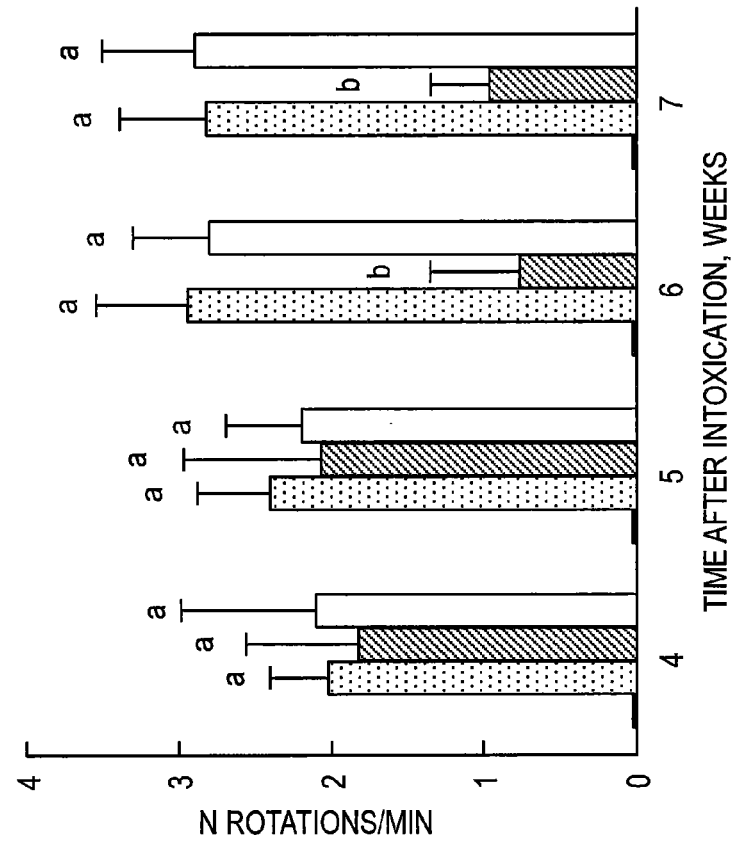

Finally, behavioral tests demonstrated statistically significant improvements in motor functions upon treatment with catalase-transfected macrophages (FIG. 4). Specifically, the loss of dopaminergic input due to the lesion of the left nigro-striatal pathway resulted in number of full-body contralateral rotations induced by a dopaminergic agent, apomorphine. In contrast, systemic administration of catalase-transfected macrophages to 6-OHDA intoxicated mice considerably (p<0.05) reduced number of these rotations on the seventh week following the intoxication in apomorphine test (FIG. 4, Panel A). Furthermore, the motor functions were preserved by systemic administration of catalase-transfected macrophages in 6-OHDA intoxicated animals at the levels similar to those of control non-intoxicated mice, as demonstrated in rotarod test (FIG. 4, Panel B). Noteworthy, no effect on motor functions was recorded upon administration of empty-transfected macrophages.

Cargo of Exosomes Secreted from Transfected Macrophages

Figure 5:
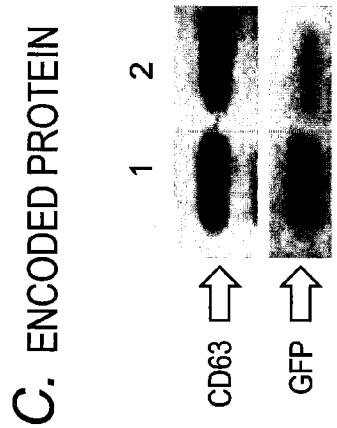
FIG. 5 shows exosomes secreted from GFP-transfected macrophages contain GFP DNA, RNA, the transcription factor, and expressed protein. Exosomes from GFP-transfected cells were collected over two days and evaluated for (Panel A): GFP DNA (1) and RNA (2) by PCR analysis. Exosomes secreted from macrophages transfected with empty vector were used as a control (3). Panel B: Levels of GFP DNA and RNA in exosomes from GFP-transfected macrophages were compared to those from empty vector-transfected macrophages (1), or non-transfected cells (2) by Real-Time PCR analysis. Panel C: expression levels of GFP (30K) in exosomes from GFP-transfected cells (1) or empty vector-transfected macrophages (2) were examined by western blot and compared to the levels of CD63 (53K). Exosomes released from GFP-transfected macrophages contained four orders of magnitude more of GFP DNA and RNA compared to non-transfected macrophages or those transfected with empty vector (Panels A, B); and 6.1 times greater levels of the expressed protein, GFP (Panel C). Exosomes contain substantially higher levels of NF-κb, a transcription factor that involved in GFP pDNA expression, compared to macrophages as demonstrated by western blot (Panel D). AFM images of exosomes revealed differences between: small donut-shaped (empty) exosomes released from non-transfected macrophages (Panel E) and large spherical (filled with the expressed proteins and genetic material) exosomes (Panel F) from catalase-transfected macrophages. The bar: 200 nm.
Figure 5:
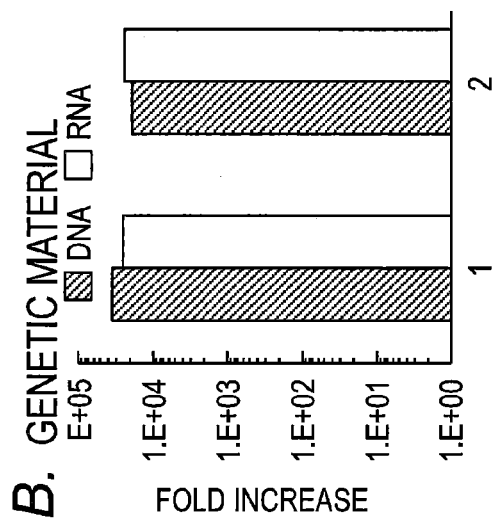
Figure 5:
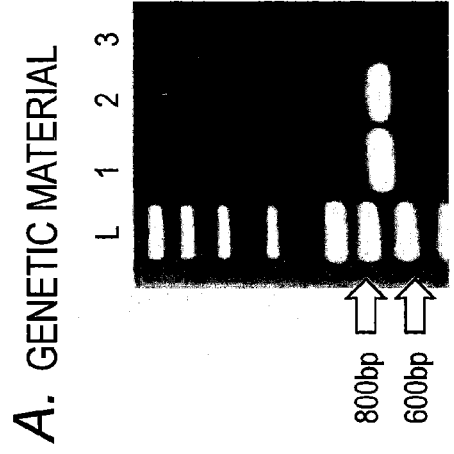
Figure 5:
Figure 5:
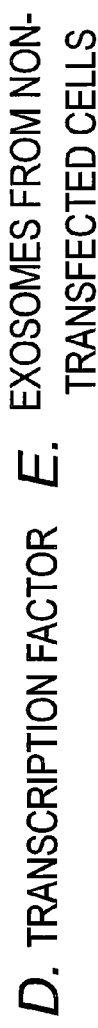
Figure 5:
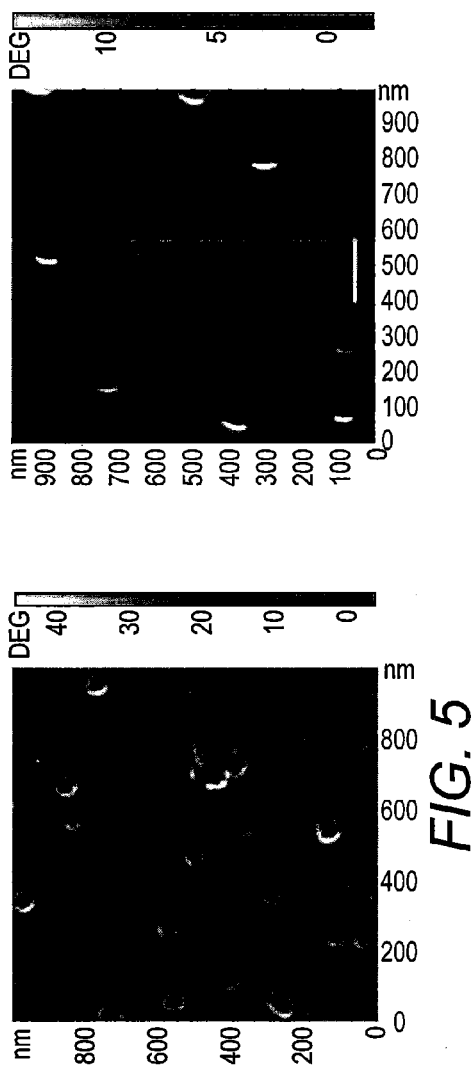

The significance of these findings is further underscored by the ability of macrophages to shed small vesicles (exosomes and microvesicles) (Thery et al. (2009) Nat. Rev. Immunol., 9:581-593) which can contain RNA, proteins and even pre-loaded in such cells nanoparticles (Haney et al. (2012) Nanomedicine 7:815-833). Here, it was evaluated whether transfected macrophages release these extracellular organelles with encapsulated pDNA, mRNA and protein products. From culture supernatants, exosomes and microvesicles were enriched and then this fraction was assessed for the presence of the transgene DNA and RNA by PCR and RT-PCR analyses (FIG. 5, Panel A, FIG. 5, Panel B). The results showed presence of both DNA and RNA of the encoded protein (here GFP) in exosomes released from transfected macrophages (FIG. 5, Panel A). Importantly, the levels of the genetic material were about four orders of magnitude greater compared to the exosomes secreted from non-transfected macrophages (FIG. 5, Panel B, group 1), as well as from the cells transfected with an empty vector (FIG. 5, Panel B, group 2). Western blot analysis indicated that exosomes released from transfected macrophages contained 6.1 times greater levels of the expressed transgene protein (GFP) than those obtained from cells transfected with empty vector (FIG. 5, Panel C). Finally, exosomes contained considerable amount of the transcription factor, NF-κB, which is particularly involved in the GFP expression under CMV promoter (FIG. 5, Panel D). This indicates that exosomes represent a highly efficient packaging system that can be used for the delivery of proteins and genetic material to target cells.

AFM images show round morphology of isolated exosomes from non-transfected macrophages presenting an average diameter of 48.1±0.03 nm (FIG. 5, Panel E). The donut-like shape is indicative of hollow vesicles with a central depression that appears upon drying in vacuum. Notably, exosomes from catalase-transfected macrophages were significantly larger (66.5±0.05 nm, p<0.001) compared to exosomes from nontransfected cells with a spherical shape sans central depression that may be due to packaging of the encoded protein and its genetic material (FIG. 5, Panel F).

Accumulation of Exosomes from Transfected Macrophages in Neurons

Figure 6:
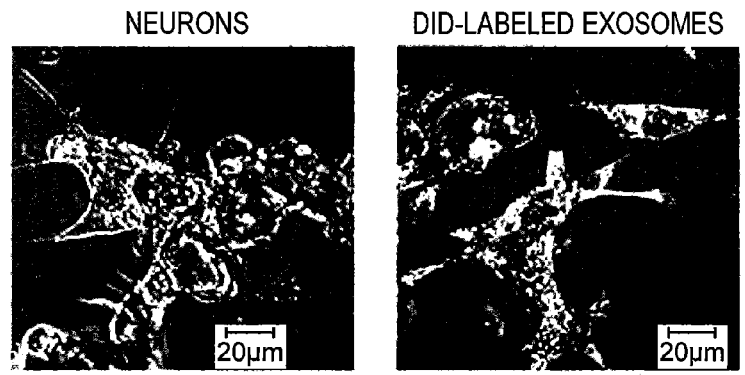
FIG. 6 shows the accumulation of exosomes secreted from macrophages in Cath.A neurons and genetic material transfer. Panel A: Cath.A neurons grown on slides were fixed and stained with Anti-NeuN Antibodies (left picture); exosomes were isolated from Raw 264.7 macrophages media, stained with lipophilic fluorescent dye, DIO, and added to Cath.A neurons for 24 hours (right picture). Panel B: Raw 264.7 macrophages were transfected with fluorescently-labeled with YOYO-1 tomato protein pDNA, and then cultured in complete media. Confocal images of transfected macrophages on day 3 show incorporation of pDNA in the nucleus and expression of tomato protein in the cytoplasm. Panel C: Media from macrophages transfected as described above with tomato protein pDNA (labeled with YOYO-1) was collected over 24 hours, and isolated exosomes were added to Cath.A neurons for various times. Then, the neurons were fixed and stained with Anti-NeuN Antibodies. Confocal images of neurons incubated with exosomal fraction demonstrated relatively constant amount of YOYO-1-labeled pDNA, and increasing in time expression levels of tomato protein confirmed by the quantification of green and red fluorescence on confocal images (graph). Co-localization of YOYO-1-labeled genetic material and expressed tomato protein in neurons is manifested by yellow staining. Statistical significance of tomato protein expression levels (shown by asterisk: p<0.05) was assessed by a standard t-test compared to day one after transfection. The bar: 20 μm.
Figure 6:
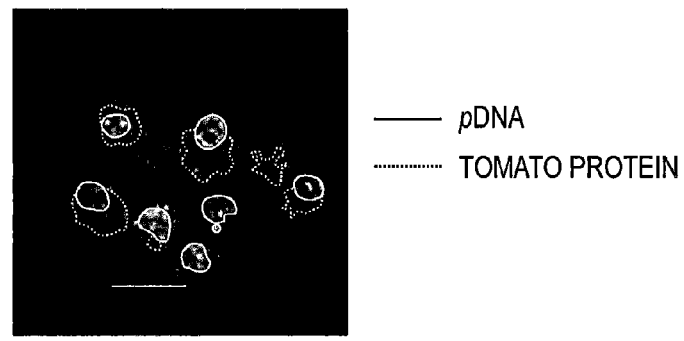
Figure 6:
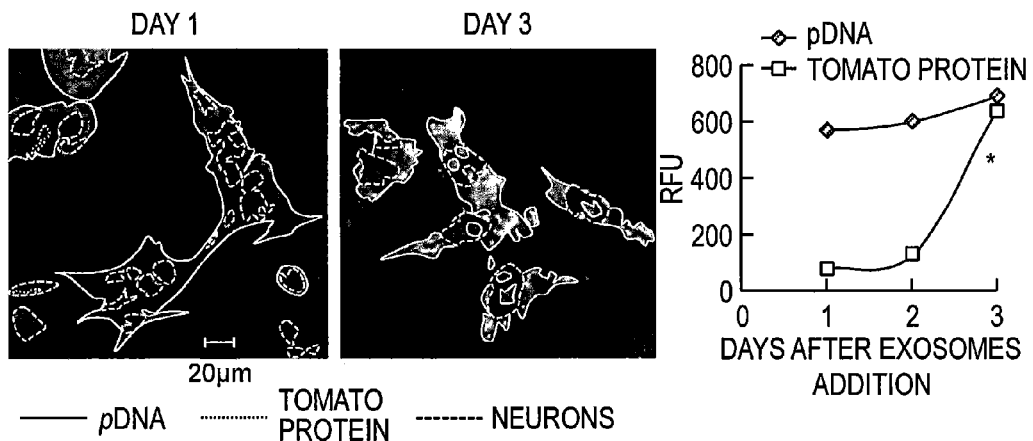

To study the exosomal transfer, exosomes isolated from macrophages concomitant media were labeled with lipophilic dye, DIO, and then Cath.A neurons were supplemented with these pre-labeled exosomes for 24 hours. Confocal images demonstrated substantial accumulation of DIO-labeled exosomes in target cells (FIG. 6, Panel A). Next, to visualize the gene transfer from exosomes to neurons, pDNA encoded tomato protein was labeled with a nucleoside stain, YOYO-1, and then RAW 264.7 macrophages were transfected with this pre-labeled pDNA. Confocal images of the transfected macrophages cultured in the complete media for three days revealed the nuclear accumulation of YOYO-1-labeled pDNA and the expression of the encoded tomato protein in cytoplasm of the genetically modified macrophages (FIG. 6, Panel B). Finally, media from the transfected macrophages was collected in day 3, and the isolated exosomal fraction was added to Cath.a neurons (FIG. 6, Panel C) to visualize genetic material transfer and the expression of the encoded protein. Indeed, the neurons exposed to the macrophage derived exosomes first accumulated the YOYO-1-labeled pDNA entrapped in these exosomes on day 1, and then expressed encoded red tomato protein on day 3 (FIG. 6, Panel C). The quantification of the green and red fluorescence in confocal images revealed a relatively constant amount of pDNA and time dependent increased expression of tomato protein (FIG. 6, Panel C, graph). This indicates that exosomes released from transfected macrophages can carry transgene and subsequently transfect neurons signifying the possible use of macrophages as proxy for gene transfer into the acceptor cells.

Figure 7:
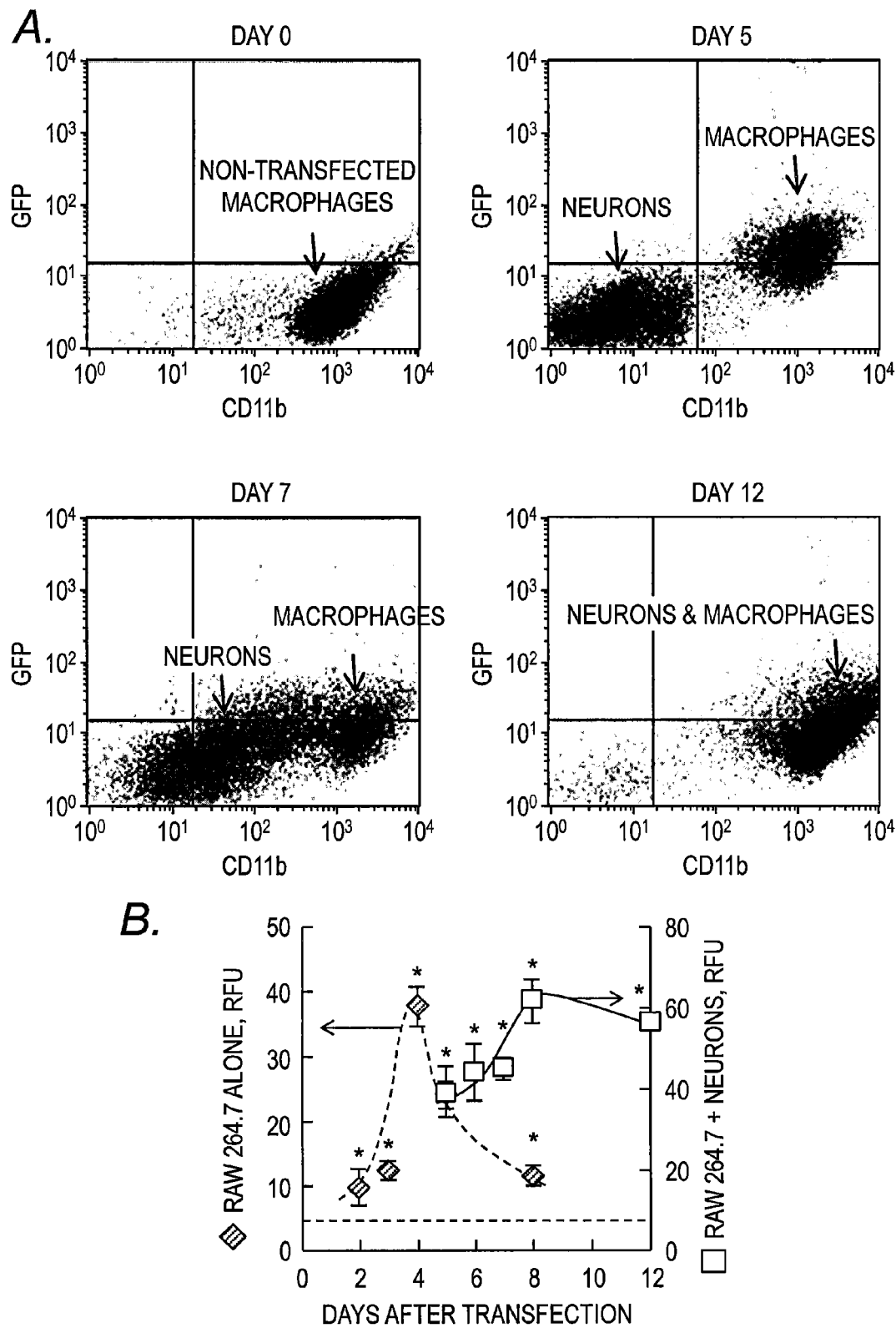
FIG. 7 shows the transfection of Cath.A neurons by GFP-transfected macrophages. RAW 264.7 macrophages were transfected with GFP pDNA, cultured in complete media for three days, and then added to Cath.A neurons. To distinguish between the cell types, macrophages were stained with CD11b Ab. GFP levels in neurons were assessed by FACS as mean fluorescence±SEM (N=4). Panel A: The representative FACS plots demonstrating GFP transfer into Cath.A neurons; Panel B: Quantification of GFP levels in macrophages alone (black diamonds), and in co-culture of neurons and macrophages (white squares). GFP expression levels in neurons co-cultured with transfected macrophages increased over 5-12 days. At the same time, protein expression in macrophages at days 5-12 was already diminished, indicating that along with GFP, its genetic material (pDNA and RNA) was transferred from transfected macrophages into neurons, where the encoded protein (GFP) was synthesized de novo. Statistical significance shown by asterisk (p<0.05) was calculated by a one-way ANOVA. The bar: 10 μm.

Kinetics of Gene Transfer from Genetically-Modified Macrophages to Target Neurons The kinetics of the gene transfer from macrophages to neurons was validated by FACS. Here, RAW 264.7 macrophages were transfected with GFP pDNA, cultured in the complete media for three days, and then added to Cath.A neurons at 1:1 of macrophage-neuron ratio. To distinguish between the donor (macrophages) and receiver (neurons) cells, macrophages were pre-labeled with antibodies to CD11b before the cell sorting. About 99.8% of macrophages were labeled (FIG. 7, Day 0). At 48 hours of the co-culture, GFP appears to be expressed exclusively in macrophages revealed as a CD11b+ population of cells (FIG. 7, Day 5). Over the time, GFP expression increases in neurons along with the appearance of CD11b marker in them (FIG. 7, Day 7) that ultimately yields one indistinguishable cell population (FIG. 7, Day 12). Taking into account that Cath.A neurons efficiently accumulate exosomes from transfected macrophages (FIG. 6, Panel A), neurons co-cultured with transfected macrophages acquired some of the CD11b-containig membranes of exosomes along with GFP genetic material and the expressed protein. Notably, the GFP expression levels in macrophages alone sharply declined after day 4 after transfection, as shown in FIG. 1, Panel A. In contrast, the co-culture of macrophages and neurons displays a delayed GFP expression profile, with the maximal expression shifted to day 8-12 (FIG. 7, graph). At the earlier times GFP gene expression is mostly associated with the macrophages, while at later times, expression by neurons increases and macrophage expression fades. This reinforces the concept that genetic material as well as protein products from transfected macrophages can be transferred to acceptor cells, where additional protein is synthesized de novo. Importantly, 97.6% of transfected macrophages and neurons in co-cultured mixture were alive on day 12 as confirmed by FACS.

Overall, these data demonstrate the importance of macrophage based gene and catalase carriage for PD therapies.

Herein, macrophages that were transfected with catalase pDNA were shown to produce a therapeutically active enzyme that can efficiently reduce ROS and benefit neuronal survival during upregulated oxidative stress similar to that associated with PD. To accomplish this goal, first, genetically modified macrophages should be able to reach the brain inflammatory sites in substantial quantities; therefore their migratory activity should not be compromised by the transfection. It is demonstrated herein that systemically administered macrophages transfected with luciferase pDNA reached the inflammatory site, delivering the encoded protein to the brain in PD mouse model. Interesting, maximum luciferase expression in the brain was detected on days 3 to 5 after macrophage transfer and was prolonged over a month with upregulated protein levels. Based on IVIS data (Brynskikh et al. (2010) Nanomedicine 5:379-396) indicating that i.v. injected fluorescently-labeled macrophages reach the inflamed brain sites maximum at day 5 with further their complete elimination by day 18, luminescence recorded three weeks after i.v. administration of luciferase-transfected macrophages may originate not only from the transfected cell-carriers, but also from the secondary transfected brain tissues. Notably, little, if any, luminescence was recorded in peripheral organs in mice with brain inflammation, or in the brain of healthy controls, indicating targeted gene and drug delivery by macrophages to the inflamed brain.

Next, to eliminate possibly recording the expressed protein in the blood vessels, slides of the main organs of mice that were injected with GFP-transfected macrophages and then perfused to wash out the blood content were examined by fluorescence confocal microscopy. The confocal images of the brain slides confirmed macrophage-mediated delivery of the overexpressed protein to the SNpc as early as 24 hours after systemic administration. Notably, brain tissues from the ipsilateral hemisphere demonstrate significant fluorescence throughout the SNpc area 5 days after macrophages administration. This demonstrates that genetically-modified macrophages secondarily transfected brain tissues.

Whether catalase transfected macrophages can produce a neuroprotective effect in PD mice was determined in two parts: i) decrease of neuroinflammation, and ii) increase of dopaminergic neuron survival. The level of inflammation was evaluated using a marker for activated microglia, antibodies to CD11b. In mice, the neurotoxin 6-OHDA reproduces most of the biochemical and pathological hallmarks of PD, including specific degeneration of dopaminergic neurons that originate in the SNpc and enervate the striatum. The results presented herein clearly demonstrated that, catalase-transfected macrophages show profound anti-inflammatory and neuroprotective effects in murine models of neuroinflammation and PD. Thus, systemic administration of catalase-transfected macrophages resulted in a substantial and prolonged attenuation of neuroinflammation (over 40 days) in mice with neuroinflammation. Furthermore, catalase transfected macrophages dramatically decreased inflammation, and increased neuronal survival in 6-OHDA-intoxicated mice. Therapeutic efficacy of the catalase-transfected macrophages was confirmed by 2.9-fold reductions in microgliosis as measured by CD11b expression, and 3.9-fold increase in tyrosine hydroxylase (TH)-expressing dopaminergic (DA) neurons as measured by TH, a marker for dopaminergic neurons, compared to 6-OHDA intoxicated mace treated with PBS. Notably, the number of survived DA neurons of mice after i.c. 6-OHDA intoxication followed by transfected macrophages systemic administration was even greater than those in control healthy mice i.c. injected with PBS. The potent neuroprotective effect by catalase-transfected macrophages was further manifested in significant improvements in motor functions in the 6-OHDA mouse model.

Significantly and unexpectedly, genetically-modified macrophages released the expressed protein and its genetic material (DNA and RNA) in exosomes, specialized membranous vesicles, that may facilitate transfer of their cargo to contiguous target neurons, similarly to macrophages pre-loaded with drug-incorporated catalase nanoparticles (Haney et al. (2012) Nanomedicine 7:815-833). Exosomes and microvesicles by themselves have attracted recently a significant attention as naturally occurring nanoparticles that may provide a noninvasive and novel therapeutic approach for efficient delivery of drugs across impermeable barriers, in particular the BBB (Alvarez-Erviti et al. (2011) Nat. Biotechnol., 29:341-345; Lakhal et al. (2011) Bioessays 33:737-741; Zhuang et al. (2011) Mol. Ther., 19:1769-1779;

van den Boom et al. (2011) Nat. Biotechnol., 29:325-326). This approach allows using individualized and biocompatible therapeutic drug delivery vehicles that can pass unrecognized by the patient's immune system (because they are, in fact, a part of immunocytes) and deliver the expressed therapeutic load to the disease site. However, two main challenges when using exosomes remain: a) the efficiency of drug loading into the exosomes, and b) targeting the exosomes to a particular cell type or organ. These challenges are resolved by using transfected cell-carriers for targeted gene and drug delivery, as demonstrated herein.

Thus, it is reported here that DNA and RNA of the encoded protein were detected in exosomes secreted from genetically modified macrophages by PCR and RT-PCR analyses. The data indicate four orders of magnitude increases in both DNA and RNA levels of the encoded protein in exosomes released from transfected macrophages compared to those from non-modified cells. Next, the upregulated amount of NF-κb, a transcription factor involved in pDNA expression, was detected in exosomes by western blot. This may further facilitate transfection and high expression levels of the encoded protein in target cells of a neurovascular unit (neurons, astrocytes, and brain microvessel endothelial cells). In fact, confocal microphotographs confirmed transfer of fluorescently-labeled DNA to neurons from exosomes released by transfected macrophages in vitro. Notably, expression of the encoded protein in the neurons was increased over time, while DNA levels remain constant. This indeed is crucial for therapeutic efficacy of an antioxidant that may have greater therapeutic effect when transferred into neurons. Furthermore, additional indications of the genetic transfer from cell-carriers to target cells were revealed in differences between the kinetics of the encoded protein expression in transfected macrophages cultured alone, or in co-culture with neuronal cells. The maximum protein expression in macrophages alone occurs on day 4 after the transfection followed by sharp decreases. In contrast, neighboring neurons pick up the expression of the protein by 8-12 days after macrophage transfection, indicating that de novo synthesis of protein occurs mostly in the neurons at later times.

Figure 9:
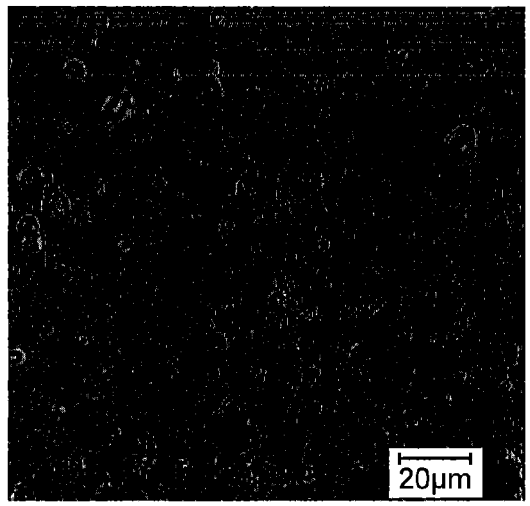
FIG. 9 shows the tracking of LV-GFPFLuc virus in mice with brain inflammation. BALB/c mice were I.c. injected with LPS into SN. Twenty four hours later, the animals were i.v. injected with LV-GFPFLuc virus ($2 \times 10^4$ particles/100 μl/mouse). One day (Panel A) and 5 days (Panel B) later mice were sacrificed, and perfused with PBS and 4% PFA. Brains were frozen, sectioned with a cryostate (10 μm thick), and examined by confocal microscopy (60× magnification). Representative images from N=4 animals detected no fluorescence in the brain indicating that LV-GFPFLuc virus particles were not able to penetrate the BBB and deliver GFP genetic material. The bar: 20 μm.
Figure 9:
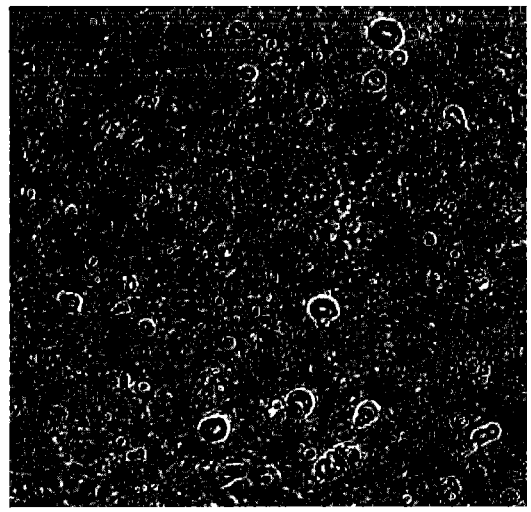

Herein, the ability of macrophages to deliver genetic material to the CNS has been clearly demonstrated, indicating this approach represents a new and novel alterative for gene therapy. To date, the majority of gene delivery systems have relied on viral vectors, of which adenovirus (Ad), adeno-associated (AAV), virus and retrovirus/lentivirus (LV) are the most commonly used (Kyritsis et al. (2009) Cancer Gene Ther., 16:741-752; Lentz et al. (2012) Neurobiol. Dis., 48:179-188). In the ideal setting, viral vectors are capable of achieving robust transgene expression. However, their application has been limited by high levels of immune system activation, minimal transduction efficiency, and reliance on direct intracranial administration (Manfredsson et al. (2009) Mol. Ther., 17:403-405). When delivered systemically, studies have shown that less than 1 in 100 copies of systemically administered LV are detectable in the brain (Pan et al. (2002) Mol. Ther., 6:19-29). This is supported by the findings which showed expression of GFP was undetectable in the brain following intravenous infusion of LV vectors (FIG. 9).

Although certain types of AAV are more efficient at transducing the brain (Foust et al. (2009) Nat. Biotechnol., 27:59-65), wide variation among serotypes is observed following systemic administration (Manfredsson et al. (2009) Mol. Ther., 17:403-405). In contrast, it was observed herein that macrophages are capable of effectively and efficiently delivering transgenes into the brain. As such, macrophage-based gene therapy offers several advantages over traditional viral vector therapy. First, generation of macrophage-based delivery systems may increase the ease of generation. Macrophage-based systems are not reliant on cloning of transgenes into viral backbones or by viral packaging constraints that limit the size of transgenes. Secondly, viral vectors rely on specific receptors for entry and delivery of their single DNA or RNA-based transgene that can result in low or absent transduction. With the ability to deliver DNA, as wells as exosomes carrying protein and mRNA simultaneously, macrophage-based delivery of multiple payloads in a receptor-independent manner may overcome the low transduction efficiency observed with certain viral vectors. Additionally, the simultaneous delivery of DNA, RNA, and protein by macrophages may enhance the efficacy of therapeutic proteins compare to traditional viral vectors. Lastly, one of the greatest limitations of Ad or LV vectors is robust activation of the host immune system (Lentz et al. (2012) Neurobiol. Dis., 48:179-188). However, one can transplant autologous macrophages carrying therapeutic transgenes to avoid this limitation. Using a patient's own cells will minimize or eliminate activation of the host immune response by the drug delivery vehicle.

Figure 8:
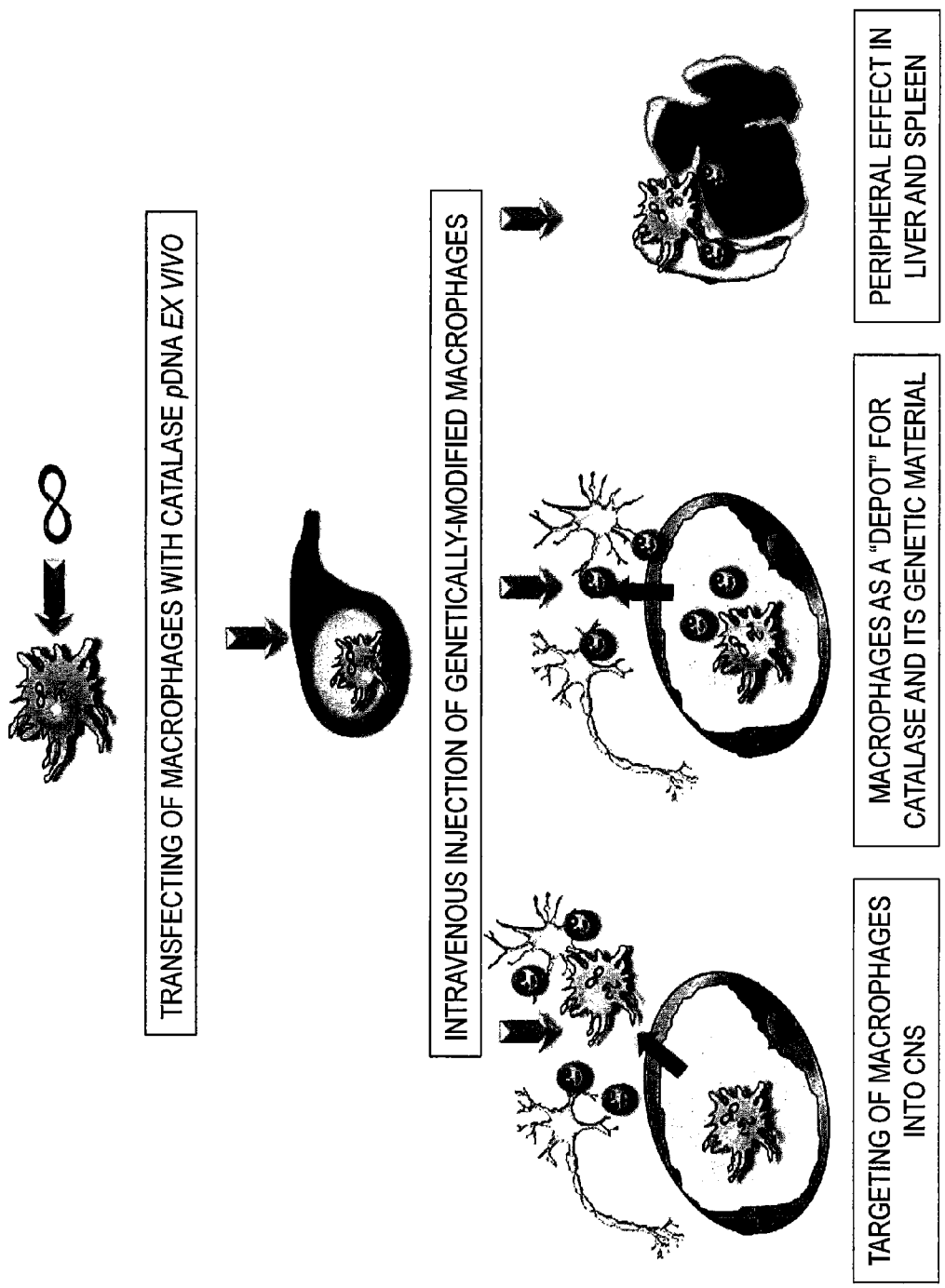
FIG. 8 provides a schematic for cell-based gene and drug delivery. Three ways of therapeutic effects of catalase-transfected macrophages in PD mouse model are depicted: Pathway I: macrophages transfected with catalase encoding pDNA cross the BBB and release catalase and its genetic material in SNpc; Pathway II: catalase and its genetic material are released from transfected macrophages in exosomes to the blood stream and bypass the BBB independently of the cell-carriers; Pathway III: gene and drug-incorporating exosomes released in the peripheral organs (liver, spleen, etc.) or in the blood are taken by residential macrophages, monocytes, T-cells, or dendritic cells suppressing peripheral leukocyte activation that may result in decrease of inflammation in the brain.

Overall, these studies indicate that genetically-modified macrophages serve as a new type of vector for gene transfer. They implement more than only inert carrier functions by being minifactories for multiplication, packaging, and targeted gene and drug delivery to the inflammation site. Taking into account that exosomes from macrophages may efficiently adhere to neurons due to the presence of various adhesive glycoproteins (Thery et al. (2006) Curr. Protoc. Cell Biol., Chapter 3: Unit 3-22; Denzer et al. (2000) J. Cell Sci., 113:3365-3374; Hogan et al. (2009) J. Am. Soc. Nephrol., 20:278-288), fuse to their membranes and deliver their content (Haney et al. (2012) Nanomedicine 7:815-833), it was hypothesized that genetic material was shuttled into neurons by this mechanism resulting in fundamental effect on neuronal survival during oxidative stress in murine models of PD. Without being bound by theory catalase-transfected macrophages may cross the BBB and deliver catalase and its genetic material to the inflamed brain (FIG. 8, Pathway I). The catalase transfected macrophages may release at least a portion of exosomes with catalase and catalase genetic material in the blood stream and then these extracellular vesicles reaches CNS independently of cell-carriers (FIG. 8, Pathway II). The exosomes may also be released from macrophages in the peripheral organs (liver, spleen, etc.) or blood stream and are taken by host circulating monocytes, residential macrophages, T cells, etc., which deliver exosomes with their cargo to SNpc by the same route as transfected macrophages shown in these studies (FIG. 8, Pathway III).

EXAMPLE 2

M2 macrophages play a critical role in tissue remodeling and healing after inflammation or injury. Transfection of host tissue by loading pDNA into M2 macrophages encoding therapeutic proteins will serve as active targeted gene delivery vehicles to diseased tissue only. The advantages for this system include active targeted protein/DNA/drug transport to the disease sites; gene preservation in the blood stream; prolonged half-lives of protein; and time-controlled release specifically to diseased tissues.

Figure 12A:
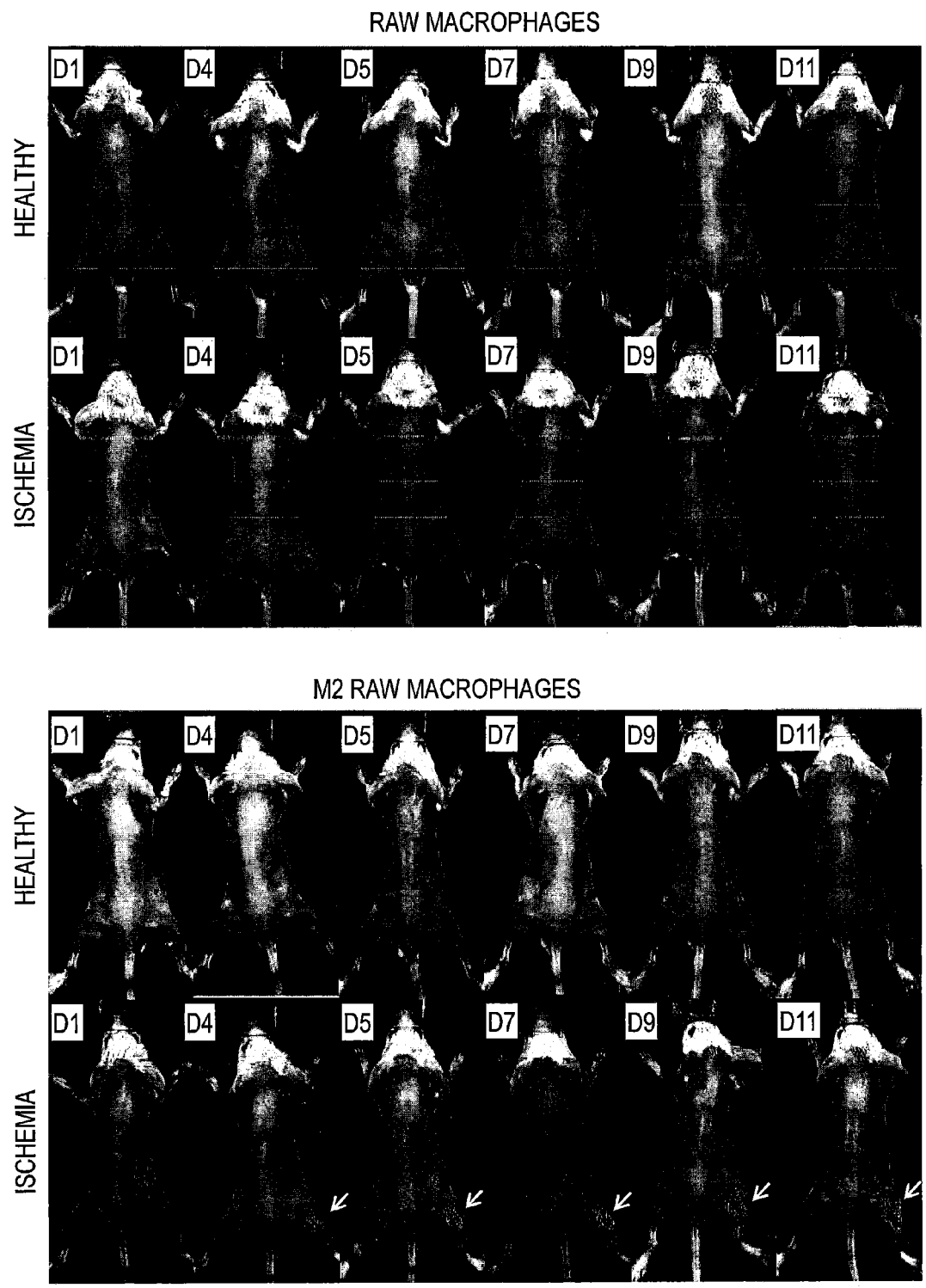
FIGS. 12A-12B show IVIS in vivo imaging of non polarized (top) and M2 polarized (bottom) macrophages in healthy and ischemic animals. M2 macrophages trafficked specifically to ischemic tissues (bottom, marked with red arrows).
Figure 12B:
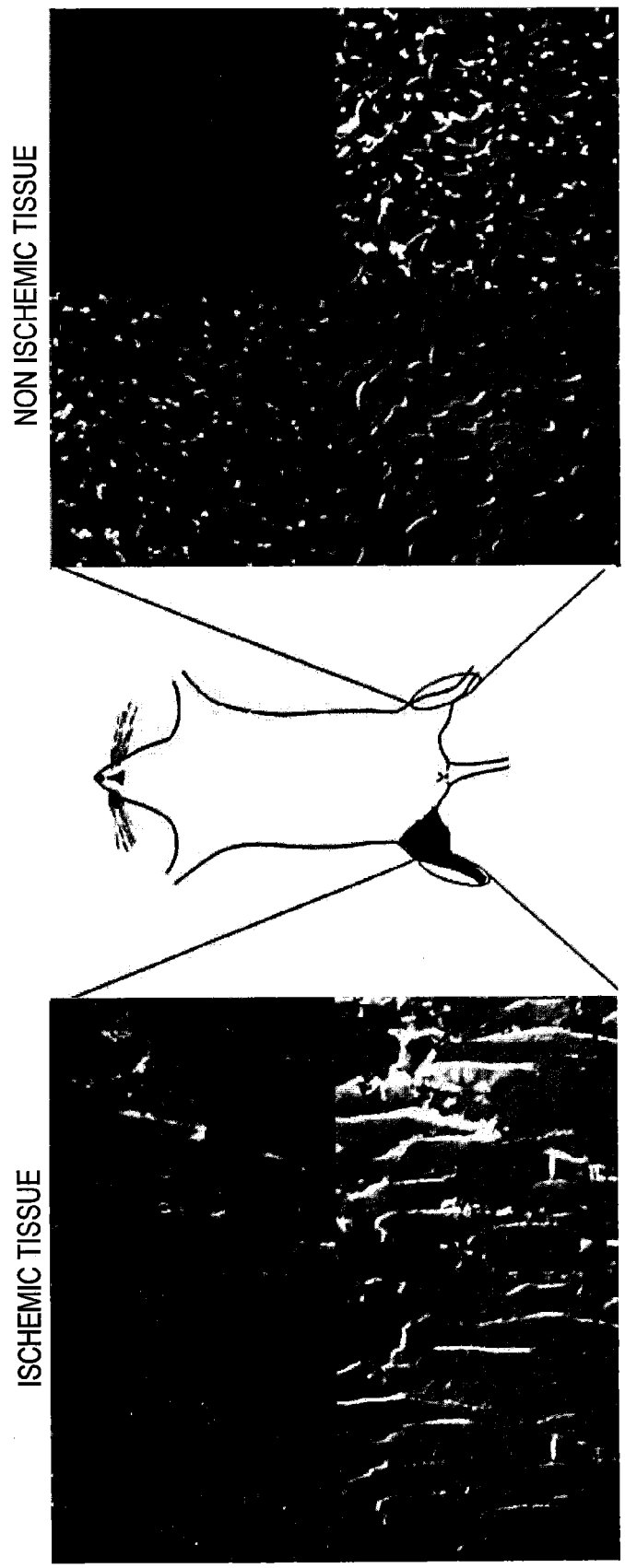

The delivery of anti-inflammatory cells for gene delivery to host tissue can comprise: i) polarizing macrophages to M2 anti-inflammatory type for targeting to diseased (ischemic) tissue; ii) transfection of M2 macrophages with plasmid DNA (pDNA); and iii) administration of transfected M2 macrophages i.v. to mice. The order of i) and ii) may be switched. Alexa Fluor® 680 labeled non polarized and polarized (M2) immortalized RA W264.7 balb/c macrophages were injected i.v. into healthy and ischemic mice. These animals were imaged to follow the biodistribution of fluorescently labeled macrophages over days in vivo by IVIS in vivo imaging system. The results demonstrate that M2 are specifically targeted to diseased tissue (FIG. 12A).

After the first 24 hours of incubation with M-CSF supplemented media, M2 macrophages were then transfected with green fluorescent protein (GFP) encoding pDNA with GenePORTER® 3000 transfection reagent for 4 hours, washed and cultured in complete media (+M-CSF) for another 24 hours. Transfected macrophages were washed thrice with phosphate buffered saline and administered in murine hind limb ischemia mouse model via intrajugular vein (i.j.v) injection post surgery. Animals were sacrificed 3 days post cells administration i.v. and 10 µm sections of muscle tissues visualized under confocal microscope (FIG. 1213). Analysis of tissue sections indicates: i) specific targeting of M2 macrophages to diseased tissues only with no GFP transfected macrophages in healthy (non-ischemic) tissues of same subject; ii) delivery of cargo (e.g., GFP) protein to diseased tissues and not to non diseased tissues; and iii) transfection of host muscle fibers with DNA secreted by the transfected M2 macrophages via exosomes or microvesicles, etc. In conclusion, the results indicate that M2 macrophages home to diseased tissue. Moreover when these M2 macrophages are transfected with DNA, they deliver plasmid DNA, mRNA and proteins via secreted exosomes or microvesicles to the host diseased tissue.

EXAMPLE 3

Figure 10A:
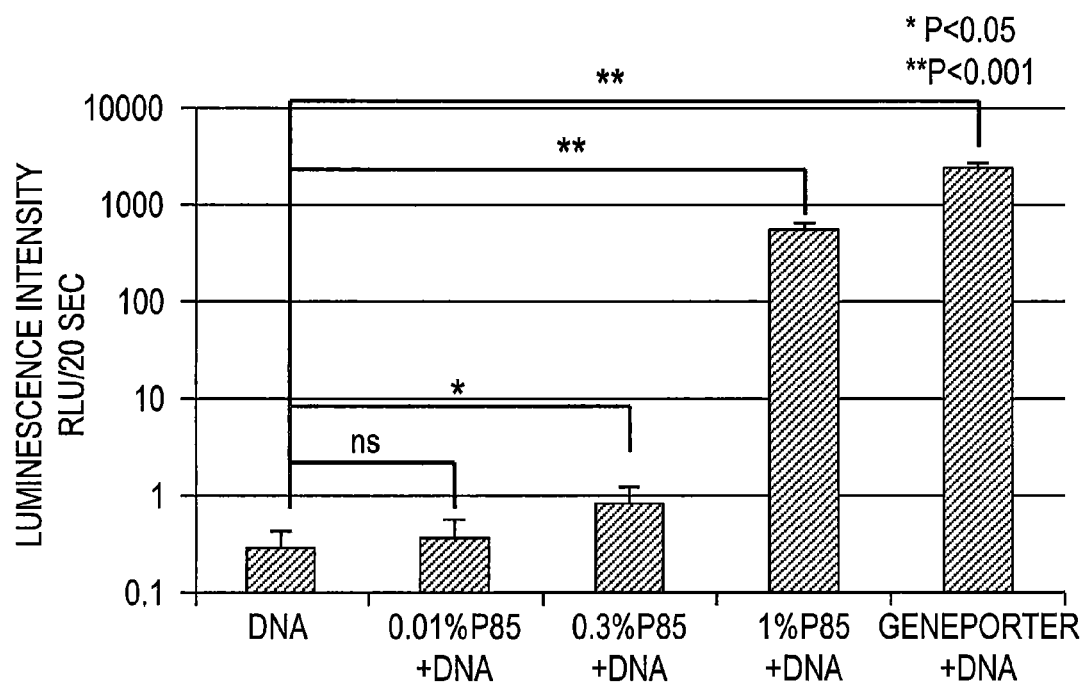
FIG. 10A shows gene expression in RAW264.7 macrophage cell lysates following incubation of cells with 1 μg DNA and increasing concentrations of Pluronic® P85 for 4 hours. Data are mean±SEM (n=3). P values were obtained by the means of Student's t test.

Pluronic® P85 (EO=52; PO=39) was dissolved in PBS (10% wt/wt) at room temperature and kept at 4 degree Celsius overnight. Increasing concentration of P85 was physically mixed with 1 µg of plasmid DNA (pDNA) encoding luciferase gene in phosphate buffered saline. RAW264.7 macrophage/monocyte cell line was plated at 500,000 cells/well in 24 well plates and incubated with P85 and pDNA premix in serum free media for 4 hours. The cells were washed thereafter and incubated with complete media for another 16 hours. Media was removed and cells were lysed using cell culture lysis buffer (Promega) for 30 minutes and luciferase activity was monitored on luminometer using 10 µl sample supernatant. Each reaction was performed in triplicate with triplicate readings of each sample. Geneporter® pDNA and cells alone were used as positive and negative control. 1.0% Pluronic® P85 significantly increased the transgene expression in macrophages compared to plasmid DNA alone (~2000 times) (FIG. 10A).

Figure 10B:
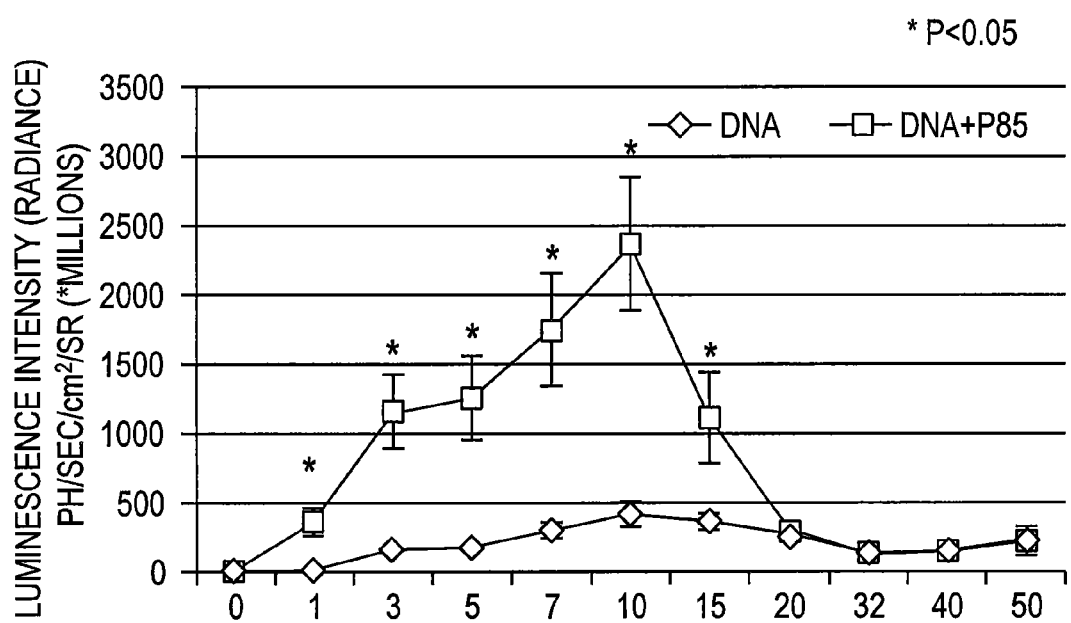
FIG. 10B shows dependence of the luminescence intensity over the indicated number of days after administration of DNA or DNA plus P85 (0.3%).
Figure 10C:
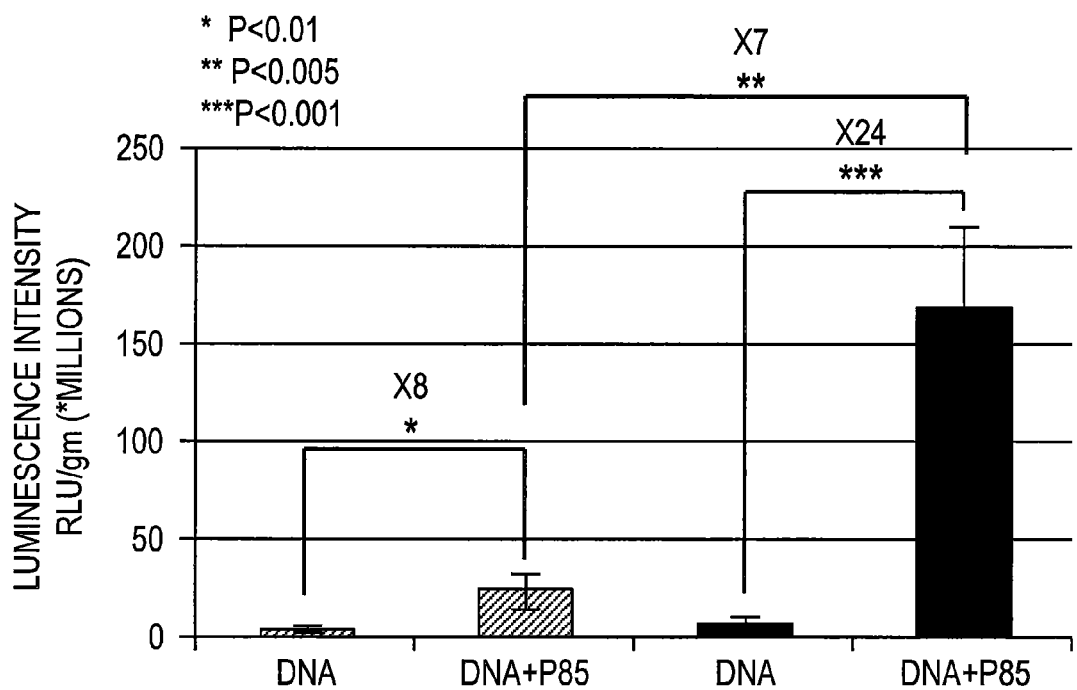
FIGS. 10C and 10D show the luminescence intensity in muscle (FIG. 10C) or lymph nodes (FIG. 10D) three days after administration of DNA or DNA plus P85 (0.3%) to healthy mice (grey bars) or mice with a murine hind limb ischemia model (black bars).
Figure 10D:
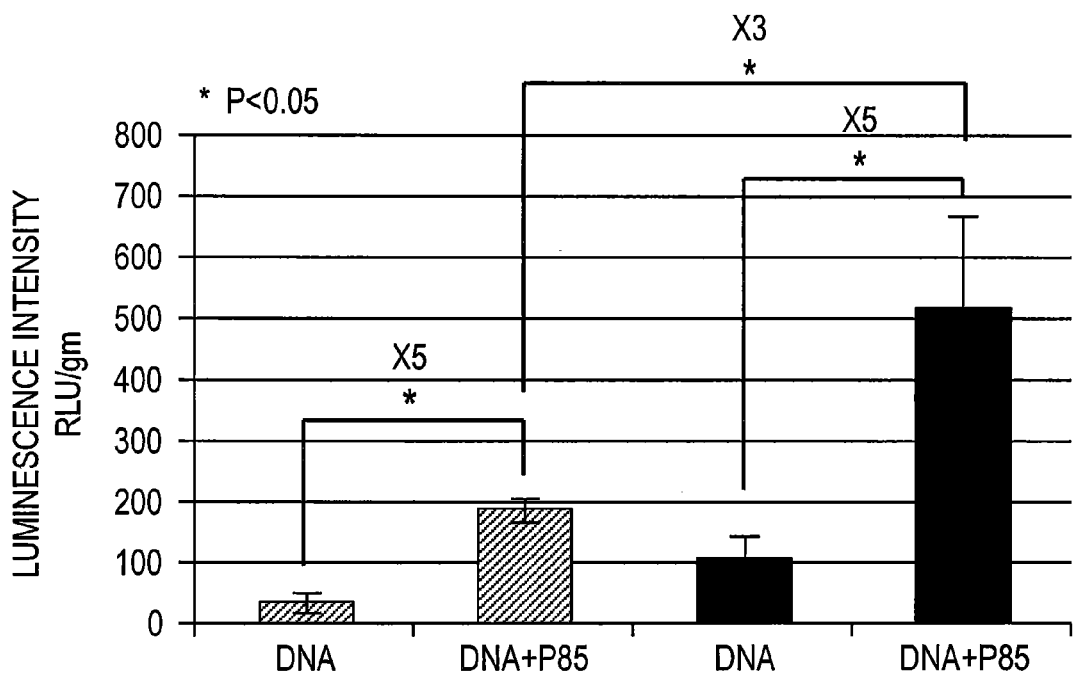
Figure 10E:
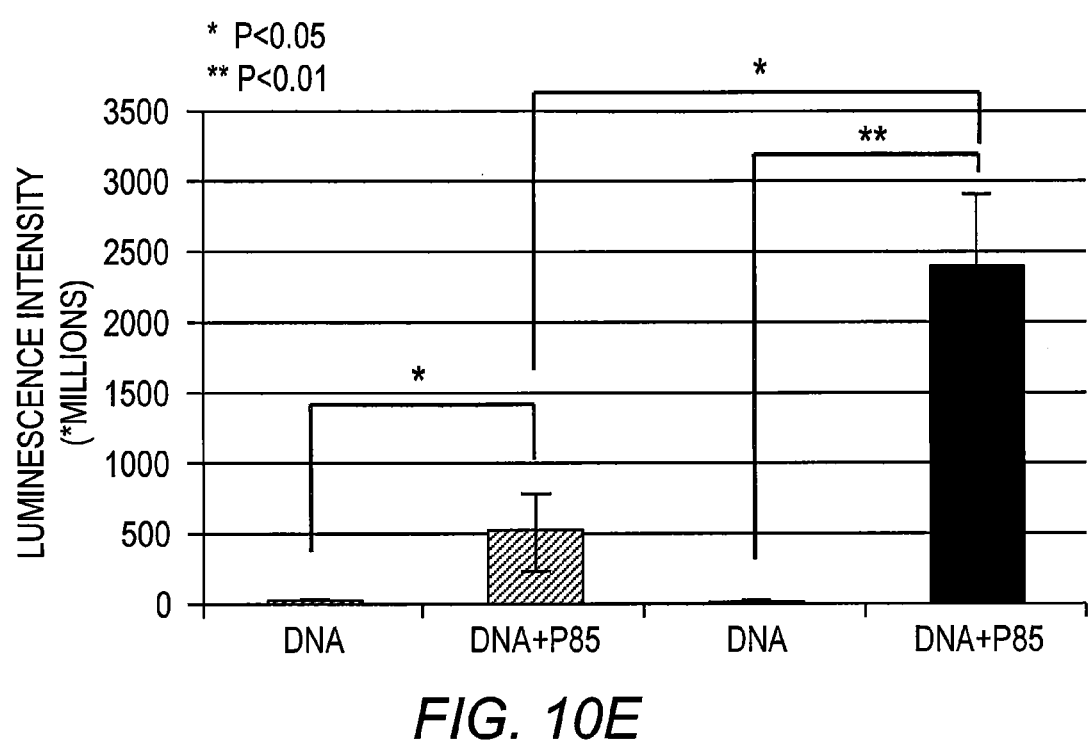
FIG. 10E shows the luminescence intensity in muscle following five days after administration of DNA or DNA plus P$5 (0.3%) to healthy mice (grey bars) or mice with a murine peritonitis model (black bars) in muscle.

The P85 and DNA mixtures were also delivered to mice to demonstrate in vivo gene delivery. As seen in FIG. 10B, DNA+P85 (0.3%) dramatically increased gene expression compared to DNA alone. The complex was also administered to a murine hind limb ischemia model. As seen in FIG. 10C, DNA+P85 (0.3%) dramatically increased gene expression in muscle compared to DNA alone, particularly in the ischemia model compared to healthy mice. Similar results were observed in the lymph nodes of the mice (see FIG. 10D). The increase in expression was less pronounced when P85 was replaced with SP1017 (a mixture of L61 and F127). The complex was also administered to a murine peritonitis model (induced by administration of λ-carrageenan 1 mg/mice in 200 µl PBS). As seen in FIG. 10E, DNA+P85 (0.3%) dramatically increased gene expression in muscle at day 5 compared to DNA alone, particularly in the peritonitis model compared to healthy mice.

Figure 11A:
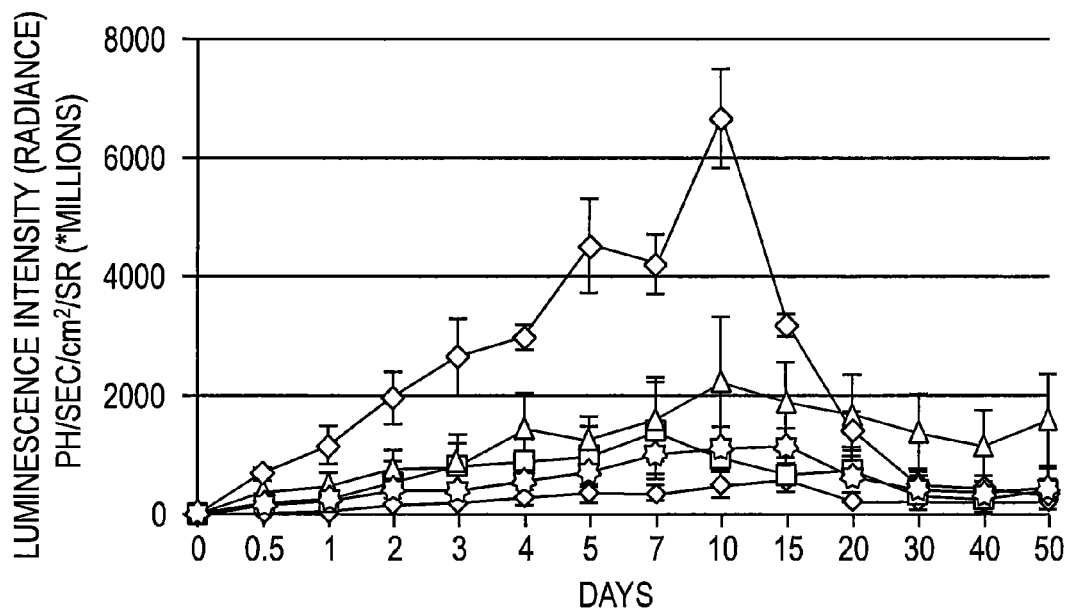
FIG. 11A shows the luminescence intensity over the indicated number of days after administration of DNA or DNA plus P85 (0.3%) after pre-injection (36 hours prior) of control, 0.3% P85, 3% P85, or 10% P85.
Figure 11B:
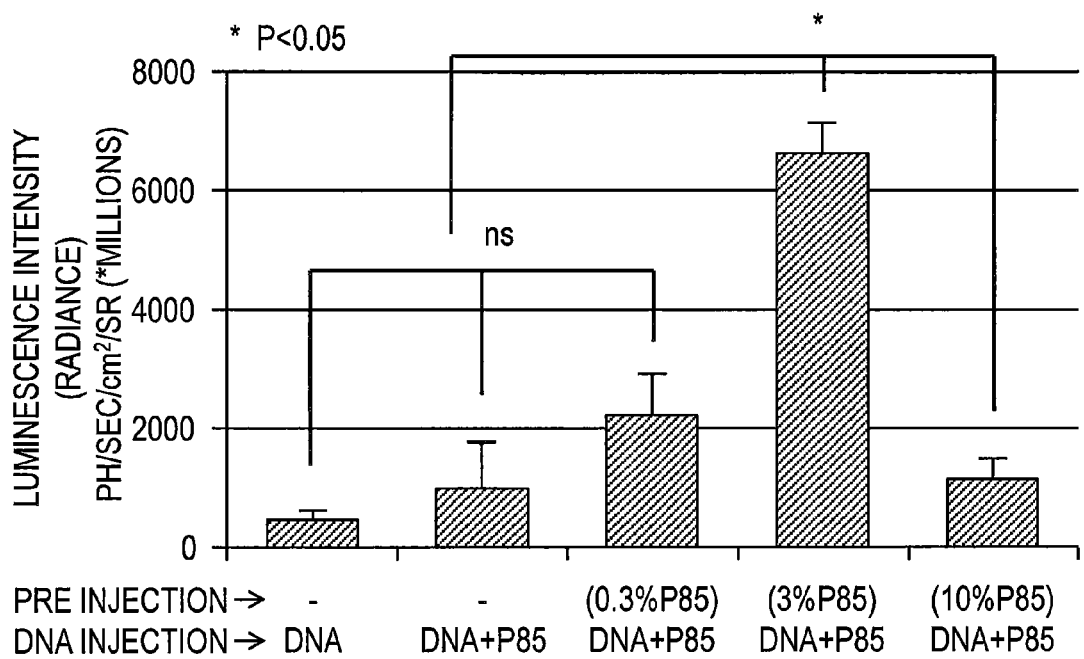
FIG. 11B shows the luminescence intensity in muscle ten days after administration of DNA or DNA plus P85 (0.3%) when the mice were pretreated (36 hours prior) with control, 0.3% P85, 3% P85, or 10% P85.

Lastly, the pre-injection of P85 was also tested in mice. Mice were injected with control or 0.3%, 3%, or 10% P85 36 hours prior to injection with DNA or DNA plus 0.3% P85. As seen in FIG. 11, the pre-injection of 3% P85 resulted in a dramatic increase of expression.

EXAMPLE 4

Figure 13:
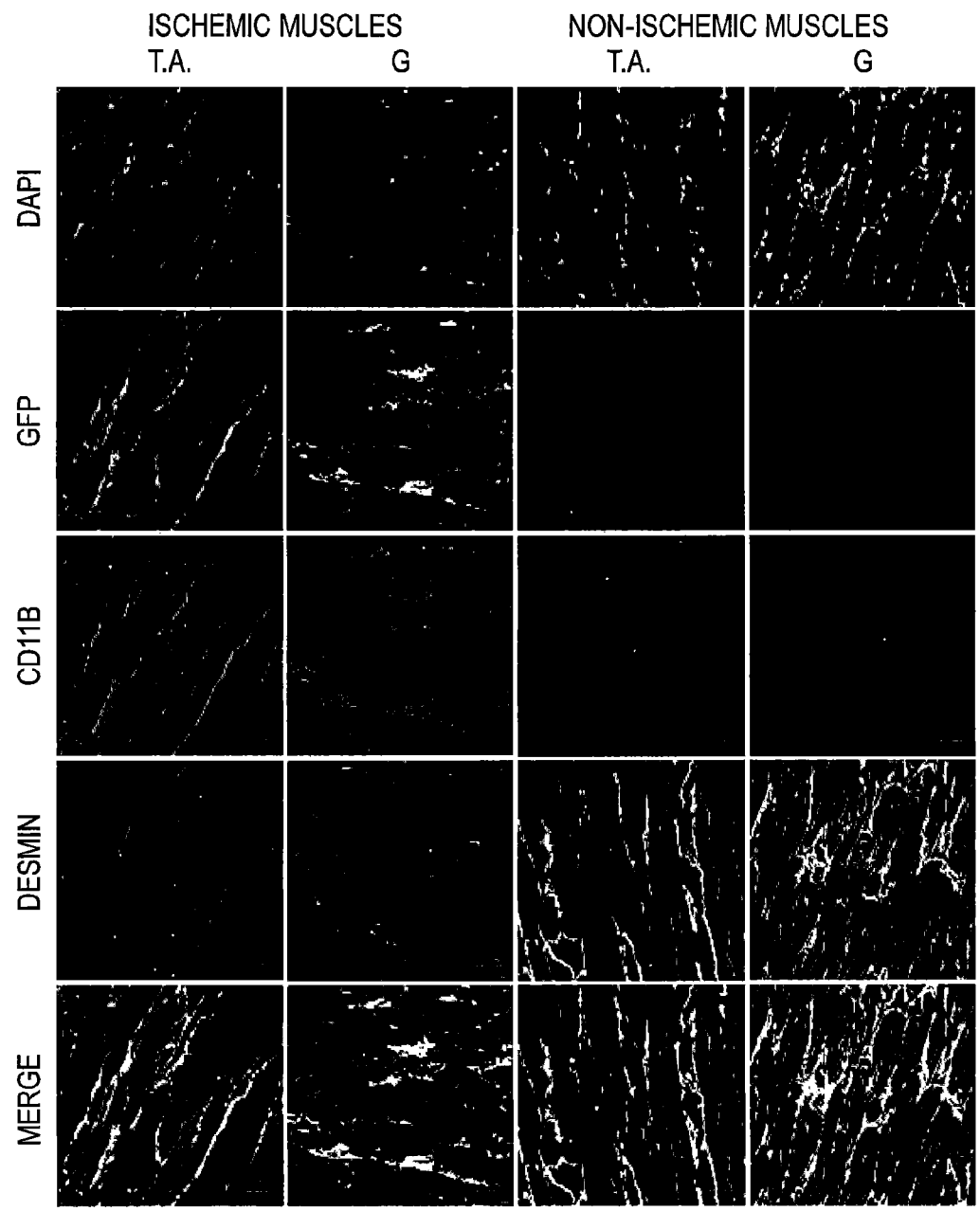
FIG. 13 shows in vivo transfection of muscle cells upon adoptive transfer of GFP transfected MPs: RAW 264.7 MPs were transfected ex vivo and 24 h after transfection injected in MHLIM Balb/c mice 48 h post ischemia surgery by i.j.v injection. Tissues were isolated 3 days post MPs administration and 10 μm sections of frozen tissues were processed for IHC. GFP expression co-localized with CD11b+ suggesting accumulation of transfected MPs in ischemic tissues but not in healthy muscle. Moreover, GFP expression in ischemic muscle also co-localized with desmin, suggesting that muscle cells were transfected. The colors correspond to nucleus DAPI staining (blue), GFP (green), CD11b (red) and desmin (cyan). The bottom panels present digitally superimposed images of preceding panels to visualize the co-localization (yellow or white). The images are representative of 3 sections per muscle and 3 mice per group. The images were taken with Zeiss 710 confocal laser scanning microscope using 20× objectives. Scale bar=50 μm.

The delivery of GFP from ex vivo transfected macrophages to muscle was confirmed by studying co localization of cell specific markers (FIG. 13). GFP expression colocalized with CD11b+ suggesting accumulation of transfected MPs in ischemic tissues but not in healthy muscle. Moreover, GFP expression in ischemic muscle also colocalized with desmin, suggesting that muscle cells were transfected. The colors correspond to nucleus DAPI staining (blue), GFP (green), CD11b (red) and desmin (magenta). The bottom panels present digitally superimposed images of preceding panels to visualize the co-localization (yellow or white). The images are representative of 3 sections per muscle and 3 mice per group. The images were taken with a Zeiss 710 confocal laser scanning microscope using 20× objectives. Scale bar represents 50 µm. Importantly, in ischemic muscles MPs were localized in close proximity to muscle fibers as was seen from co-localization of desmin and CD11b. This may explain cell-to-cell contact dependent exchange of repackaged nucleic acids/proteins from MPs across the membranes to otherwise hard to transfect skeletal muscle fibers.

Figure 14:
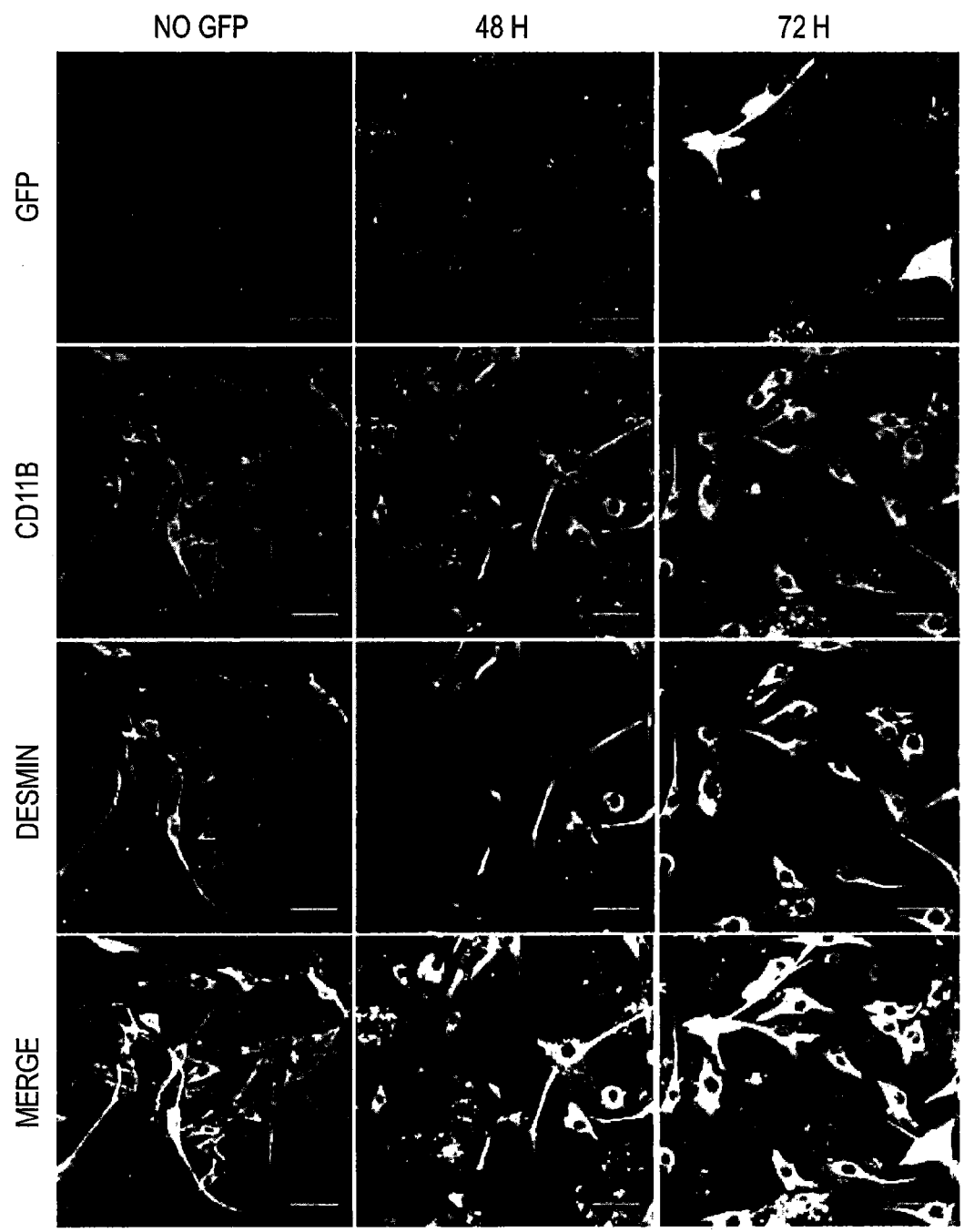
FIG. 14 shows in vitro transfection of muscle cells upon co-culture with GFP transfected MPs. Un-transfected MPs (left lane) and GFP DNA transfected MPs (right two lanes) were co-cultured with un-transfected MBs for up to 72 h. MBs stained positive for both GFP and CD11b at all time points. The color staining corresponds to GFP expression (green), CD11b MP marker (red), desmin muscle marker (cyan). The bottom panels present digitally superimposed images of preceding panels to visualize the co-localization (yellow or white). The images were acquired with Zeiss 710 confocal laser scanning microscope using 20× objectives. Scale bar=50 μm.

To evaluate the possibility of protein (GFP) transfer from MPs to muscle cells, we studied GFP exchange from MPs to muscle cells in vitro as well. GFP transfected MPs were co-cultured on undifferentiated muscle cells or myoblasts (MBs) and GFP expression in MBs was visualized by confocal imaging after 48 h and 72 h of co-culture. We observed increasing GFP expression in desmin+ MBs at each time point up to 72 h (FIG. 14). Interestingly MBs also stained positive for CD11b at later time points (48 h-72 h) after co-culture which confirmed a unidirectional membrane transfer from MPs to MBs and not vice versa (FIG. 14). This exchange may explain cell-to-cell communication to deliver the DNA/GFP protein to neighboring cells, in this case muscle cells.

Figure 15:
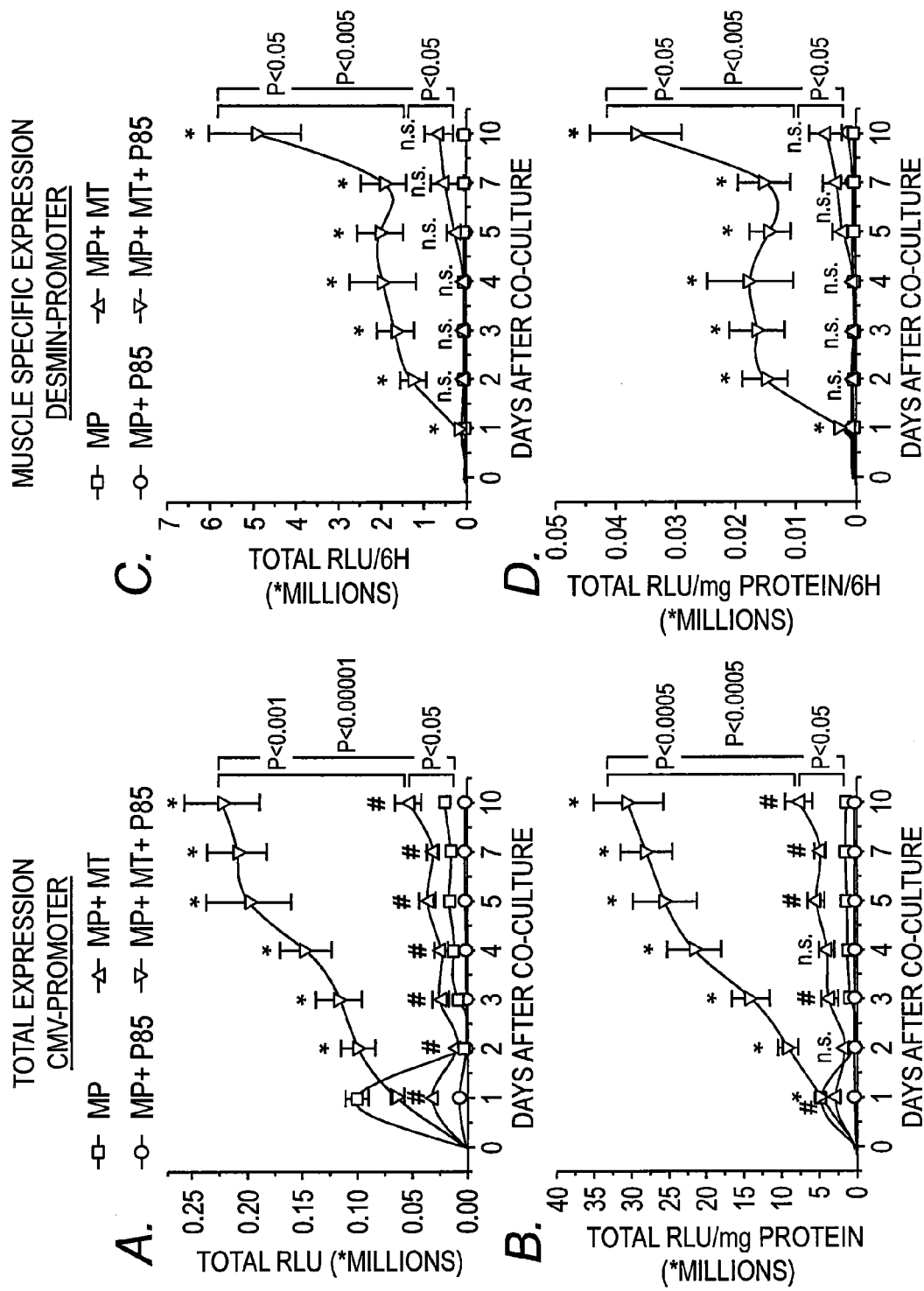
FIG. 15 shows DNA transfer from macrophages to muscle cells in the presence of P85 in an in vitro model of inflammation. Gene expression in MPs transfected with cmv-plasmid (Panels A, B) and desmin-plasmid (Panels C, D) alone and upon co-culture on MTs both with and without 2 h treatment of P85 (1% w/v) was compared on different days. Significantly higher muscle specific gene expression levels in a P85 dependent manner confirms DNA transfer from MPs to MTs (right) which resulted in high constitutive gene expression (left). Data represents Mean±SEM with n=12. Student's t test was used to find the statistical differences among groups (* represents MPs versus MP+MT+P85 and # represents MPs versus MPs+MTs). The experiment was repeated twice.

Finally, to evaluate the possibility of DNA transfer from MPs to muscle cells, we developed an in vitro model of inflammation. DNA transfected macrophages with and without P85 were cocultured on terminally differentiated muscle cells. The macrophages were transfected with two DNA vectors independently, constitutive CMV promoter-luciferase and muscle specific desmin promoter-luciferase DNA to quantify overall and muscle specific increase in gene expression. We used these models to study the kinetics of gene expression in MPs alone or upon co-culture on myotubes (MTs) with/without 2 h treatment of P$5 (1% w/v) in SFM (FIG. 15; Data represents Mean±SEM with n=12, Student's t test was used to find the statistical differences among groups, experiments were repeated twice). In the CMV-model, MPs alone expressed highest at 24 h with a sudden decline at 48 h, but when co-cultured with MTs, total expression increase gradually and stayed constant over several days representing a conduit/reservoir nature of adjacent cells (muscle cells). In contrast, when the co-culture was exposed to P85 for 2 h, the gene expression shot up increasing the expression levels up to ~28 and ~15 times of the total and normalized gene expression, respectively, through day 10 (FIG. 15, Panels A and B). In parallel, the Desmin model was used to confirm the DNA transfer from macrophages to muscle cells. Interestingly, we observed up to 120 and ~60 times increase in total and normalized gene expression when the co-culture was exposed to P85 compared to MPs alone (FIG. 15, Panels C and D). No such increase was observed in the absence of P85 in MPs+MTs that confirmed the role of Pluronic® in horizontal DNA transfer from macrophages to muscle cells hence resulting in higher muscle transfection efficiencies in vivo.

EXAMPLE 5

Figure 16:
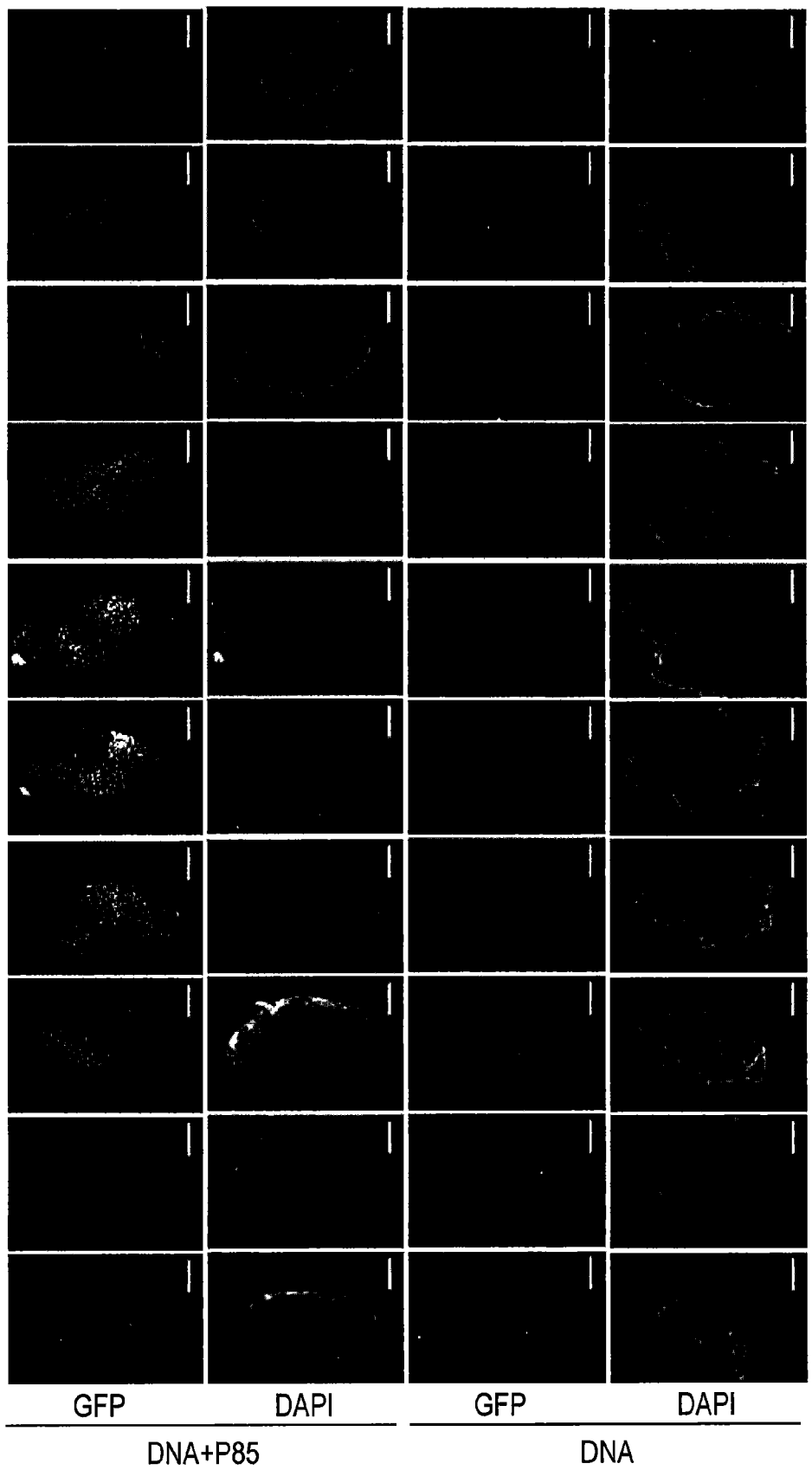
FIG. 16 shows GFP expression through ischemic muscle injected with DNA alone or DNA+P85. Tile scanning confocal microscope (10×) images of 20 μm sections at every 500 μm through the whole muscle tissue at 4 day after injections of gWIZ™ GFP DNA alone or DNA with 0.6% w/v P85. Representative images from each treatment group with n=3 are shown. Scale bar=1 mm.

Skeletal muscle constitutes 30% of the adult body mass, has an abundant vascular supply, and being terminally differentiated, has a long life span that makes it as suitable protein factory for various therapeutics (Lu et al., Gene Ther. 10(2):131-42 (2003); Chamberlain, Hum Mol Genet. 2002 11(20):2355-62 (2002); Viola et al., J Drug Deliv. 2013: 897348 (2013)). To be successful, the goal of naked DNA gene delivery to hard to transfect skeletal muscles is to increase the number of transfected muscle fibers which will impact the therapeutic outcome. For example, an increased number of transfected fibers can present antigen to an increased number of infiltrating immune cells thus resulting in a higher therapeutic outcome in DNA vaccination. Visualization of GFP expression in ischemic tissues injected with DNA alone or DNA+P85 (0.6%) revealed high transfection of muscle fibers (number of GFP+ fibers) resulting from Pluronic® (FIG. 16). Tile scanning confocal microscope (10×) images of 20 μm sections at every 500 μm through the whole muscle tissue at 4 day after injections of gWIZ™ GFP DNA alone or DNA with 0.6% w/v P85. Representative images from each treatment group with n=3 are shown. Scale bar=1 mm.

Figure 17:
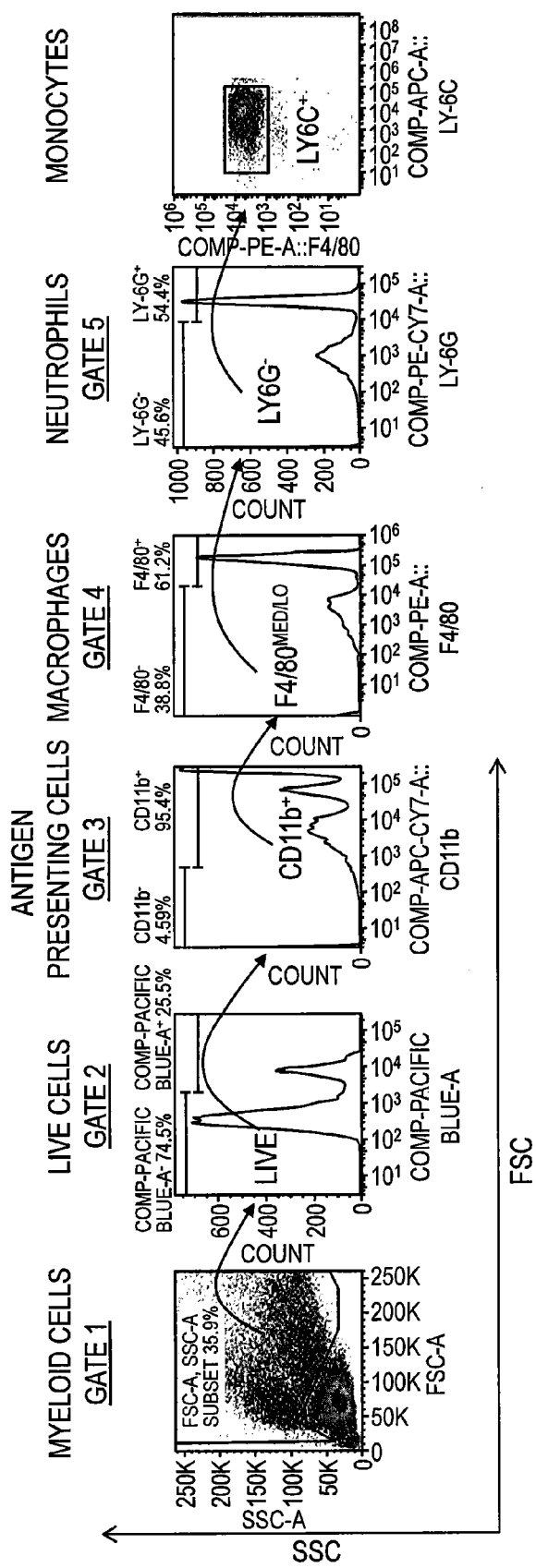
FIG. 17 shows the immune response (monocyte recruitment) to various formulations upon direct injections in vivo. Representative dot plots of monocyte recruitment at the site of injection. The respective formulations [PBS, 50 μg DNA, 50 μg DNA+P85 (0.3%), 50 μg DNA+SP1017 (0.01%), 500 μg Alum and 25 μg LPS] prepared in PBS were injected as 250 μl solution/mouse i.p. in immune-competent (balb/c) mice and immune-deficient (athymic nude) mice and cells isolated after 24 h.
Figure 17:
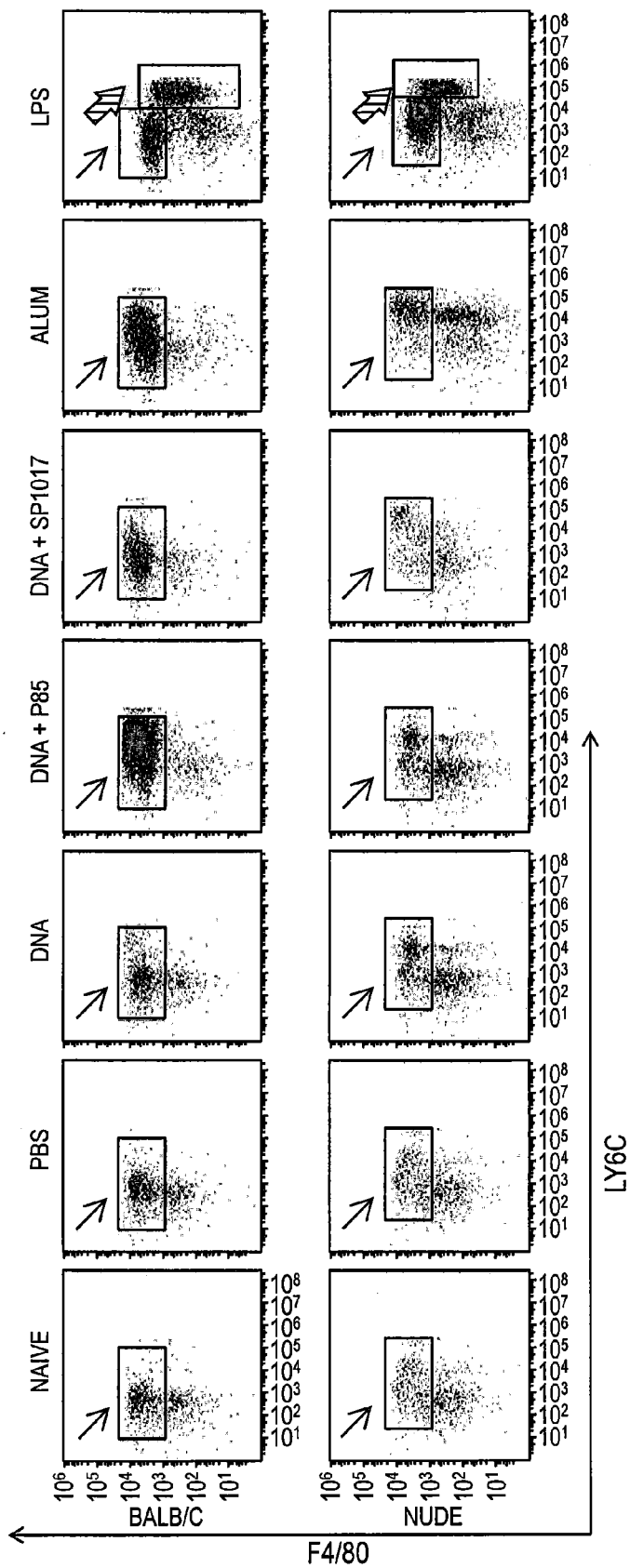
Figure 18:
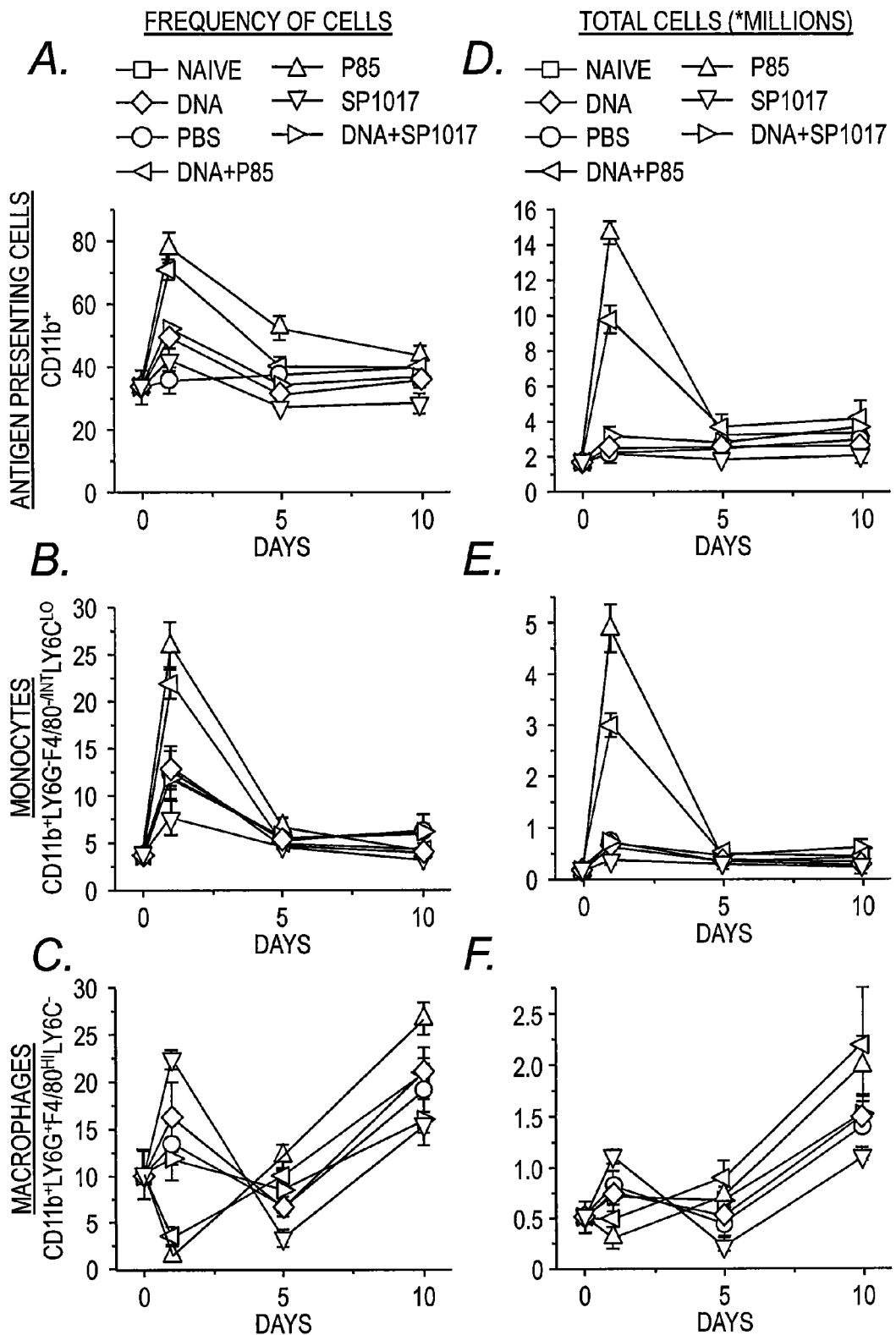
FIG. 18 shows the kinetics of immune response to various formulations. BALB/c mice were injected with 250 μl of PBS, P85 (0.3% w/v), SP1017 (2.25% w/v) alone or mixed with 50 μg naked DNA via i.p. injection. 24 h later peritoneal lavage cells were labeled with respective cell surface markers to characterize antigen presenting cells (Panels A, D), monocytes (Panels B, E) and macrophages (Panels C, F) using LSR-II flow cytometer and data analyzed by FlowJo. Data are Mean±SEM (n=3-6).

Since we hypothesized the role of monocytes/macrophages in muscle transfection, we characterized the immune response to various formulations upon direct injections in vivo. Immune response cells recruited at the site of injections (peritoneal cavity) from PBS, DNA, DNA+P85, DNA+SP1017 were compared to naïve animals. Alum and LPS were used as positive controls. Flow cytometer analysis (FIG. 17; dot plots) confirmed recruitment of anti-inflammatory or M2 monocytes)(CD11b$^+$Ly6G$^-$F4/80$^{-/int}$Ly6C$^{lo}$) in all groups in addition to inflammatory or M1 monocytes (CD11b$^+$Ly6G$^-$F4/80$^{-/int}$Ly6C$^{hi}$) in the LPS group only. Moreover, anti-inflammatory monocyte response was abolished in DNA+P85 group in nude mice which explained the reason for strain dependent increase in gene expression (previously published data). Similar to control groups (naïve and PBS injected), naked DNA alone did not recruit more monocytes at the site of injection unless formulated with P85 that helped recruit anti-inflammatory monocytes (black arrows) similar to adjuvant alum (FIG. 17, Panel B). In contrast, LPS recruited both anti-inflammatory and inflammatory (red arrow) monocytes (FIG. 17, Panel B). Kinetics of monocyte influx revealed peak monocyte recruitment between 24-48 h post injection (FIG. 18).

Figure 19:
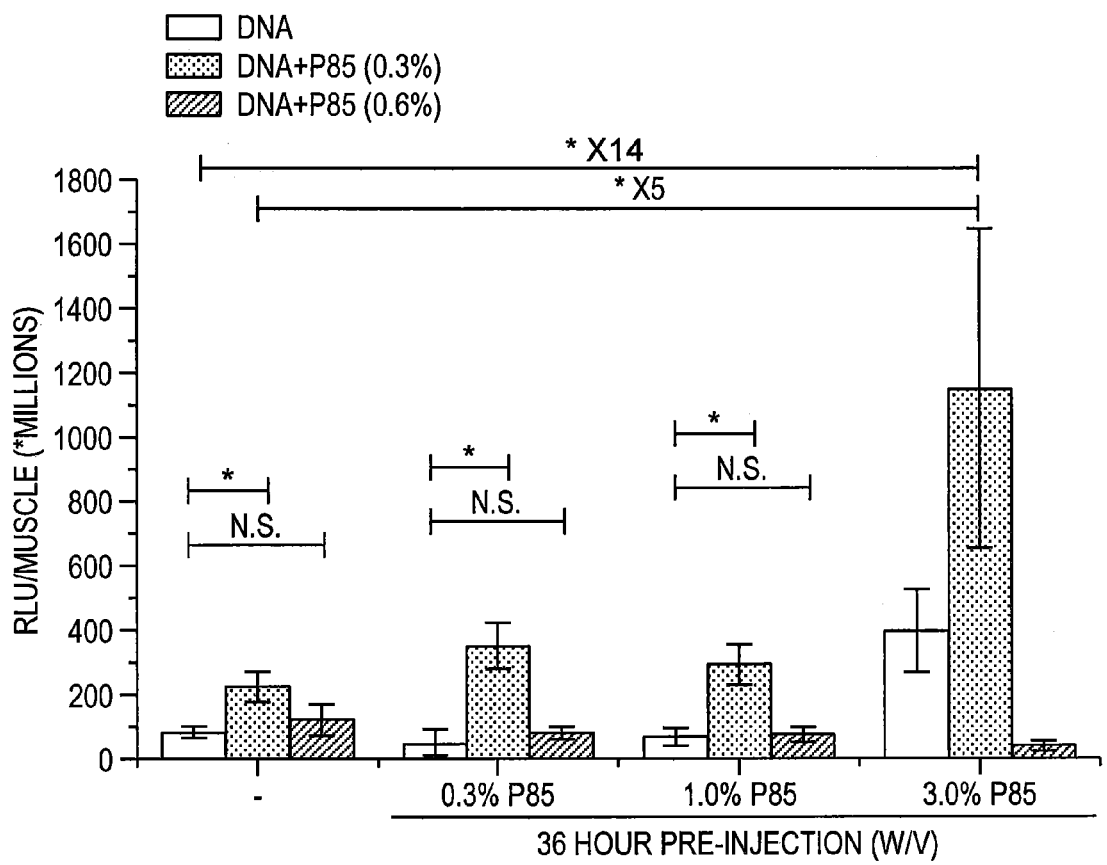
FIG. 19 shows the effect of pre-injection of P85 on DNA transfer to muscle. Bilateral tibialis anterior were injected with 50 μl formulation of naked DNA alone, DNA mixed with 0.3% P85 or 0.6% P$5 36 h after increasing concentrations of P85 (0.3%, 1.0% and 3.0%) and luciferase activity was determined in tissue homogenates after 4 days post DNA injections. Data represents Mean±SEM of 6-8 data points (n=3-4) and statistical significance was measured using student's t test at *p<0.05.

Finally, we developed a pre-injection model wherein, we induced monocyte recruitment before DNA injections to further increase muscle transfection efficiencies. Various concentrations of P85 were injected 36 h before DNA alone or DNA+P85 injections in the same muscles. After 4 days, luciferase assay was used to quantify gene expression levels in groups with and without pre-injection. Pre-injection with 3% P85 followed by DNA+P85 (0.3%) resulted in highest gene expression levels (FIG. 19).

EXAMPLE 6

Figure 20:
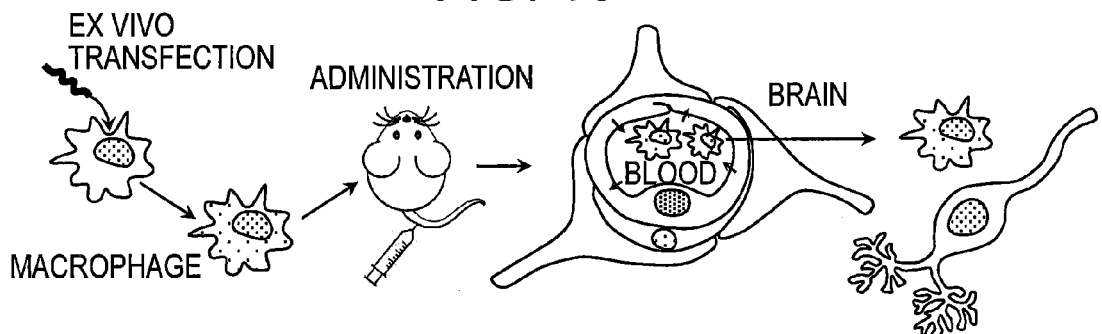
FIG. 20 shows a schematic representation of macrophage-mediated drug delivery approach. Autologous macrophages were transfected with GDNF-encoding pDNA ex vitro and systemically administered into mice with brain inflammation. Driven by chemotaxis, genetically-modified cell-carriers home the inflamed brain tissues, and deliver the expressed neurotrophic factor to the dopaminergic neurons protecting them from toxic insults. The release of overexpressed GDNF in exosomes protected it against proteases degradation, facilitated the neurotrophin transfer into target neurons and as a result, improved therapeutic efficacy of this drug formulation.

Here we report using genetically-modified autologous macrophages for active targeted delivery of GDNF to the inflamed brain. The overall scheme of these investigations is depicted in FIG. 20. Macrophages were transfected ex vivo to produce GDNF, and administered intravenously in mice with PD model. This resulted in significant increases in dopaminergic neurons survival and decreases in inflammation in SNpc. Using living cells as drug carrier systems offers several advantages over common drug administration regimens. These include active targeted drug transport to the disease sites; prolonged drug half-lives; time-controlled drug release; and diminished drug immunogenicity and cytotoxicity profiles.

Our earlier studies suggest cell-carriers offer distinct advantages over standard drug administration regimens by providing disease-specific homing, sustained on-site drug delivery, and improved therapeutic efficacy (Batrakova et al., Expert Opin Drug Deliv 8: 415-433 (2011); Batrakova et al., Bioconjug Chem 18: 1498-1506 (2007); Brynskikh et al., Nanomedicine (Lond) 5: 379-396 (2010); Haney et al., Nanomedicine (Lond) 7: 815-833 (2012); Haney et al., Plos One 8: e61852 (2013); Haney et al., Nanomedicine (Lond) 6: 1215-1230 (2011); Klyachko et al., Nanomedicine (Lond) (2013); Zhao et al., Nanomedicine (Lond) 6: 25-42 (2011); Zhao et al., J Nanomed Nanotechnol S4 (2011)). Based on our previously developed cell-mediated drug delivery system, present work utilized genetically-modified macrophages for active targeted delivery of a potent neurotrophin, GDNF. Of note, genetically-modified macrophages released exosomes with incorporated GDNF that may facilitate GDNF transport into the target cells and preserve it against degradation. Exosomes are nanosized vesicles secreted by a variety of cells, in particular, cells of the immune system: dendritic cells (Thery et al., Curr Protoc Cell Biol Chapter 3: Unit 3 22 (2006)), macrophages (Bhatnagar et al., Blood 110: 3234-3244 (2007)), B cells (Clayton et al., J Cell Sci 118: 3631-3638 (2005)), and T cells (Nolte-'t Hoen et al., Blood 113: 1977-1981 (2009)). These extracellular vesicles were initially thought to be a mechanism for removing unneeded proteins. Recent studies revealed, they are actually specialized in long-distance intercellular communications facilitating transfer of proteins (Johnstone, Biochem Cell Biol 70: 179-190 (1992)), functional mRNAs and microRNAs for subsequent protein expression in target cells (Zomer et al., Commun Integr Biol 3: 447-450 (2010); Valadi et al., Nat Cell Biol 9: 654-659 (2007)). To shuttle their cargo, exosomes can attach by a range of surface adhesion proteins and specific vector ligands (tetraspanins, integrins, CD11b and CD18 receptors), and fuse with target cellular membranes delivering their payload (Thery et al., Curr Protoc Cell Biol Chapter 3: Unit 3 22 (2006); Thery et al., Nat Rev Immunol 9: 581-593 (2009)). Indeed, exosomes, comprised of cellular membranes, have an exceptional ability to interact with target cells. Furthermore, the exosomal surface is rich with tetraspanins and integrins (Thery et al., Curr Protoc Cell Biol Chapter 3: Unit 3 22 (2006); Thery et al., Nat Rev Immunol 9: 581-593 (2009); Rana et al., Int J Biochem Cell Biol 44: 1574-1584 (2012)) that facilitate the attachment of exosomal carriers to the plasma membrane of target cells. Thus, we demonstrated here that exosomes showed an extraordinary ability to abundantly adhere and overflow neuronal cells as was visualized by confocal microscopy. This mechanism is likely to play a significant role in GDNF protection, increasing the blood circulation time, reducing immunogenicity, and facilitation of the neurotrophin transfer across the BBB and into target neurons. The present data indicate intrinsic properties of macrophages can overcome the limitations of current common therapies, alleviate and reverse the symptoms, and may ultimately improve the quality of life of patients with various neurodegenerative disorders.

Materials and Methods

Plasmids

The gWIZ™ high expression vectors encoding the reporter gene green fluorescent protein (GFP) (gWIZ™GFP) under control of an optimized human cytomegalovirus (CMV) promoter followed by intron A from the CMV immediate-early (IE) gene were used throughout the study (Gene Therapy Systems, San Diego, Calif.). Human GDNF cDNA (NM_199234) was provided by OriGene (Rockville, Md.). All plasmids are expanded in DH5α *E. coli* and isolated using Qiagen endotoxin-free plasmid Gigaprep kits (Qiagen, Valencia, Calif.) according to the supplier's protocol.

Reagents

GenePORTER 3000 transfection agent was purchased from AMS Biotechnology, England). Lipopolysaccharides (LPS), 6-hydroxydopamine (6-OHDA), and Triton X-100 were purchased from Sigma-Aldrich (St. Louis, Mo., USA). A lipophilic fluorescent dye, 1,1'-dioctadecyl-3,3,3',3'-tetramethylindo-carbocyanine perchlorate (DIL), was purchased from Invitrogen (Carlsbad, Calif.). Interferon gamma (INT-γ), and murine macrophage colony-stimulating factor (MCSF) were purchased from Peprotech Inc (Rocky Hill, N.J.).

Cells

Raw 264.7, a mouse macrophage cell line, was purchased from ATCC (cat #TIB-71), and cultured in Dulbecco's Modified Eagle's Media (DMEM) (Invitrogen, Carlsbad, Calif., USA) supplemented with 2.5% horse serum and 15% FBS. Neuronal PC 12 rat adrenal pheochromocytoma cell line was obtained from ATCC, and cultured in Dulbecco's modified Eagle medium (Hyclone, Utah, USA) supplemented with 10% FBS, and 1% (v/v) of both penicillin and streptomycin. The cells were grown in an incubator with optimal culture conditions of 37° C. and 5% $CO_2$, and the medium was routinely replaced every 2-3 days.

Animals

BALB/C female mice (Charles River Laboratories, USA) eight weeks of age were treated in accordance to the Principles of Animal Care outlined by National Institutes of Health and approved by the Institutional Animal Care and Use Committee of the University of North Carolina at Chapel Hill.

Transfection of Macrophages with GDNF-Encoding pDNA and Differentiation Toward M2 Regenerative Subtype Macrophages were incubated with a mixture of 13.6 µg GFP, or GDNF pDNA and GenePORTER 3000 in serum free media for four hours. Following incubation, an equal volume of full media containing 20% FBS was added bringing final serum concentration to 10%. To exclude the possibility that cell death explains the release of GDNF and GFP, percentage of live macrophages on the fourth day after transfection was accounted by FACS. Transfected cells were collected, washed, stained with Alexa 488 LIVE/DEAD dye according to manufacturer's protocol, and the amount of accumulated LIVE/DEAD dye was assessed.

To promote specific cell differentiation, Raw 264.7 macrophages were cultured in the presence of: (i) Interleukin 4 (IL-4) (to promote M2 anti-inflammatory subtype); or (ii) Interferon gamma (IFN-γ) and LPS (to obtain M1 pro-inflammatory subtype). For M2 subset differentiation, macrophages were supplemented with IL 4 (20 ng/ml) for 48 hours. For M1 subset differentiation, the cells were cultured in the mixture of IFN-γ (20 ng/ml) and LPS (100 ng/ml) for 48 hours. Following the incubation, media was replaced with a mixture of antibodies to mannose receptor (M2 type marker, anti-CD 206, BD Bioscience, 1 µg/ml), and antibodies to CD86 (M1 type marker, anti-CD 86, BD Bioscience, 2 µg/ml). The cells were incubated with the antibodies for 1 hour, washed, fixed, and examined by confocal microscopy as described below (CD 86, λ=405 nm, and CD 206, λ=647 nm). An overexpression of specific markers related to M1 or M2 subset of macrophages upon cell differentiation was confirmed by RT-PCR.

Isolation of Exosomes

Conditioned media from genetically-modified Raw 264.7 macrophages grown on T-75 flasks ($20 \times 10^6$ cells/flask) was collected, and exosomes were isolated using ultra centrifugation (Thery et al., Curr Protoc Cell Biol Chapter 3: Unit 3 22 (2006)). In brief, the culture supernatants were cleared of cell debris and large vesicles by sequential centrifugation at 300×g for 10 min, 1000×g for 20 min, and 10,000×g for 30 min, followed by filtration using 0.2-µm syringe filters. Then, the cleared sample was spun at 100,000×g for 1 hour to pellet the exosomes, and supernatant was collected. The collected exosomes ($10^{11}$-$10^{12}$ exosomes/flask) were washed twice with PBS. To avoid contamination of the FBS-derived exosomes, FBS was spun at 100,000×g for 2 hours to remove exosomes before use. The recovery of exosomes was estimated by measuring the protein concentration using the Bradford assay and by Nanoparticle Tracking Analysis (NTA). The obtained exosomal fraction was re-suspended in PBS (500 µl, 1 mg/mL total protein), and characterized for size and polydispersity by Dynamic Light Scattering (DLS) and Atomic Force Microscopy (AFM). The obtained exosomal fraction was evaluated for protein content.

Western Blot Analysis

Western blots were utilized to evaluate the presence of GDNF in transfected macrophages as well as in exosomes secreted by GDNF- or empty vector-transfected macrophages. Genetically-modified macrophages and exosomes isolated from the conditioned media were treated with lysis buffer (1% Triton X-100) and protease inhibitors (Sigma) and protein concentration was determined by BCA assay. Samples were mixed with 2× SDS sample buffer, boiled for 5 min and then separated on a precast 4-20% SDS-PAGE gel (BioRad, USA). Proteins were transferred to nitrocellulose membranes and GDNF was visualized with sheep polyclonal antibodies to GDNF (Millipore, AB5252, 1:2000 dilution) and secondary antibodies donkey anti-sheep IgG-HRP (Jackson ImmuneResearch; 1:5000 dilution). To correct for loading differences in cellular lysates and exosomal fractions, the levels of proteins were normalized to constitutively expressed β-actin in cells with goat polyclonal antibodies to β-actin (Abcam, ab8229; 1:500 dilution); and TSG101 in exosomes with goat polyclonal antibodies to TSG101 (Santa Cruz, SC6037; 1:200 dilution). Furthermore, for the characterization of different subtypes of polarized macrophages and released from them exosomes, membranes with corresponding transferred protein bands from macrophages or exosomes were blotted with rabbit polyclonal antibodies to CD63 (Santa Cruz, SC15363; 1:200 dilution), iNOS (Santa Cruz, SC650; 1:200 dilution), Arg1 (Santa Cruz, SC18351; 1:200 dilution) and CD206 (Santa Cruz, SC6037; 1:200 dilution) overnight at 4° C., and incubated with appropriate HRP-conjugated secondary antibodies: goat anti-rabbit IgG-HRP (Santa Cruz, SC2004; 1:2500 dilution), or donkey anti-goat IgG-HRP (Santa Cruz, SC2020; 1:5000 dilution). Membranes were washed and the expression levels were visualized with chemiluminescent substrate (Thermo Scientific) and a FluorChem E imaging system (Protein Simple). Specific protein bands were quantitated by densitometry (Bio-Rad Laboratories, Hercules, Calif.).

RT-PCR Analysis

Total RNA of macrophages as well as exosomal RNA was extracted using RNeasy mini kit (Qiagen, CA, USA) according to manufacturer's instructions. Residual genomic DNA of macrophages and exosomes was removed by incubating with Rnase-free DNase set (Qiagen). RNA was analyzed and quantified using nanodrop 2000c (Thermo Scientific, USA). As quality controls of RNA samples purity from contaminating DNA and chaotropic salts was obtained by absorbance Ratio A260/A280 and A260/A230, respectively. RNA (1 µg) isolated from resting and polarized macrophages cells and their respective exosomes was reverse transcribed with Superscript III First-Strand synthesis system for RT-PCR (Invitrogen, CA, USA) according to manufacturer's protocol. To quantify mRNA levels, quantitative reverse transcription PCR was performed using an ABI StepOne Plus Detection System (Applied Biosystems, MA, USA). TaqMan PCR Universal Master Mix and Expression Assays were from Applied Biosystems. Assay IDs: iNOS Mm00440502_m1, CD206 Mm00485148_m1 and CD63 Mm01966817_g1. CD63 was used as exosomal marker and CD11b as macrophage cells marker.

Confocal Microscopy Studies

To visualize exosomal accumulation in target neurons, Raw 264.6 macrophages were transfected with GDNF-encoding DNA, and cultured in exosome-free media for two days. Exosomes were isolated from macrophage conditioned media by ultracentrifugation, and stained with the lipophilic fluorescent dye, DIL (red). PC12 neurons were cultured with DIL-labeled exosomes or PLGA nanoparticles (as a control) for three days, washed with PBS, and stained with phallodin for actin microfilaments (green). The accumulation levels were examined by confocal microscopy.

To track systemically injected macrophages in the inflamed brain, macrophages were transfected with OFP-encoding DNA as described above. For 6-OHDA intoxications, mice were stereotactically injected with 6-OHDA solution (10 µg 6-OHDA in 0.9% NaCl with 0.02% ascorbic acid), flow rate of 0.1 µL/min into the striatum (AP: +0.5; L: −2.0 and DV: −3.0 mm) (Zhao et al., J Nanomed Nanotechnol S4 (2011)). Animals with brain inflammation induced were injected with OFP-expressing Raw 264.7 macrophages on day twenty one after intoxication with 6-OHDA via the intrajugular vein (i.v.). Two days later, animals were sacrificed and perfused as described (Zhao et al., J Nanomed Nanotechnol S4 (2011)), brains were removed, washed, post-fixed in 10% phosphate-buffered paraformaldehyde, and evaluated by confocal microscopy.

Immunohistochemical and Stereological Analyses

6-OHDA-intoxicated mice were i.v. injected with PBS, or GDNF-transfected macrophages, or macrophages transfected with empty vector 48 hours after intoxication. Twenty four days later, animals were sacrificed, perfused; brains were removed, washed, post-fixed, and immunohistochemical analysis was performed in 30 µm thick consecutive coronal brain sections (Brynskikh et al., Nanomedicine (Lond) 5: 379-396 (2010)). For detection of microglia activation, tissue sections were incubated with primary monoclonal rat anti mouse anti-CD11b antibodies (AbD Serotec, Raleigh, N.C.) 1:500 dilution), and secondary biotinylated goat anti-rat antibodies (Vector Laboratories, Burlingame, Calif., 1:200 dilution). For the assessment of neuroprotection effect, tyrosine hydroxylase (TH) staining was used to quantitate numbers of dopaminergic neurons (Tieu et al., J Clin Invest 112: 892-901 (2003)). The total number of TH-positive SN neurons and CD11b-positive microglia cells were counted by using the optical fractionator module in StereoInvestigator software (MicroBrightField, Inc., Williston, Vt.) (Brynskikh et al., Nanomedicine (Lond) 5: 379-396 (2010)).

Behavioral Tests

For the traditional constant speed rotarod test, mice were trained and tested as previously described with slight modifications (Rozas et al., Brain Res Brain Res Protoc 2; 75-84 (1997)). 6-OHDA-intoxicated mice were i.v. injected with PBS, or GDNF-transfected macrophages 48 hours after intoxication and the latency to fall from the rotarod was determined at three speeds (4, 5, and 7 rpm). Healthy mice i.c. injected with PBS were used as a control (Keshet et al., J Comp Neurol 504: 690-701 (2007)). For apomorphine test, the animals were injected with apomorphine (0.05 mg/kg, s.c.) and rotations were scored every 10 min for 90 min (Papathanou et al., Eur J Neurosci 33: 2247-2254 (2011)).

Statistical Analysis

For the all experiments, data are presented as the mean±SEM. Tests for significant differences between the groups in in vitro experiments investigating transfection of macrophages, as well as in in vivo evaluations of therapeutic effects of different drug formulations were performed using a one-way ANOVA with multiple comparisons (Fisher's pairwise comparisons) using GraphPad Prism 5.0 (GraphPad software, San Diego, Calif., USA). A standard T-test was performed when only two groups (for example, for the evaluation of expression levels of specific proteins by western blot) were compared. A minimum p value of 0.05 was chosen as the significance level for all tests.

Results

Figure 21:
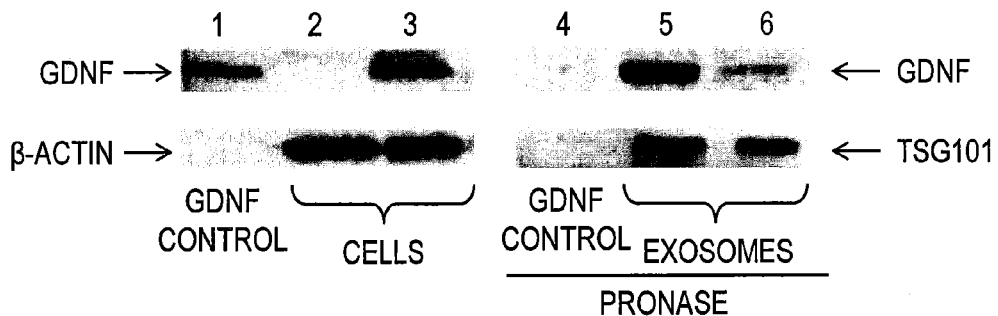
FIG. 21 shows expression of GDNF by genetically-modified macrophages. Raw 264.7 macrophages were pre-transfected with GDNF-encoding pDNA and GenePorter 3000 reagent for 4 hours. Then, exosomes were collected from concomitant macrophages media for 24 hours, and GDNF levels in cellular lysates (lines 2-3) and in exosomes (lines 5-6) were examined by western blot. Commercially available GDNF (line 1) served as a positive control. Significant amount of GDNF was detected in the cells (line 3) and exosomes released from GDNF-transfected macrophages (line 5), but not in macrophages transfected with empty vector (line 2). Expressed GDNF was protected in exosomes against degradation by pronase (line 5), while control GDNF was degraded at these conditions (line 4). Destruction of exosomes by sonication eliminated their protective effect (line 6). β-actin and TSG101 served as controls for cell lysates and exosomes, respectively.

Expression of GDNF in Genetically-Modified Macrophages and Released from them Exosomes The optimal conditions that provide for high levels and duration of therapeutic proteins expression in macrophages identified previously (Haney et al., Plos One 8: e61852 (2013)) were used to transfect Raw 264.7 macrophages. Next, exosomes were collected from conditioned macrophages media for 24 hours, and the expression of the encoded protein in the in cellular lysates and exosomes were evaluated by western blot (FIG. 21). Significant amounts of GDNF was detected in the cells (line 3) and exosomes released from GDNF-transfected macrophages (line 5), but not in macrophages transfected with empty vector (line 2). Noteworthy, the expressed GDNF was protected in exosomes against degradation by pronase (line 5); while control GDNF was degraded at these conditions (line 4). Destruction of exosomes by sonication eliminated their protective effect against proteases degradation (line 6). The average size for exosomes released from GDNF-transfected macrophages (96.0±9.1 nm) was slightly greater than those released from non-transfected macrophages (90.5±3.4 nm).

Effects of GDNF-Transfected Macrophages on Axonal Growth In Vitro

Figure 22:
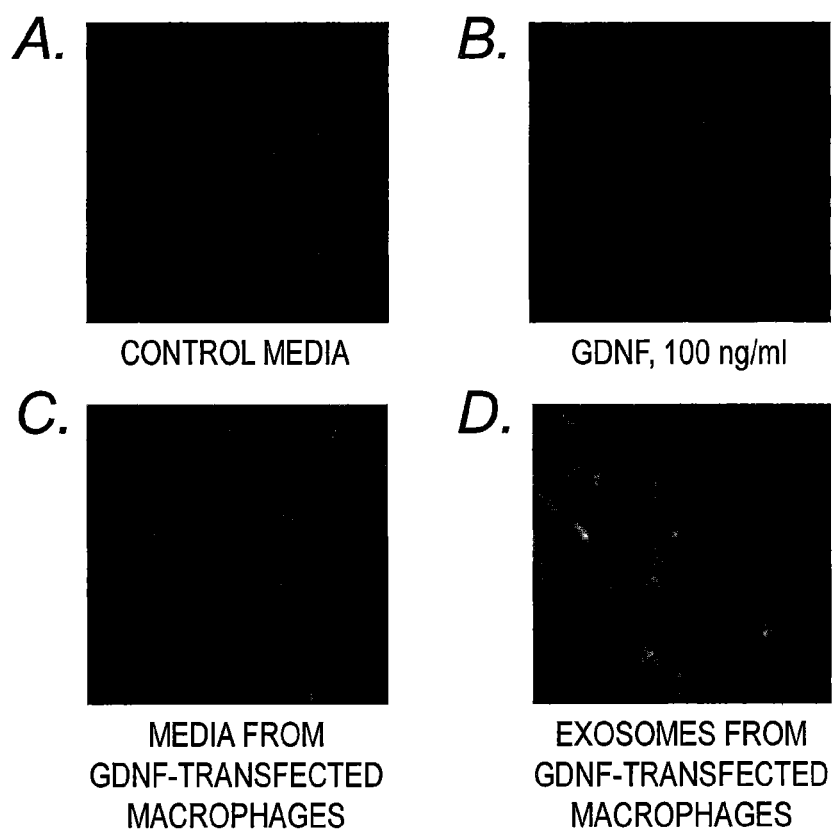
FIG. 22 shows the effect of exosomes released from GDNF-transfected macrophages on the axonal growth in PC12 neurons. PC12 neurons were cultured for 3 days in: (Panel A) control media without GDNF; (Panel B) in the presence of 100 ng/ml GDNF; or supplemented with (Panel C) conditioned media collected from GDNF-transfected macrophages; or (Panel D) exosomes isolated from conditioned media released from GDNF-transfected macrophages. Exosomes were fluorescently labeled with lipophilic dye, DIL (red) before the addition to the neurons (Panel D). Following incubation, the cells were washed with PBS, and stained with phallodin for actin microfilaments (green). Confocal images revealed the pronounced development of axons upon treatment with media (Panel C) and especially exosomes (Panel D) released from GDNF-transfected macrophages. The bar: 20 μm.

A profound therapeutic effect of GDNF released from pre-loaded M2 macrophages in vitro was demonstrated in PC12 neurons that are known to express GDNF receptor (FIG. 22). Neurons were cultured for 72 hours in: (Panel A) control media without GDNF; (Panel B) media supplemented with high concentration of commercially available GDNF ng/ml); (Panel C) conditioned media collected from GDNF-transfected macrophages, or (Panel D) exosomes isolated from GDNF-transfected macrophages. Following the incubation, the cells were stained with phallodin for actin microfilaments (green) and DAPI for cell nucleus (blue). In parallel, exosomes were stained with a lipophilic fluorescent dye, DID (red). Confocal images revealed the pronounced axonal growth in neurons cultured with conditioned media from GDNF-preloaded macrophages (FIG. 22, Panel C), and especially with exosomes released from pre-transfected macrophages (FIG. 22, Panel D), suggesting the neurotrophin was released from the cell-carriers in a functional state. The effects were greater than those caused by a high dose of commercially-available GDNF (FIG. 22, Panel B). It is likely, similar to catalase-transfected macrophages (Haney et al., Plos One 8: e61852 (2013)), exosomes with incorporated overexpressed neurotropic factor promote GDNF transfer, and secure its efficient accumulation and favorable intracellular localization in target neurons.

Figure 23:
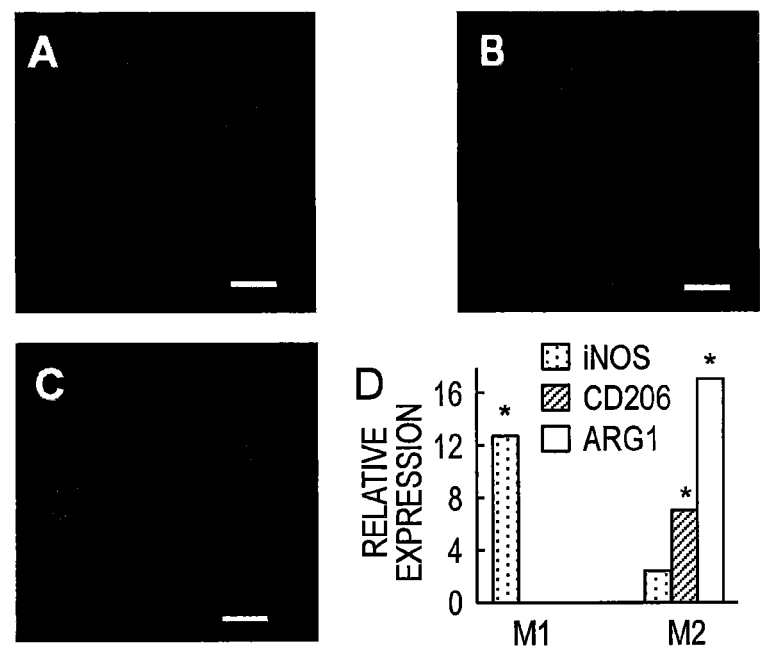
FIG. 23 shows the differentiation of macrophages toward "alternatively" activated M2 subtype. Raw 264.7 macrophages were cultured in the presence of: (Panel A) Interferon gamma (IFN-γ) and lipopolysaccharides (LPS) for M1 pro-inflammatory subtype; or (Panel B)) Interleukin 4 (IL 4) for M2 anti-inflammatory subtype for two days. Then, the cells were stained with a mixture of antibodies to CD 86 (green) and mannose receptor CD206 (red) for M1 and M2 phenotype, respectively, and examined by confocal microscopy. Macrophages differentiated in the presence of INF-γ/LPS showed high expression of CD86, but low if any mannose receptor levels indicating classically activated M1 subtype (Panel A). In contrast, cells differentiated in the presence of IL-4 showed high expression of mannose receptor, and low expression of CD 86 that is attributed to M2 macrophages (B). Non-differentiated Mo macrophages served as a control (Panel C). Bar: 20 μm. RT-PCR studies confirmed elevated levels of inducible Nitric Oxide Synthases (iNOS) mRNA in M1 cells, and high levels of CD206 and Arginase 1 (Arg1) mRNA in M2 macrophages (Panel D).

Differentiation of Macrophages and Using an Alternatively Activated Neuroregenerative M2 Subtype To enhance the therapeutic effects of neurotrophins and avoid the pro-inflammatory neurotoxic effects of classically-activated M1 macrophages (Kigerl et al., J Neurosci 29: 13435-13444 (2009)), Raw 264.7 macrophages were differentiated to M2 regenerative subtype. For this purpose, macrophages were cultured in the presence of Interleukin 4 (IL 4) for M2 subtype; or Interferon gamma (IFN-γ) and lipopolysaccharides (LPS), as a negative control for M1 pro-inflammatory subtype. The obtained subsets of macrophages were characterized by confocal microscopy (FIG. 23, Panels A-C) and RT-PCR (FIG. 23, Panel D). Mannose receptor (CD206), and Arginase 1 (Arg1) were chosen as principal markers form identifying M2 macrophages subtype. Levels of inducible Nitric Oxide Synthases (iNOS, CD86) were examined as marker of M1 macrophages subtype. Noteworthy, Arg1 and iNOS (Suschek et al., Curr Mol Med 4: 763-775 (2004)) were demontrated to have anti-inflammatory and pro-inflammatory properties, respectively.

Macrophages differentiated in the presence of INF-γ/LPS demonstrated considerable expression of CD 86, and low, if any, levels of mannose receptor (FIG. 23, Panel A) that is indicative for classically activated pro-inflammatory M1 subtype. In contrast, Raw 264.7 macrophages differentiated in the presence of IL-4 showed high expression levels of mannose receptor, and low, if any, expression of CD 86 (FIG. 23, Panel B) that is indicative for "alternatevly activated" anti-inflammatory macrophages. Non-activated Mo macrophages showed low, if any expression of both CD86 and CD206 receptors (FIG. 23, Panel C). Noteworthy, the polarization to different macrophages subtypes altered the cells morphology. RT-PCR studies confirmed elevated levels of iNOS mRNA in M1 cells, and high levels of CD206 and Arginase 1 (Arg1) mRNA in M2 macrophages (FIG. 23, Panel D).

Figure 24:
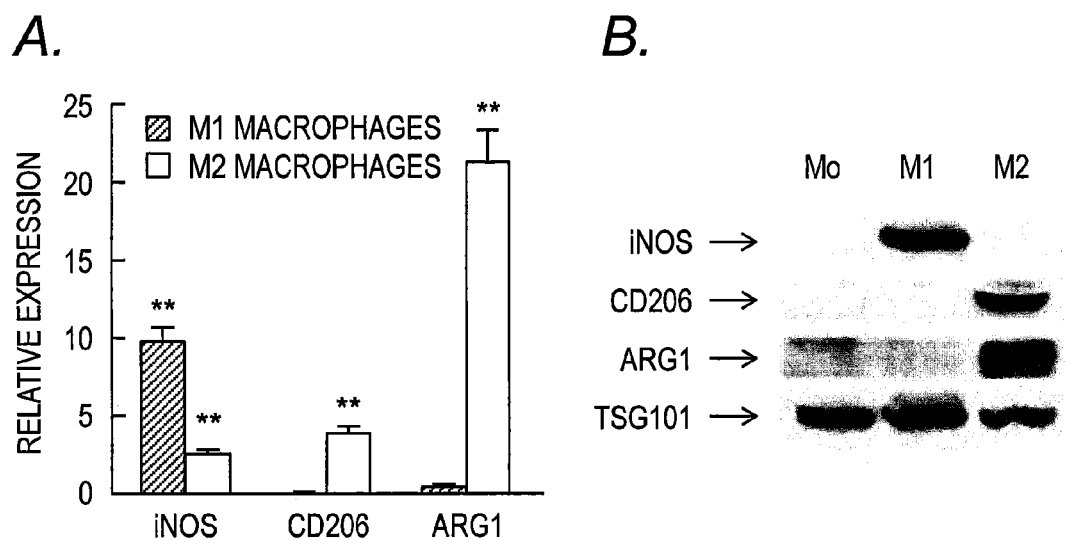
FIG. 24 shows the characterization of exosomes released from differentiated subtypes of macrophages. Exosomes were isolated from conditional media of differentiated macrophages and examined for the presence of specific markers by RP-PCR (Panel A) and western blot (Panel B). Expression of Arg1 and CD206 mRNA and protein (markers for M2 subtype) was detected in exosomes originated from M2 macrophages, but not in those secreted from M1 macrophages. In contrast, expression of iNOS mRNA and protein was detected in exosomes released from M1 macrophages, but not in those secreted by M2 macrophages. TSG101 was used as house-keeping protein for exosomes. Values are means±SEM (N=4), and p<0.05 compared with the expression levels in Mo macrophages.

Next, we hypothesized that exosomal content, at least in part, should reflect the content of parental macrophages. Thus, exosomes released from M2 macrophages may exhibit neuroprotective and regenerative properties by themselves. A presence of Arg1 mRNA and Arg1 protein that is indicative for M2 macrophages subtype was evaluated by RT-PCR (FIG. 24, Panel A) and western blot analyses (FIG. 24, Panel B). The obtained data confirmed exosomes secreted by M2 regenerative macrophages, but not M1 pro-inflammatory macrophages showed high levels of Arg1 and CD206 mRNA and Arg1 protein. In contrast, expression of iNOS mRNA and protein (marker for M1 macrophages) was detected in exosomes released from M1 macrophages, but not in those secreted by M2 macrophages. This approach was utilized further to differentiate the cell-carriers towards the M2 phenotype prior to the infusion to capitalize on the beneficial properties afforded by alternatively activated M2 macrophages in the context of PD, and minimize the potential of the cells converting to the pro-inflammatory M1 subtype.

Figure 25:
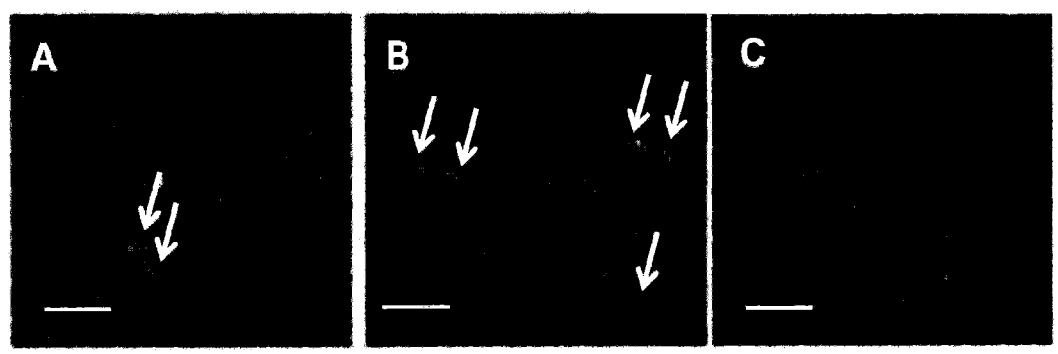
FIG. 25 shows the recruitment of UP-expressing M2 macrophages to SNpc in 6-OHDA-intoxicated mice. Macrophages were transfected with GFP-encoding pDNA and stained with primary antibodies to CD206, a marker for M2 macrophages, and secondary fluorescently-labeled anti-Mouse-IgG-atto 647N (red). BALB/c mice were i.c. intoxicated with 6-OHDA into SNpc. Twenty one days later, the animals were i.v. injected with GFP-expressing RAW 264.7 macrophages (green, 5×10$^6$ cells/mouse in 100 μl). Twenty four hours later mice were sacrificed, and perfused with PBS and 4% PFA. Brains were frozen, sectioned with a cryostat (10 μm thick), and examined by confocal microscopy (60× magnification) (Panels A, B). Healthy mice without brain inflammation (with PBS i.c. injections) were used as a control group (Panel C). Slides were stained for expression of mannose receptor (CD206 antibodies). Co-localization of GFP-expressing macrophages and CD206 antibodies to mannose receptor manifested in yellow staining (arrows) confirmed presence of significant amounts of the M2 genetically-modified cells in the intoxicated brain endothelial microvessels (Panel A), and parenchyma (Panel B). No fluorescence in the healthy brain was found (Panel C) indicating that systemically administered Raw 264.7 macrophages did not cross the BBB in the absence of brain inflammation. The bar: 20 μm.

Systemically-Administered M2 Macrophages Home Inflamed Brain Tissues and Sustain their Phenotype in Brain Tissues Raw 264.6 macrophages were transfected with GFP-encoding pDNA, and then differentiated to M2 regenerative subtype as described above. BALB/c mice were i.c. intoxicated with 6-OHDA into SNpc. Twenty one days later (at the peak of inflammation), mice were systemically injected with GFP-expressing macrophages ($5 \times 10^6$ cells/mouse in 100 µl). Twenty four hours later, the mice were sacrificed, and perfused with PBS and 4% PFA. Healthy mice without brain inflammation were used as a control group. Brain slides were stained with primary antibodies to CD 206, a marker for mannose receptor attributed to M2 subtype of macrophages. Confocal images of brains sections indicate systemically infused macrophages home to the inflamed brain and localize around brain endothelial microvessels (FIG. 25, Panel A), and parenchyma (FIG. 25, Panel B). Co-localization of GFP-expressing macrophages (green) and CD206 staining (red) manifested in yellow confirmed, the macrophages sustain their M2 phenotype in the intoxicated brain. No macrophages were found in healthy brain (FIG. 25, Panel C) indicating the cells do not cross the BBB in the absence of inflammation.

Macrophage-Mediated Neuroprotection in PD Mice

Figure 26:
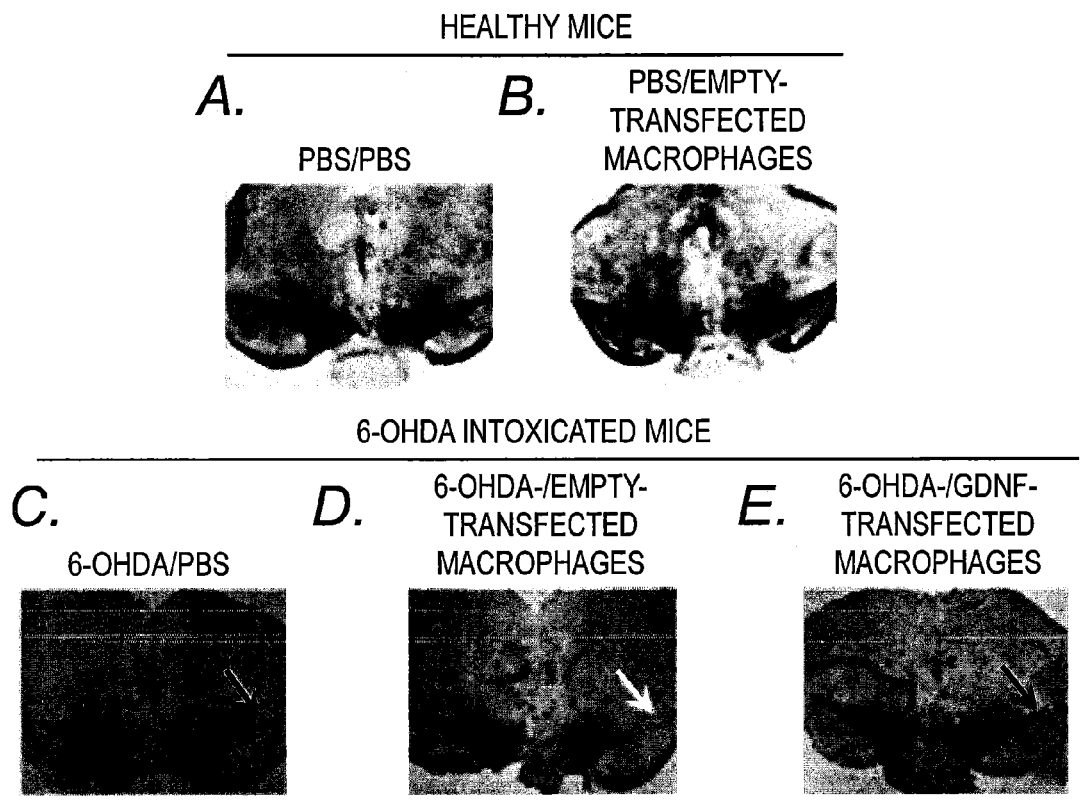
FIG. 26 shows the neuroprotective effects of GDNF-transfected macrophages in PD mouse model. BALB/c mice were i.c. injected with 6-OHDA. Forty eight hours later, animals were i.v. injected with GDNF-transfected or empty-transfected macrophages, or PBS, and 21 days later they were sacrificed, and mid-brain slides were stained for expression of TH, a marker for dopaminergic neurons. Whereas 6-OHDA treatment caused significant neuronal loss in SNpc (red arrow), administration of GDNF-transfected macrophages dramatically increased neuronal survival (blue arrow). Administration of empty-vector transfected macrophages did not affect the number of dopaminergic neurons in healthy mice, and shows mild effect on increased neuronal survival in PD mice (white arrow).
Figure 27:
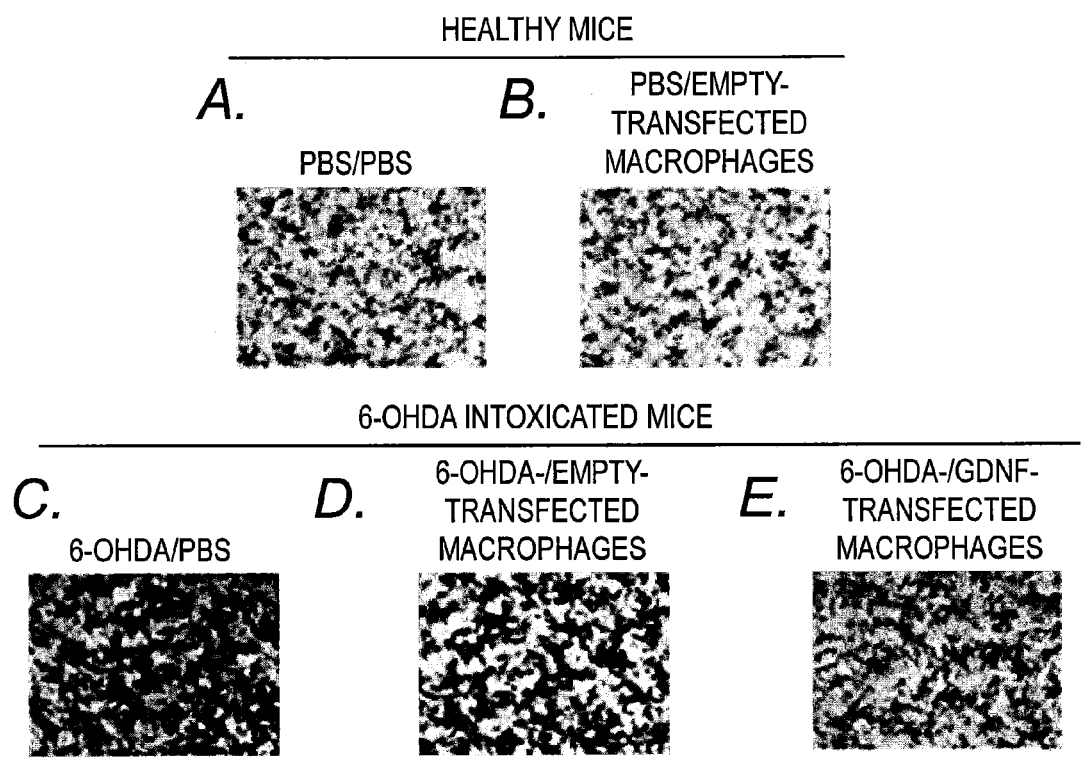
FIG. 27 shows that GDNF-transfected macrophages reduce neuro-inflammation in PD mice. BALB/c mice were i.c. injected with 6-OHDA. Forty eight hours later, animals were i.v. injected with GDNF-transfected or empty-transfected macrophages, or PBS, and 21 days later they were sacrificed, and mid-brain slides were stained for expression of CD11b, a marker for activated microglia. A 6-OHDA-mediated intoxication up-regulated expression of CD11b by microglia within the SNpc as exhibited a more amoeboid morphology in 6-OHDA-treated mice compared to ramified microglia in PBS-treated mice. In contrast, treatment of 6-OHDA-intoxicated mice with catalase-transfected macrophages resulted in the decreased levels of CD11b compared with 6-OHDA-intoxicated control animals. Administration of empty-vector transfected macrophages did not affect the number of dopaminergic neurons in PD or healthy mice.

A potent neuroprotective effect of GDNF-transfected macrophages was demonstrated in the 6-OHDA-intoxicated mice (FIG. 26). GDNF-overexpressing Raw 264.7 macrophages were systemically administered to BALB/c mice with brain inflammation ($1 \times 10^6$ cells/100 µl) 48 hours after i.c. intoxication with 6-OHDA (PD mouse model). Non-intoxicated mice were used as healthy controls. 21 day later, mice were sacrificed, perfused, and the brain slides were stained for tyrosine hydroxylase (TH)-expressing DA neurons. I.c. intoxications of 6-OHDA caused substantial neurodegeneration in the SNpc (FIG. 26, Panel C, Table 2) compared to healthy mice (FIG. 26, Panel A, Table 2). Systemic administration of GDNF-transfected macrophages protected DA neurons against 6-OHDA intoxications (FIG. 26, Panel E, Table 2). The numbers of TH+ neurons in SNpc of 6-OHDA animals treated with (JDNF-transfected macrophages were significantly ($p<0.05$) greater than those 6-OHDA intoxicated, and then PBS-injected animals (Table 2). Noteworthy, empty-transfected macrophages slightly improved neuronal survival in PD animals, probably due to their regenerative M2 subtype, although this effect was not statistically significant (FIG. 26, Panel D, Table 2). Indeed, empty-transfected macrophages did not affect neuronal survival in healthy mice (FIG. 26, Panel B, Table 2). This signifies that GDNF-transfected macrophages can efficiently protect DA neurons against 6-OHDA-induced intoxication. The therapeutic effect of GDNF-transfected macrophages was also manifested in significant decreases in inflammation and levels of activated microglia in SNpc (FIG. 27, Table 2). Accordingly to neurodegenerative effects, 6-OHDA intoxication resulted in significant microglial activation in PD mice that was abolished by systemic administration of GDNF-transfected macrophages.

TABLE 2

Effect of GDNF-transfected macrophages on inflammation and neurodegeneration in mice with PD model [a]

| Treatment | CD11b+ (cells/mm$^2$) | | Total N of neurons [b] × 10$^3$ | |
|---|---|---|---|---|
| | PBS | 6-OHDA | PBS | 6-OHDA |
| PBS | 10.1 ± 1.2 | 90.0 ± 11 ()[c] | 5.9 ± 1.4 | 2.15 ± 0.3 () |
| GDNF-transfected macrophages | n/a | 63.5 ± 5.2 (*) | n/a | 3.3 ± 0.6 (*, #) |
| Empty-transfected macrophages | 9.8 ± 1.0 | 87.0 ± 11.1 | 5.7 ± 1.5 | 2.5 ± 0.7 |

[a] BALB/c mice were i.c. injected with 6-OHDA. Forty eight hours later, the animals were i.v. injected with various macrophage-based formulations or PBS. A control group was i.c. injected with PBS, and then 48 hours later i.v. injected with PBS.
[b] Total number of neurons was calculated in ipsilateral hemisphere.
[c] Statistical significance is shown by asterisk: $p < 0.05$ (*), and $p < 0.005$ (**) compared to mice with i.c. PBS injections followed by i.v. PBS injections (healthy controls); or $p < 0.05$ (#), compared to mice with i.c. 6-OHDA injections followed by i.v. PBS injections (PD controls). Errors are mean ± SEM, N = 7.

Figure 28:
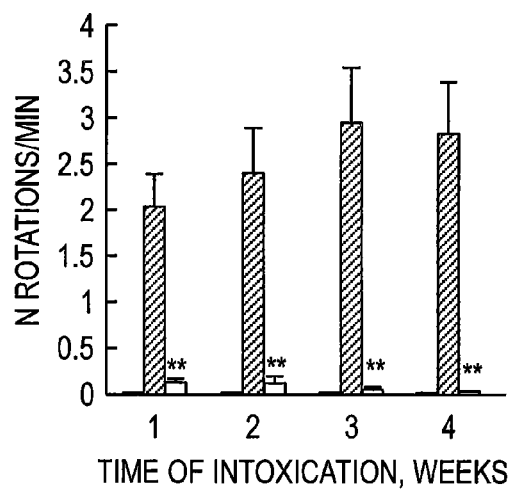
FIG. 28 shows that GDNF-transfected macrophages significantly improved motor functions in PD mouse model. 6-OHDA-intoxicated BALB/c mice were i.v. injected with GDNF-transfected macrophages (white bars), or PBS (black bars) 48 hours after the intoxication. A control group (grey bars) was i.c. injected with PBS, and then 48 hours later i.v. injected with PBS. Apomorphine (Panel A) and rotarod (Panel B) tests demonstrated statistically significant improvements in motor functions upon treatment with GDNF-carrying macrophages. Values are means±SEM (N=12), and p<0.05 compared with 6-ODHA-intoxicated mice.
Figure 28:
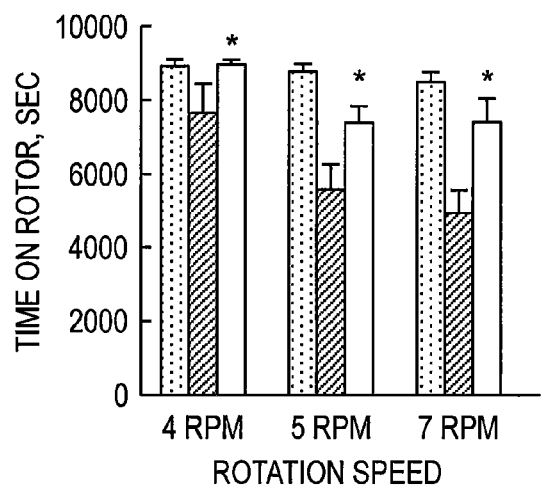

Finally, behavioral tests demonstrated statistically significant improvements in motor functions upon treatment with GDNF-transfected macrophages (FIG. 28). Specifically, the loss of dopaminergic input due to the lesion of the left nigro-striatal pathway resulted in number of full-body contralateral rotations induced by a dopaminergic agent, apomorphine (FIG. 28, Panel A). In contrast, systemic administration of genetically-modified macrophages to 6-OHDA intoxicated mice drastically ($p<0.005$) reduced number of these rotations on the seventh week following the intoxication in apomorphine test to the levels of the non-intoxicated animals. Furthermore, the motor functions were preserved by systemic administration of GDNF-transfected macrophages in 6-OHDA intoxicated animals at the levels similar to those of control non-intoxicated mice, as demonstrated in rotarod test (FIG. 28, Panel B).

Discussion

A long-term objective of these investigations is to develop an active targeted cell-mediated delivery of therapeutic proteins to the brain. We demonstrated here that genetically-modified macrophages can produce therapeutically-active neurotrophic factor, GDNF, and release it in extracellular vesicles, exosomes. The most important finding of this work is that GDNF-transfected macrophages provide significant neuronal protection in a PD mouse model. Our in vivo experiments demonstrated that systemically administered GDNF-expressing macrophages migrate across the BBB towards the inflammation site in large numbers, and provide efficient sustained delivery of their drug payload at the disease site that is consistent with previously reported findings (Batrakova et al., Bioconjug Chem 18: 1498-1506 (2007); Brynskikh et al., Nanomedicine (Lond) 5: 379-396 (2010); Haney et al., Nanomedicine (Lond) 7: 815-833 (2012); Haney et al., Plos One 8: e61852 (2013); Haney et al., Nanomedicine (Lond) 6: 1215-1230 (2011)). To enforce outcomes of the new formulation, a specific subset of "alternatively activated" (M2) macrophages with regenerative functions was used. Thus, macrophages, polarized to M2 regenerative subtype, represent biologically-active carriers that can promote neuronal regeneration enhancing the therapeutic efficacy of drug formulations.

The mechanism of the macrophage-mediated drug delivery is not fully understood. Thus, several independent processes may serve to improve GDNF-expressing macrophage therapeutics. In addition to the targeted tissue-specific delivery of therapeutics in macrophages (Brynskikh et al., Nanomedicine (Land) 5: 379-396 (2010); Zhao et al., J Nanomed Nanotechnol S4 (2011)), drug-carrying macrophages were shown to increase time circulation in the blood, and therefore permit sustained release of the therapeutic protein allowing the drug to enter the brain, independent of carrier cells ("depot effect"). Furthermore, drug-loaded macrophages release GDNF incorporated in exosomes that can facilitate the drug transfer from carrier cells to the target cells (Haney et al., Nanomedicine (Lond) 7: 815-833 (2012)). We reported earlier that exosomes secreted from preloaded with nanoformulated catalase macrophages attach to the plasma membranes, and discharge their carp into target cells (Haney et al., Nanomedicine (Land) 7: 815-833 (2012)). As a result, the drug-incorporated nanoparticles were transferred from macrophages to adjacent cells, and diffused broadly throughout the recipient cells avoiding degradation in lysosomes. This mechanism enabled the drug to reach different intracellular compartments such as mitochondria, cytoplasm, and endoplasmic reticulum, and produce a powerful therapeutic effects (Haney et al., Nanomedicine (Lond) 7: 815-833 (2012)). Furthermore, in our earlier studies, we demonstrated that macrophages transfected with catalase-encoded plasmid DNA (pDNA) can also release exosomes with the enzyme, and facilitate catalase transfer to target cells of a neurovascular unit: neurons, astrocytes, and brain microvessel endothelial cells (Haney et al., Nanomedicine (Lond) 7: 815-833 (2012); Haney et al., Plos One 8: e61852 (2013); Haney et al., Nanomedicine (Lond) 6: 1215-1230 (2011)). This resulted in profound therapeutic effects of macrophage-mediated catalase delivery in mouse models of PD (Brynskikh et al., Nanomedicine (Lond) 5: 379-396 (2010); Haney et al., Plos One 8: e61852 (2013)). We speculated that the same facilitated transfer and favorable intracellular localization of GDNF incorporated into exosomes released from genetically-modified macrophages may support the protective activity in neurons of the macrophage-mediated drug delivery system.

Using genetically-modified macrophages as a cell-mediated drug delivery system will target the therapeutic proteins to the brain, prolong drug half-live, and diminish drug immunogenicity. In addition, properly differentiated immune cells accumulating in traumatic, degenerative, ischemic, infectious, and autoimmune lesions of the nervous system might provide a neuroprotective effect, which may further boost the therapeutic effect of cell-mediated drug delivery systems. It is anticipated that these studies will lead to the developing a new technology based on active targeted cell-mediated delivery of therapeutic polypeptides that produce neuroprotection and neuroregeneration in patients with PD.

EXAMPLE 7

Figure 29:
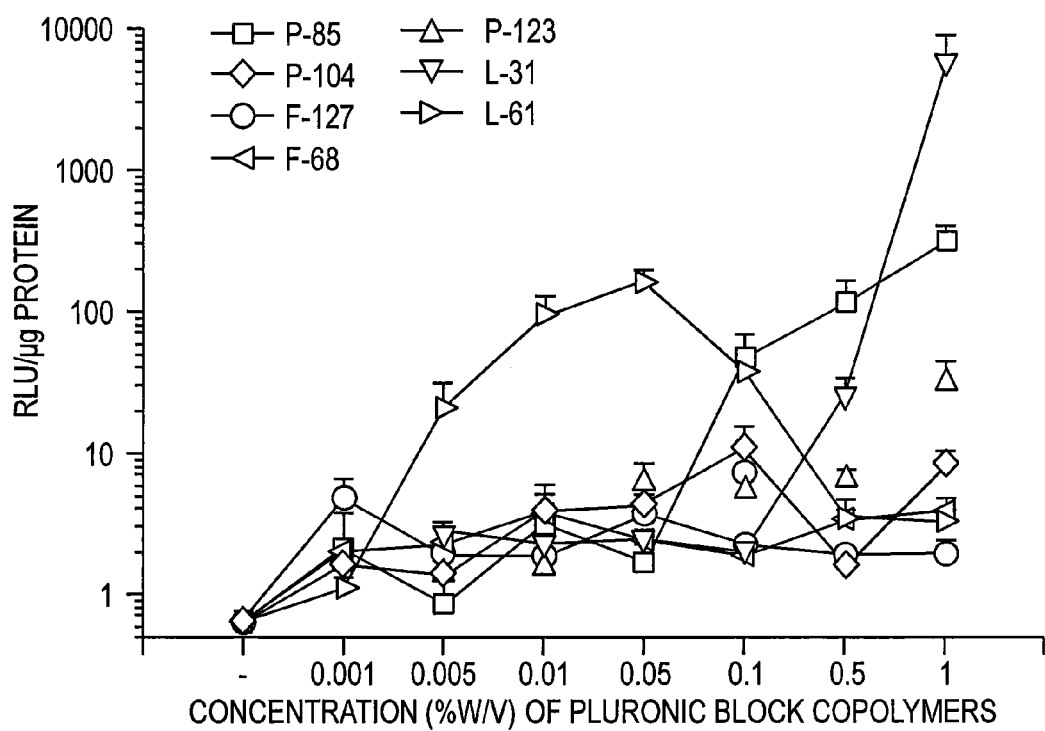
FIG. 29 shows the effect of block copolymers on gene expression in RAW 264.7 macrophages. 500,000 RAW264.7 macrophages were treated in vitro with 1 μg DNA alone or mixed with increasing concentration of Pluronic® block copolymers in serum free media for 2 h. The treatment media was replaced with complete media (serum free media supplemented with 10% FBS) and the gene expression levels were observed in cell lysates after 24 h. Data are mean±SEM (n=4).

The role of block copolymers (Pluronics®) in macrophage transfection in vitro was tested. 500,000 RAW264.7 macrophages were treated with 1 µg plasmid DNA (gWIZ™Luc (Genlantis, CA)) alone or mixed with increasing concentration of Pluronic® block copolymers in serum free media for 2 h. The treatment media was replaced with complete media and the gene expression levels were observed in cell lysates after 24 h. As is seen in FIG. 29, the block copolymer with intermediate hydrophobicity, P85 (HLB ~16) and the PO block length of ca. 2,300 elicits an increase in gene expression by nearly 3 orders of magnitude. Also the hydrophobic copolymer L61 (HLB ~3) with PO block length of ca. 1,800 is quite active at relatively low concentrations of ca. 0.05% wt. Another hydrophobic copolymer L31 (HLB ~1 to 7) with PO block length of ca. 1000 is very active albeit at higher concentrations of ca. 1% wt. Yet another hydrophobic copolymer P123 (HLB ~8) and PO block length of ca. 3,600 is somewhat less active at the same high concentrations. The copolymer with intermediate hydrophobicity (HLB ~13) and PO block length of ca. 3,000 is even less active than P123 and much less active than P85. The hydrophilic copolymers, F68 (HLB ~29) with PO block length of ca. 1800 and F127 (HLB ~22) with PO block length of ca. 3600 are practically inactive.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of transferring a nucleic acid to a target cell, comprising:
    first transiently transfecting an immune system cell with the nucleic acid, and
    then contacting the target cell with the immune system cell that has been transiently transfected with the nucleic acid,
    wherein the nucleic acid is transferred to the target cell,
    wherein the immune system cell is a macrophage or monocyte and the target cell is a neuron, muscle cell, or fibroblast, and
    wherein the nucleic acid is RNA.

2. The method of claim 1, wherein the target cell is an in vitro or ex vivo cell.

3. The method of claim 2, wherein contacting the target cell comprises co-culturing the target cell and the transiently transfected immune system cell.

4. The method of claim 1, wherein the target cell is a cell in a subject and contacting the target cell comprises administering the transiently transfected immune system cell to the subject.

5. The method of claim 4, wherein the immune system cell is obtained from said subject.

6. A method of transferring a nucleic acid to a target cancer cell, comprising:
    first transiently transfecting an immune system cell with the nucleic acid, and
    then contacting the target cancer cell with the immune system cell that has been transiently transfected with the nucleic acid,
    wherein the nucleic acid is transferred to the target cell, and
    wherein the immune system cell is a macrophage or monocyte.

7. A method of transferring a nucleic acid to a target cell, comprising: first transiently transfecting an immune system cell with the nucleic acid in vitro or ex vivo, and then contacting the target cell with the immune system cell that has been transiently transfected with the nucleic acid,
    wherein the nucleic acid is transferred to the target cell,
    wherein the immune system cell is a macrophage or monocyte, and
    wherein the nucleic acid is RNA.

8. The method of claim 7, wherein the target cell is an in vitro or ex vivo cell.

9. The method of claim 8, wherein contacting the target cell comprises co-culturing the target cell and the transiently transfected immune system cell.

10. The method of claim 7, wherein the target cell is a cell in a subject and contacting the target cell comprises administering the transiently transfected immune system cell to the subject.

11. The method of claim 10, wherein the immune system cell is obtained from said subject.

* * * * *

UNITED STATES PATENT AND TRADEMARK OFFICE
CERTIFICATE OF CORRECTION

PATENT NO.         : 9,789,205 B2
APPLICATION NO.    : 14/537547
DATED              : October 17, 2017
INVENTOR(S)        : Kabanov et al.

Page 1 of 1

It is certified that error appears in the above-identified patent and that said Letters Patent is hereby corrected as shown below:

On the Title Page

Item (60) Related U.S. Application Data:
Please add -- Continuation-in-part of application No. PCT/US 2013/040577, filed on May 10, 2013. --

Signed and Sealed this
Thirty-first Day of July, 2018

Andrei Iancu
*Director of the United States Patent and Trademark Office*